US009885061B2

(12) United States Patent
McPhee

(10) Patent No.: US 9,885,061 B2
(45) Date of Patent: Feb. 6, 2018

(54) MICROBIAL DERIVED ISOPRENE AND METHODS FOR MAKING THE SAME

(71) Applicant: AMYRIS, INC., Emeryville, CA (US)

(72) Inventor: Derek McPhee, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 119 days.

(21) Appl. No.: 14/956,402

(22) Filed: Dec. 2, 2015

(65) Prior Publication Data

US 2016/0083750 A1 Mar. 24, 2016

Related U.S. Application Data

(62) Division of application No. 13/887,381, filed on May 6, 2013, now Pat. No. 9,233,894, which is a division of application No. 13/629,623, filed on Sep. 28, 2012, now Pat. No. 8,492,605, which is a division of (Continued)

(51) Int. Cl.

| | |
|---|---|
| ***C07C 7/09*** | (2006.01) |
| ***C07C 11/16*** | (2006.01) |
| ***C12P 5/00*** | (2006.01) |
| ***C12M 1/00*** | (2006.01) |

(52) U.S. Cl.

CPC ................ *C12P 5/007* (2013.01); *C07C 7/09* (2013.01); *C07C 11/16* (2013.01); *C12M 47/20* (2013.01); *Y02E 50/343* (2013.01)

(58) Field of Classification Search

None

See application file for complete search history.

(56) References Cited

U.S. PATENT DOCUMENTS

| | | | | |
|---|---|---|---|---|
| 3,301,915 | A * | 1/1967 | King | C07C 7/005 203/28 |
| 3,692,861 | A * | 9/1972 | Chikatsu | C07C 7/005 203/28 |
| 7,931,873 | B2 | 4/2011 | Lovegrove et al. | |

(Continued)

FOREIGN PATENT DOCUMENTS

| | | |
|---|---|---|
| WO | WO2008003078 A2 | 1/2008 |
| WO | WO2008137092 | 11/2008 |

(Continued)

OTHER PUBLICATIONS

G.M. Silver et al., Enzymatic Synthesis of Isoprene From Dimethylallyl Diphosphate in Aspen Leaf Extracts, Plant Physiol., 97, 1588-1591 (1991).

(Continued)

*Primary Examiner* — Tam M Nguyen

(74) *Attorney, Agent, or Firm* — Kam W. Law; Squire Patton Boggs (US) LLP

(57) ABSTRACT

Provided herein is a gaseous isoprene composition comprising isoprene, carbon dioxide and water, wherein the isoprene is in an amount between about 0.1% and about 15% by volume; wherein the carbon dioxide is in an amount between about 0.04% and about 35% by volume; wherein the water is in an amount greater than about 70% of its saturation amount. Also provided herein is a liquid isoprene composition comprising isoprene in an amount of at least 65% by weight and carbon dioxide in an amount between about 0.01% and about 1% by weight.

7 Claims, 9 Drawing Sheets

Related U.S. Application Data application No. 12/659,216, filed on Mar. 1, 2010, now Pat. No. 8,324,442.

(60) Provisional application No. 61/202,474, filed on Mar. 3, 2009.

(56) References Cited

U.S. PATENT DOCUMENTS

| | | | | |
|---|---|---|---|---|
| 9,656,929 | B2 * | 5/2017 | Abdelghani | C07C 7/08 |
| 2004/0241246 | A1 * | 12/2004 | Lipman | A61L 15/58 424/486 |
| 2007/0110978 | A1 * | 5/2007 | Kawaguchi | B32B 15/06 428/292.1 |
| 2007/0142550 | A1 * | 6/2007 | Scurati | B60C 1/00 525/70 |
| 2009/0203102 | A1 * | 8/2009 | Cervin | C12N 9/1022 435/167 |
| 2010/0167371 | A1 * | 7/2010 | Chotani | C12P 5/026 435/167 |

FOREIGN PATENT DOCUMENTS

| | | |
|---|---|---|
| WO | Wo2009100231 | 8/2009 |
| WO | WO2010003007 A2 | 1/2010 |
| WO | WO2010031076 A2 | 3/2010 |
| WO | WO2010101855 | 9/2010 |

OTHER PUBLICATIONS

Communication pursuant to Article 94(3) EPC of the corresponding EP application, dated May 18, 2016.

Newman, et al., "High-level Production of Amorpha-4,11-Diene in a Two-Phase Partitioning Bioreactor of Metabolically Engineered *Escherichia coil*", Biotechnology and Bioengineering, vol. 95. No. 4, Nov. 5, 2006, pp. 684-691.

ISR of PCT/US2010/025826.

Written Opinion of PCT/US20101025826.

IPRP of PCT/US2010/025826.

* cited by examiner

Mevalonate Pathway acetyl-CoA acetoacetyl-CoA 3-hydroxy-3-methylglutaryl-CoA mevalonate mevalonate 5-phosphate mevalonate 5-diphosphate Isopentenyl diphosphate (IPP)

DXP Pathway

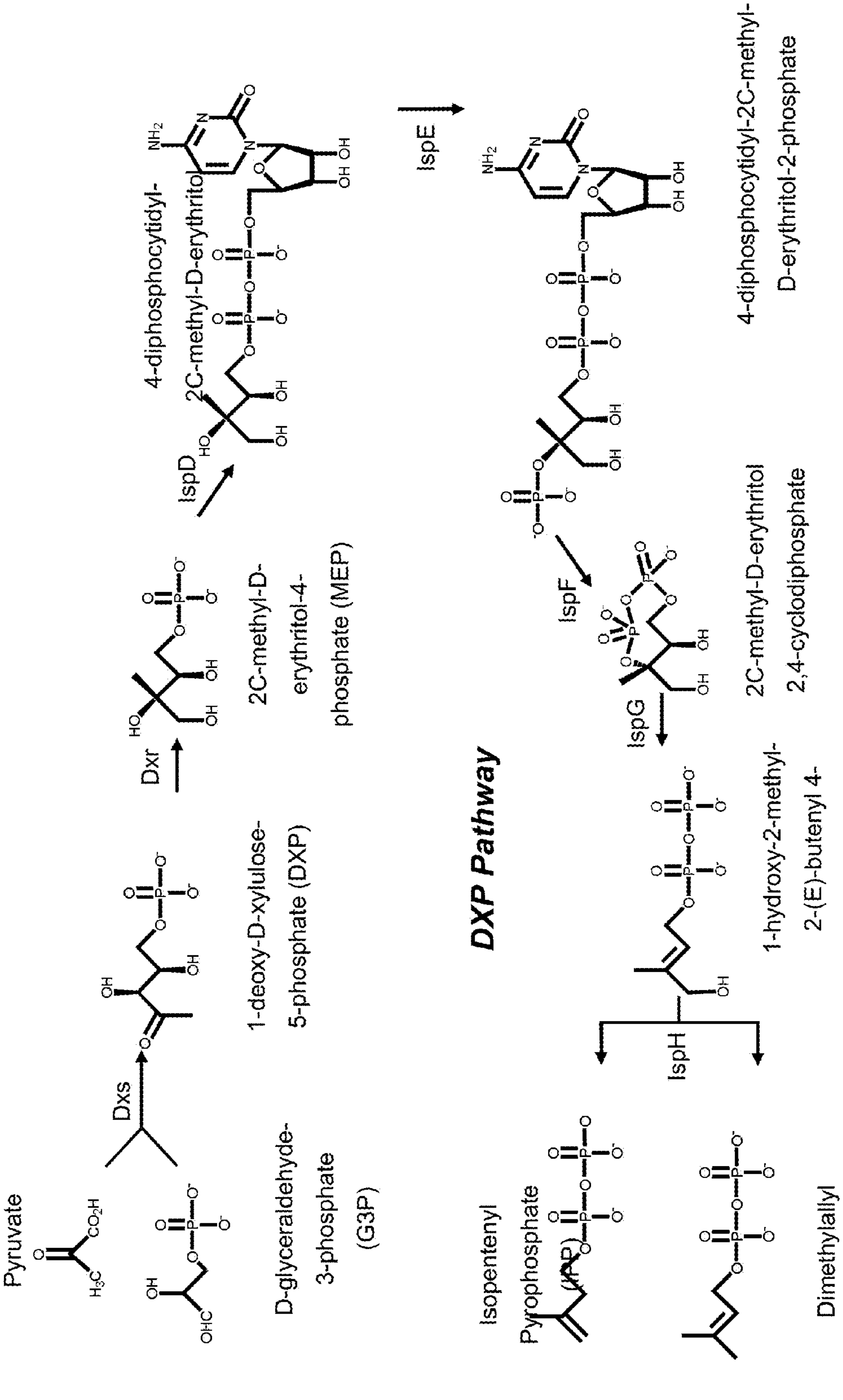

Pyruvate

D-glyceraldehyde-3-phosphate (G3P)

1-deoxy-D-xylulose-5-phosphate (DXP)

2C-methyl-D-erythritol-4-phosphate (MEP)

4-diphosphocytidyl-2C-methyl-D-erythritol 4-diphosphocytidyl-2C-methyl-D-erythritol-2-phosphate 2C-methyl-D-erythritol 2,4-cyclodiphosphate 1-hydroxy-2-methyl-2-(E)-butenyl 4-diphosphate Isopentenyl Pyrophosphate (IPP)

Dimethylallyl Pyrophosphate (DMAPP)

Figure 4

SEQUENCE LISTING

<160> NUMBER OF SEQ ID NOS: 128

<210> SEQ ID NO 1
<211> LENGTH: 1737
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 1
ggatccatgt caactttgcc tatttcttct gtgtcatttt cctcttctac atcaccatta 60
gtcgtggacg acaaagtctc aaccaagccc gacgttatca gacatacaat gaatttcaat 120
gcttctattt ggggagatca attcttgacc tatgatgagc ctgaagattt agttatgaag 180
aaacaattag tggaggaatt aaaagaggaa gttaagaagg aattgataac tatcaaaggt 240
tcaaatgagc ccatgcagca tgtgaaattg attgaattaa ttgatgctgt tcaacgttta 300
ggtatagctt accattttga agaagagatc gaggaagctt tgcaacatat acatgttacc 360
tatggtgaac agtgggtgga taaggaaaat ttacagagta tttcattgtg gttcaggttg 420
ttgcgtcaac agggctttaa cgtctcctct ggcgttttca aagactttat ggacgaaaaa 480
ggtaaattca aagagtcttt atgcaatgat gcacaaggaa tattagcctt atatgaagct 540
gcatttatga gggttgaaga tgaaaccatc ttagacaatg ctttggaatt cacaaaagtt 600
catttagata tcatagcaaa agacccatct tgcgattctt cattgcgtac acaaatccat 660
caagccttaa aacaaccttt aagaaggaga ttagcaagga ttgaagcatt acattacatg 720
ccaatctacc aacaggaaac atctcatgat gaagtattgt tgaaattagc caagttggat 780
ttcagtgttt tgcagtctat gcataaaaag gaattgtcac atatctgtaa gtggtggaaa 840
gatttagatt tacaaaataa gttaccttat gtacgtgatc gtgttgtcga aggctacttc 900

```
tggatattgt ccatatacta tgagccacaa cacgctagaa caagaatgtt tttgatgaaa    960

acatgcatgt ggttagtagt tttggacgat acttttgata attatggaac atacgaagaa   1020

ttggagattt ttactcaagc cgtcgagaga tggtctatct catgcttaga tatgttgccc   1080

gaatatatga aattaatcta ccaagaatta gtcaatttgc atgtggaaat ggaagaatct   1140

ttggaaaagg agggaaagac ctatcagatt cattacgtta aggagatggc taaagaatta   1200

gttcgtaatt acttagtaga agcaagatgg ttgaaggaag gttatatgcc tactttagaa   1260

gaatacatgt ctgtttctat ggttactggt acttatggtt tgatgattgc aaggtcctat   1320

gttggcagag gagacattgt tactgaagac acattcaaat gggtttctag ttacccacct   1380

attattaaag cttcctgtgt aatagtaaga ttaatggacg atattgtatc tcacaaggaa   1440

gaacaagaaa gaggacatgt ggcttcatct atagaatgtt actctaaaga atcaggtgct   1500

tctgaagagg aagcatgtga atatattagt aggaaagttg aggatgcctg gaaagtaatc   1560

aatagagaat ctttgcgtcc aacagccgtt cccttccctt tgttaatgcc agcaataaac   1620

ttagctagaa tgtgtgaggt cttgtactct gttaatgatg gttttactca tgctgagggt   1680

gacatgaaat cttatatgaa gtccttcttc gttcatccta tggtcgtttg actcgag      1737
```

<210> SEQ ID NO 2
<211> LENGTH: 7348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatcga ctacgtcgta aggccgtttc tgacagagta aaattcttga gggaactttc    240

accattatgg gaaatgcttc aagaaggtat tgacttaaac tccatcaaat ggtcaggtca    300

ttgagtgttt tttatttgtt gtattttttt ttttttagag aaaatcctcc aatatcaaat    360

taggaatcgt agtttcatga ttttctgtta cacctaactt tttgtgtggt gccctcctcc    420

ttgtcaatat taatgttaaa gtgcaattct tttccttat cacgttgagc cattagtatc     480

aatttgctta cctgtattcc tttactatcc tccttttttct ccttcttgat aaatgtatgt   540

agattgcgta tatagtttcg tctaccctat gaacatattc cattttgtaa tttcgtgtcg    600

tttctattat gaatttcatt tataaagttt atgtacaaat atcataaaaa aagagaatct    660

ttttaagcaa ggattttctt aacttcttcg gcgacagcat caccgacttc ggtggtactg    720

ttggaaccac ctaaatcacc agttctgata cctgcatcca aaaccttttt aactgcatct    780

tcaatggcct taccttcttc aggcaagttc aatgacaatt tcaacatcat tgcagcagac    840

aagatagtgg cgatagggtc aaccttattc tttggcaaat ctggagcaga accgtggcat    900

ggttcgtaca aaccaaatgc ggtgttcttg tctggcaaag aggccaagga cgcagatggc    960

aacaaaccca aggaacctgg gataacggag gcttcatcgg agatgatatc accaaacatg   1020

ttgctggtga ttataatacc atttaggtgg gttgggttct taactaggat catggcggca   1080

gaatcaatca attgatgttg aaccttcaat gtagggaatt cgttcttgat ggtttcctcc   1140

acagtttttc tccataatct tgaagaggcc aaaagattag ctttatccaa ggaccaaata   1200
```

-continued ggcaatggtg gctcatgttg tagggccatg aaagcggcca ttcttgtgat tctttgcact 1260
tctggaacgg tgtattgttc actatcccaa gcgacaccat caccatcgtc ttcctttctc 1320
ttaccaaagt aaatacctcc cactaattct ctgacaacaa cgaagtcagt acctttagca 1380
aattgtggct tgattggaga taagtctaaa agagagtcgg atgcaaagtt acatggtctt 1440
aagttggcgt acaattgaag ttctttacgg atttttagta aaccttgttc aggtctaaca 1500
ctaccggtac cccatttagg accagccaca gcacctaaca aaacggcatc aaccttcttg 1560
gaggcttcca gcgcctcatc tggaagtgga acacctgtag catcgatagc agcaccacca 1620
attaaatgat tttcgaaatc gaacttgaca ttggaacgaa catcagaaat agctttaaga 1680
accttaatgg cttcggctgt gatttcttga ccaacgtggt cacctggcaa aacgacgatc 1740
ttcttagggg cagacattac aatggtatat ccttgaaata tatataaaaa aaggcgcctt 1800
agaccgctcg gccaaacaac caattacttg ttgagaaata gagtataatt atcctataaa 1860
tataacgttt ttgaacacac atgaacaagg aagtacagga caattgattt tgaagagaat 1920
gtggattttg atgtaattgt tgggattcca tttttaataa ggcaataata ttaggtatgt 1980
ggatatacta gaagttctcc tcgaccgtcg atatgcggtg tgaaataccg cacagatgcg 2040
taaggagaaa ataccgcatc aggaaattgt aaacgttaat attttgttaa aattcgcgtt 2100
aaatttttgt taaatcagct catttttaa ccaataggcc gaaatcggca aaatccctta 2160
taaatcaaaa gaatagaccg agatagggtt gagtgttgtt ccagtttgga acaagagtcc 2220
actattaaag aacgtggact ccaacgtcaa agggcgaaaa accgtctatc agggcgatgg 2280
cccactacgt gaaccatcac cctaatcaag ttttttgggg tcgaggtgcc gtaaagcact 2340
aaatcggaac cctaaaggga gcccccgatt tagagcttga cggggaaagc cggcgaacgt 2400
ggcgagaaag gaagggaaga aagcgaaagg agcgggcgct agggcgctgg caagtgtagc 2460
ggtcacgctg cgcgtaacca ccacacccgc cgcgcttaat gcgccgctac agggcgcgtc 2520
gcgccattcg ccattcaggc tgcgcaactg ttgggaaggg cgatcggtgc gggcctcttc 2580
gctattacgc cagctgaatt ggagcgacct catgctatac ctgagaaagc aacctgacct 2640
acaggaaaga gttactcaag aataagaatt ttcgttttaa aacctaagag tcactttaaa 2700
atttgtatac acttattttt tttataactt atttaataat aaaaatcata aatcataaga 2760
aattcgctta tttagaagtg tcaacaacgt atctaccaac gatttgaccc ttttccatct 2820
tttcgtaaat ttctggcaag gtagacaagc cgacaacctt gattggagac ttgaccaaac 2880
ctctggcgaa gaattgttaa ttaagagctc agatcttatc gtcgtcatcc ttgtaatcca 2940
tcgatactag tgcggccgcc ctttagtgag ggttgaattc gaattttcaa aaattcttac 3000 ttttttttg gatggacgca aagaagttta ataatcatat tacatggcat taccaccata 3060
tacatatcca tatacatatc catatctaat cttacttata tgttgtggaa atgtaaagag 3120
ccccattatc ttagcctaaa aaaaccttct ctttggaact ttcagtaata cgcttaactg 3180
ctcattgcta tattgaagta cggattagaa gccgccgagc gggtgacagc cctccgaagg 3240
aagactctcc tccgtgcgtc ctcgtcttca ccggtcgcgt tcctgaaacg cagatgtgcc 3300
tcgcgccgca ctgctccgaa caataaagat tctacaatac tagcttttat ggttatgaag 3360
aggaaaaatt ggcagtaacc tggccccaca aaccttcaaa tgaacgaatc aaattaacaa 3420
ccataggatg ataatgcgat tagtttttta gccttatttc tggggtaatt aatcagcgaa 3480
gcgatgattt ttgatctatt aacagatata taaatgcaaa aactgcataa ccactttaac 3540
taatactttc aacattttcg gtttgtatta cttcttattc aaatgtaata aaagtatcaa 3600

-continued

```
caaaaaattg ttaatatacc tctatacttt aacgtcaagg agaaaaaacc ccggatccgt   3660
aatacgactc actatagggc ccgggcgtcg acatggaaca gaagttgatt tccgaagaag   3720
acctcgagta agcttggtac cgcggctagc taagatccgc tctaaccgaa aaggaaggag   3780
ttagacaacc tgaagtctag gtccctattt atttttttat agttatgtta gtattaagaa   3840
cgttatttat atttcaaatt tttctttttt ttctgtacag acgcgtgtac gcatgtaaca   3900
ttatactgaa aaccttgctt gagaaggttt tgggacgctc gaagatccag ctgcattaat   3960
gaatcggcca acgcgcgggg agaggcggtt tgcgtattgg gcgctcttcc gcttcctcgc   4020
tcactgactc gctgcgctcg gtcgttcggc tgcggcgagc ggtatcagct cactcaaagg   4080
cggtaatacg gttatccaca gaatcagggg ataacgcagg aaagaacatg tgagcaaaag   4140
gccagcaaaa ggccaggaac cgtaaaaagg ccgcgttgct ggcgtttttc cataggctcc   4200
gcccccctga cgagcatcac aaaaatcgac gctcaagtca gaggtggcga aacccgacag   4260
gactataaag ataccaggcg tttccccctg gaagctccct cgtgcgctct cctgttccga   4320
ccctgccgct taccggatac ctgtccgcct ttctcccttc gggaagcgtg gcgctttctc   4380
atagctcacg ctgtaggtat ctcagttcgg tgtaggtcgt tcgctccaag ctgggctgtg   4440
tgcacgaacc ccccgttcag cccgaccgct gcgccttatc cggtaactat cgtcttgagt   4500
ccaacccggt aagacacgac ttatcgccac tggcagcagc cactggtaac aggattagca   4560
gagcgaggta tgtaggcggt gctacagagt tcttgaagtg gtggcctaac tacggctaca   4620
ctagaaggac agtatttggt atctgcgctc tgctgaagcc agttaccttc ggaaaaagag   4680
ttggtagctc ttgatccggc aaacaaacca ccgctggtag cggtggtttt tttgtttgca   4740
agcagcagat tacgcgcaga aaaaaaggat ctcaagaaga tcctttgatc ttttctacgg   4800
ggtctgacgc tcagtggaac gaaaactcac gttaagggat tttggtcatg agattatcaa   4860
aaaggatctt cacctagatc cttttaaatt aaaaatgaag ttttaaatca atctaaagta   4920
tatatgagta aacttggtct gacagttacc aatgcttaat cagtgaggca cctatctcag   4980
cgatctgtct atttcgttca tccatagttg cctgactccc cgtcgtgtag ataactacga   5040
tacgggaggg cttaccatct ggccccagtg ctgcaatgat accgcgagac ccacgctcac   5100
cggctccaga tttatcagca ataaaccagc cagccggaag ggccgagcgc agaagtggtc   5160
ctgcaacttt atccgcctcc atccagtcta ttaattgttg ccgggaagct agagtaagta   5220
gttcgccagt taatagtttg cgcaacgttg ttgccattgc tacaggcatc gtggtgtcac   5280
gctcgtcgtt tggtatggct tcattcagct ccggttccca acgatcaagg cgagttacat   5340
gatcccccat gttgtgcaaa aaagcggtta gctccttcgg tcctccgatc gttgtcagaa   5400
gtaagttggc cgcagtgtta tcactcatgg ttatggcagc actgcataat tctcttactg   5460
tcatgccatc cgtaagatgc ttttctgtga ctggtgagta ctcaaccaag tcattctgag   5520
aatagtgtat gcggcgaccg agttgctctt gcccggcgtc aatacgggat aataccgcgc   5580
cacatagcag aactttaaaa gtgctcatca ttggaaaacg ttcttcgggg cgaaaactct   5640
caaggatctt accgctgttg agatccagtt cgatgtaacc cactcgtgca cccaactgat   5700
cttcagcatc ttttactttc accagcgttt ctgggtgagc aaaaacagga aggcaaaatg   5760
ccgcaaaaaa gggaataagg gcgacacgga aatgttgaat actcatactc ttcctttttc   5820
aatattattg aagcatttat cagggttatt gtctcatgag cggatacata tttgaatgta   5880
tttagaaaaa taaacaaata ggggttccgc gcacatttcc ccgaaaagtg ccacctgaac   5940
```

```
gaagcatctg tgcttcattt tgtagaacaa aaatgcaacg cgagagcgct aatttttcaa   6000

acaaagaatc tgagctgcat ttttacagaa cagaaatgca acgcgaaagc gctattttac   6060

caacgaagaa tctgtgcttc atttttgtaa aacaaaaatg caacgcgaga gcgctaattt   6120

ttcaaacaaa gaatctgagc tgcattttta cagaacagaa atgcaacgcg agagcgctat   6180

tttaccaaca aagaatctat acttcttttt tgttctacaa aaatgcatcc cgagagcgct   6240

atttttctaa caaagcatct tagattactt tttttctcct ttgtgcgctc tataatgcag   6300

tctcttgata actttttgca ctgtaggtcc gttaaggtta gaagaaggct actttggtgt   6360

ctattttctc ttccataaaa aaagcctgac tccacttccc gcgtttactg attactagcg   6420

aagctgcggg tgcatttttt caagataaag gcatccccga ttatattcta taccgatgtg   6480

gattgcgcat actttgtgaa cagaaagtga tagcgttgat gattcttcat tggtcagaaa   6540

attatgaacg gtttcttcta ttttgtctct atatactacg tataggaaat gtttacattt   6600

tcgtattgtt ttcgattcac tctatgaata gttcttacta caattttttt gtctaaagag   6660

taatactaga gataaacata aaaaatgtag aggtcgagtt tagatgcaag ttcaaggagc   6720

gaaaggtgga tgggtaggtt atatagggat atagcacaga gatatatagc aaagagatac   6780

ttttgagcaa tgtttgtgga agcggtattc gcaatatttt agtagctcgt tacagtccgg   6840

tgcgtttttg gtttttgaa agtgcgtctt cagagcgctt ttggttttca aaagcgctct   6900

gaagttccta tactttctag agaataggaa cttcggaata ggaacttcaa agcgtttccg   6960

aaaacgagcg cttccgaaaa tgcaacgcga gctgcgcaca tacagctcac tgttcacgtc   7020

gcacctatat ctgcgtgttg cctgtatata tatatacatg agaagaacgg catagtgcgt   7080

gtttatgctt aaatgcgtac ttatatgcgt ctatttatgt aggatgaaag gtagtctagt   7140

acctcctgtg atattatccc attccatgcg gggtatcgta tgcttccttc agcactaccc   7200

tttagctgtt ctatatgctg ccactcctca attggattag tctcatcctt caatgctatc   7260

atttcctttg atattggatc atactaagaa accattatta tcatgacatt aacctataaa   7320

aataggcgta tcacgaggcc ctttcgtc                                      7348
```

<210> SEQ ID NO 3
<211> LENGTH: 952
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
taagtagttg accatagctc ttccatggct accaatttgt tgtgcttgtc taacaaattg     60

tcatcaccaa caccaactcc atctaccagg ttcccacaat ctaaaaactt cattactcaa    120

aagacctcat tggccaatcc taagccctgg agagtaatct gtgcaacctc atcacagttc    180

acccagatca cagaacataa ctctaggagg tcagcaaatt accagcctaa tttgtggaac    240

ttcgagttct tgcagtcttt ggagaatgat ttaaaggtcg aaaagttgga ggaaaaggct    300

acaaaattag aagaggaggt caggtgtatg atcaacaggg tagatactca gcctttgtca    360

ttgttagagt tgatagacga tgtccaaagg ttgggtttga cctataagtt tgaaaaggac    420

atcatcaagg ccttggaaaa catcgtttta ttggacgaga ataagaagaa caagtctgac    480

ttacacgcca cagcattatc tttcaggttg ttgagacaac acggattcga ggtatctcag    540

gacgtctttg aaagatttaa agacaaggag ggaggttttt caggagaatt aaaaggagat    600
```

```
gtccaaggtt tgttgtcatt atacgaggcc tcatatttag gttttgaggg tgagaactta    660

ttggaagaag caaggacctt ttcaatcacc cacttgaaga ataacttaaa ggagggaata    720

aataccaagg tagctgagca agtatcacac gcattggaat taccttatca tcagagattg    780

cataggttag aagccagatg gtttttggat aagtatgaac ctaaggagcc tcaccaccag    840

ttattgttgg agttagccaa gttggacttt aatatggtcc aaacattaca ccagaaagag    900

ttgcaggact tgtctagatg gtggacagag atggggaaga gctggcttat tg            952
```

<210> SEQ ID NO 4
<211> LENGTH: 999
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4

```
taagtagttg accatagctc ttccaaagag ttgcaggact tgtctagatg gtggacagag     60

atgggattgg catctaaatt agacttcgtc agagataggt tgatggaagt atatttctgg    120

gctttaggta tggcccctga tcctcaattt ggagagtgca gaaaagctgt aacaaaaatg    180

ttcggattag tcaccataat tgacgacgtt tatgacgttt acggtacatt ggacgagtta    240

caattgttta ctgatgcagt tgaaaggtgg gacgtcaatg ccattaatac cttaccagac    300

tacatgaaat tgtgcttctt agctttatac aacacagtaa acgacacatc ttactcaatc    360

ttgaaggaga agggtcacaa caacttgtct tacttgacta aatcttggag ggagttgtgt    420

aaagccttct tacaagaggc caagtggtca aacaacaaaa taatccctgc tttttcaaaa    480

tacttggaga acgcctctgt ctcttcatct ggagtagcat tattggcacc ttcatacttc    540

tctgtttgcc agcaacaaga ggacatatct gatcacgctt tgagatcatt aaccgatttt    600

cacggtttgg tacgatcttc atgcgtcata ttcagattat gcaatgactt agctacttca    660

gctgcagagt tagagagagg agagaccacc aactcaatca tctcttatat gcacgaaaac    720

gacggcacct cagaggaaca agcaagagag gagttgagga agttaatcga cgcagagtgg    780

aaaaagatga acagggagag ggtctctgat tcaacattgt tgccaaaggc cttcatggag    840

atagccgtca atatggccag ggtctcacac tgcacatatc agtacggtga cggtttgggt    900

aggcctgact acgccaccga gaataggatc aagttgttgt tgatcgaccc ttttcctatt    960

aatcagttga tgtatgtctg aggaagagct ggcttattg                           999
```

<210> SEQ ID NO 5
<211> LENGTH: 932
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5

```
taagtagttg accatagctc ttccatggct accgagttgt tgtgcttgca caggccaata     60

tctttgaccc acaaattgtt caggaatcca ttgccaaaag tcatacaagc aacaccattg    120

accttgaagt taaggtgctc tgtatcaacc gagaacgttt cattcacaga gacagaaaca    180

gaaacaagga ggtcagctaa ttacgagcca aactcatggg attatgacta cttgttgtct    240

tctgacaccg acgagtctat tgaggtatat aaagacaagg caaagaagtt ggaggctgaa    300

gtcaggaggg agatcaacaa cgaaaaggca gagttcttga ctttgccaga gttgattgac    360
```

```
aacgtacaga ggttgggatt gggttatagg tttgagtcag acataagaag ggctttggac    420

aggtttgtat cttcaggtgg attcgacgca gttactaaga cctcattgca tgctaccgct    480

ttatctttta ggttattgag acagcatggt ttcgaagtat cacaggaggc attctcagga    540

ttcaaagacc agaacggaaa ctttttgaag aacttgaagg aggacataaa agccatcttg    600

tctttatacg aagcctcatt tttggcctta gagggtgaga atattttaga cgaggctaag    660

gtcttcgcca tatctcactt gaaggagttg tctgaggaga aaataggaaa ggacttagcc    720

gaacaagtaa accacgcatt ggaattacca ttgcatagga gaactcaaag gttagaagca    780

gtctggtcta tcgaggccta caggaagaaa gaggatgctg atcaggtttt attggagttg    840

gccatcttag actacaacat gatccagtca gtctatcaga gagacttgag agaaacttct    900

aggtggtgga gaagggaaga gctggcttat tg                                  932
```

```
<210> SEQ ID NO 6
<211> LENGTH: 970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

taagtagttg accatagctc ttcccttgag agaaacttct aggtggtgga gaagagtcgg     60

attagccact aaattgcact tcgctaggga taggttaata gagtcattct attgggctgt    120

tggagtagct tttgaaccac aatactcaga ttgtaggaac tcagtagcca agatgttctc    180

attcgtcacc ataatcgatg acatctacga cgtatacgga actttggatg aattggaatt    240

attcactgat gcagtcgaga gatgggacgt aaatgccatt gatgacttgc ctgattacat    300

gaagttgtgc ttcttagctt tgtacaacac cataaacgag atcgcatacg acaacttgaa    360

ggacaagggt gaaaatatat tgccttactt aaccaaggcc tgggctgatt tgtgtaacgc    420

attcttacag gaagcaaaat ggttgtataa caaatcaaca cctactttcg acgagtattt    480

tggtaacgct tggaagtctt catctggacc tttacaattg gtatttgctt acttcgccgt    540

cgtacaaaac attaagaaag aggagattga taacttgcaa aagtaccacg atatcatctc    600

aagaccatca cacattttca ggttatgtaa cgacttggcc tctgcttcag ctgaaatagc    660

tagaggagag actgcaaatt cagtttcatg ttacatgagg accaagggta tatcagaaga    720

attagcaacc gaatctgtca tgaatttaat cgacgagacc tggaagaaga tgaacaagga    780

aaagttggga ggttctttat tcgcaaaacc ttttgtcgaa acagccatca atttagccag    840

gcagtcacac tgtacatatc acaatggtga tgcccacacc tcacctgacg agttgaccag    900

gaaaagagtt ttgtcagtta ttactgaacc tatattacct tttgagaggt gaggaagagc    960

tggcttattg                                                           970
```

```
<210> SEQ ID NO 7
<211> LENGTH: 932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

taagtagttg accatagctc ttccatggcc accgagttgt tgtgcttgca caggcctatc     60
```

-continued

```
tctttgaccc acaagttgtt caggaaccct ttgccaaagg taattcaagc cacaccattg    120

accttaaagt tgaggtgctc agtctctacc gagaacgtct ctttcaccga gacagagact    180

gaagctagga gatcagccaa ctacgagcca aattcatggg actacgactt cttgttatca    240

tctgacaccg acgagtcaat tgaggtctac aaagacaagg caaagaaatt ggaggcagag    300

gtcaggagag aaatcaacaa cgaaaaggcc gagttcttaa ctttgttgga gttgatcgac    360

aatgtacaga gattgggatt gggttacagg ttcgagtctg acattaggag ggctttagac    420

aggtttgttt catcaggtgg atttgacggt gtcacaaaaa catcattaca tgcaactgcc    480

ttgtctttca gattattaag gcaacatgga ttcgaagtct ctcaagaggc tttctctgga    540

ttcaaggacc agaacggtaa cttcttagag aatttgaaag aggacaccaa agcaattttg    600

tcattgtacg aggcttcatt cttggcattg gaaggtgaga atatcttgga tgaagcaaga    660

gtattcgcta tctctcactt gaaggagttg tctgaagaaa aaatcggaaa agaattggca    720

gagcaagtaa atcacgcctt agaattgcct ttacacagaa ggacacagag gttagaagca    780

gtctggtcta ttgaggctta tagaaagaag gaagatgcca accaagtatt gttggagttg    840

gccattttgg actacaacat gatccagtca gtctaccaga gggacttaag agagacctct    900

aggtggtgga gaagggaaga gctggcttat tg                                  932
```

<210> SEQ ID NO 8
<211> LENGTH: 970
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
taagtagttg accatagctc ttcccttaag agagacctct aggtggtgga gaagagtagg     60

attagctact aaattgcact tcgctaagga cagattaatc gaatcatttt actgggctgt    120

cggagtcgct tttgaacctc agtactctga ttgtagaaac tctgtagcca agatgttttc    180

tttcgtcacc atcatcgacg atatctacga cgtctatggt atcttggacg aattagagtt    240

gtttaccgat gctgtcgaaa ggtgggatgt taacgcaatt aatgatttgc ctgactacat    300

gaagttgtgc tttttagcct tatacaacac catcaacgag atcgcctatg acaacttgaa    360

ggacaaggga gagaacattt tgccatactt gaccaaggct tgggctgatt tatgtaacgc    420

ctttttacaa gaggccaagt ggttatacaa caagtctaca ccaaccttcg acgattattt    480

cggaaatgcc tggaaatctt catctggacc tttgcaattg atatttgcat acttcgcagt    540

tgtccagaac atcaaaaagg aggagatcga aaacttgcag aaataccacg acatcatctc    600

aaggccatca catatcttca ggttgtgcaa cgatttggca tcagcttctg ctgaaatcgc    660

aagaggagag acagctaatt cagtctcatg ctacatgagg actaagggaa tctcagaaga    720

attggccacc gaatcagtca tgaacttgat tgacgagacc tgcaaaaaga tgaacaagga    780

gaagttggga ggatctttgt ttgcaaaacc attcgtcgag accgccataa acttggctag    840

gcagtctcac tgcacctacc acaacggtga cgcccacaca tcacctgacg agttgaccag    900

gaaaagggta ttgtctgtta ttacagaacc aatcttacct tttgagaggt gaggaagagc    960

tggcttattg                                                           970
```

<210> SEQ ID NO 9
<211> LENGTH: 5050
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 9
gtttaaacta ctattagctg aattgccact gctatcgttg ttagtggcgt tagtgcttgc 60
attcaaagac atggagggcg ttattacgcc ggagctcctc gacagcagat ctgatgactg 120
gtcaatatat ttttgcattg aggctctgtt tggaattata ttttgagatg acccatctaa 180
tgtactggta tcaccagatt tcatgtcgtt ttttaaagcg gctgcttgag tcttagcaat 240
agcgtcacca tctggtgaat cctttgaagg aaccactgac gaaggtttgg acagtgacga 300
agaggatctt tcctgctttg aattagtcgc gctgggagca gatgacgagt tggtggagct 360
gggggcagga ttgctggccg tcgtgggtcc tgaatgggtc cttggctggt ccatctctat 420
tctgaaaacg gaagaggagt agggaatatt actggctgaa aataagtctt gaatgaacgt 480
atacgcgtat atttctacca atctctcaac actgagtaat ggtagttata agaaagagac 540
cgagttaggg acagttagag gcggtggaga tattccttat ggcatgtctg gcgatgataa 600
aacttttcaa acggcagccc cgatctaaaa gagctgacac ccgggagtta tgacaattac 660
aacaacagaa ttctttctat atatgcacga acttgtaata tggaagaaat tatgacgtac 720
aaactataaa gtaaatattt tacgtaacac atggtgctgt tgtgcttctt tttcaagaga 780
ataccaatga cgtatgacta agtttaggat ttaatgcagg tgacggaccc atctttcaaa 840
cgatttatat cagtggcgtc caaattgtta ggttttgttg gttcagcagg tttcctgttg 900
tgggtcatat gactttgaac caaatggccg gctgctaggg cagcacataa ggataattca 960
cctgccaaga cggcacaggc aactattctt gctaattgac gtgcgttggt accaggagcg 1020
gtagcatgtg ggcctcttac acctaataag tccaacatgg caccttgtgg ttctagaaca 1080
gtaccaccac cgatggtacc tacttcgatg gatggcatgg atacggaaat tctcaaatca 1140
ccgtccactt ctttcatcaa tgttatacag ttggaacttt cgacattttg tgcaggatct 1200
tgtcctaatg ccaagaaaac agctgtcact aaattagctg catgtgcgtt aaatccacca 1260
acagacccag ccattgcaga tccaaccaaa ttcttagcaa tgttcaactc aaccaatgcg 1320
gaaacatcac tttttaacac ttttctgaca acatcaccag gaatagtagc ttctgcgacg 1380
acactcttac cacgaccttc gatccagttg atggcagctg gtttttgtc ggtacagtag 1440 ttaccagaaa cggagacaac ctccatatct tcccagccat actcttctac catttgcttt 1500
aatgagtatt cgacaccctt agaaatcata ttcataccca ttgcgtcacc agtagttgtt 1560
ctaaatctca tgaagagtaa atctcctgct agacaagttt gaatatgttg cagacgtgca 1620
aatcttgatg tagagttaaa agctttttta attgcgtttt gtccctcttc tgagtctaac 1680
catatcttac aggcaccaga tcttttcaaa gttgggaaac ggactactgg gcctcttgtc 1740
ataccatcct tagttaaaac agttgttgca ccaccgccag cattgattgc cttacagcca 1800
cgcatggcag aagctaccaa acaaccctct gtagttgcca ttggtatatg ataagatgta 1860
ccatcgataa ccaaggggcc tataacacca acgggcaaag gcatgtaacc tataacattt 1920
tcacaacaag cgccaaatac gcggtcgtag tcataatttt tatatggtaa acgatcagat 1980
gctaatacag gagcttctgc caaaattgaa agagccttcc tacgtaccgc aaccgctctc 2040
gtagtatcac ctaatttttt ctccaaagcg tacaaaggta acttaccgtg aataaccaag 2100
gcagcgacct ctttgttctt caattgtttt gtatttccac tacttaataa tgcttctaat 2160

-continued

```
tcttctaaag gacgtatttt cttatccaag ctttcaatat cgcgggaatc atcttcctca   2220
ctagatgatg aaggtcctga tgagctcgat tgcgcagatg ataaactttt gactttcgat   2280
ccagaaatga ctgttttatt ggttaaaact ggtgtagaag ccttttgtac aggagcagta   2340
aaagacttct tggtgacttc agtcttcacc aattggtctg cagccattat agtttttttct  2400
ccttgacgtt aaagtataga ggtatattaa caatttttttg ttgatacttt tatgacattt  2460
gaataagaag taatacaaac cgaaaatgtt gaaagtatta gttaaagtgg ttatgcagct   2520
tttgcattta tatatctgtt aatagatcaa aaatcatcgc ttcgctgatt aattacccca   2580
gaaataaggc taaaaaacta atcgcattat tatcctatgg ttgttaattt gattcgttga   2640
tttgaaggtt tgtggggcca ggttactgcc aatttttcct cttcataacc ataaaagcta   2700
gtattgtaga atctttattg ttcggagcag tgcggcgcga ggcacatctg cgtttcagga   2760
acgcgaccgg tgaagaccag gacgcacgga ggagagtctt ccgtcggagg gctgtcgccc   2820
gctcggcggc ttctaatccg tacttcaata tagcaatgag cagttaagcg tattactgaa   2880
agttccaaag agaaggtttt tttaggctaa gataatgggg ctctttacat ttccacaaca   2940
tataagtaag attagatatg gatatgtata tggtggtatt gccatgtaat atgattatta   3000
aacttctttg cgtccatcca aaaaaaaagt aagaattttt gaaaattcaa tataaatggc   3060
ttcagaaaaa gaaattagga gagagagatt cttgaacgtt ttccctaaat tagtagagga   3120
attgaacgca tcgcttttgg cttacggtat gcctaaggaa gcatgtgact ggtatgccca   3180
ctcattgaac tacaacactc caggcggtaa gctaaataga ggtttgtccg ttgtggacac   3240
gtatgctatt ctctccaaca agaccgttga acaattgggg caagaagaat acgaaaaggt   3300
tgccattcta ggttggtgca ttgagttgtt gcaggcttac ttcttggtcg ccgatgatat   3360
gatggacaag tccattacca gaagaggcca accatgttgg tacaaggttc ctgaagttgg   3420
ggaaattgcc atcaatgacg cattcatgtt agaggctgct atctacaagc ttttgaaatc   3480
tcacttcaga aacgaaaaat actacataga tatcaccgaa ttgttccatg aggtcacctt   3540
ccaaaccgaa ttgggccaat tgatggactt aatcactgca cctgaagaca aagtcgactt   3600
gagtaagttc tccctaaaga agcactcctt catagttact ttcaagactg cttactattc   3660
tttctacttg cctgtcgcat tggccatgta cgttgccggt atcacggatg aaaaggattt   3720
gaaacaagcc agagatgtct tgattccatt gggtgaatac ttccaaattc aagatgacta   3780
cttagactgc ttcggtaccc cagaacagat cggtaagatc ggtacagata tccaagataa   3840
caaatgttct tgggtaatca acaaggcatt ggaacttgct tccgcagaac aaagaaagac   3900
tttagacgaa aattacggta agaaggactc agtcgcagaa gccaaatgca aaaagatttt   3960
caatgacttg aaaattgaac agctatacca cgaatatgaa gagtctattg ccaaggattt   4020
gaaggccaaa atttctcagg tcgatgagtc tcgtggcttc aaagctgatg tcttaactgc   4080
gttcttgaac aaagtttaca agagaagcaa atagaactaa cgctaatcga taaaacatta   4140
gatttcaaac tagataagga ccatgtataa gaactatata cttccaatat aatatagtat   4200
aagctttaag atagtatctc tcgatctacc gttccacgtg actagtccaa ggattttttt   4260
taacccggga tatatgtgta ctttgcagtt atgacgccag atggcagtag tggaagatat   4320
tctttattga aaaatagctt gtcaccttac gtacaatctt gatccggagc ttttcttttt   4380
ttgccgatta agaattcggt cgaaaaaaga aaaggagagg gccaagaggg agggcattgg   4440
tgactattga gcacgtgagt atacgtgatt aagcacacaa aggcagcttg gagtatgtct   4500
gttattaatt tcacaggtag ttctggtcca ttggtgaaag tttgcggctt gcagagcaca   4560
```

gaggccgcag aatgtgctct agattccgat gctgacttgc tgggtattat atgtgtgccc 4620
aatagaaaga gaacaattga cccggttatt gcaaggaaaa tttcaagtct tgtaaaagca 4680
tataaaaata gttcaggcac tccgaaatac ttggttggcg tgtttcgtaa tcaacctaag 4740
gaggatgttt tggctctggt caatgattac ggcattgata tcgtccaact gcatggagat 4800
gagtcgtggc aagaatacca agagttcctc ggtttgccag ttattaaaag actcgtattt 4860
ccaaaagact gcaacatact actcagtgca gcttcacaga aacctcattc gtttattccc 4920
ttgtttgatt cagaagcagg tgggacaggt gaacttttgg attggaactc gatttctgac 4980
tgggttggaa ggcaagagag ccccgaaagc ttacatttta tgttagctgg tggactgacg 5040
ccgtttaaac 5050

<210> SEQ ID NO 10
<211> LENGTH: 5488
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
gtttaaactt gctaaattcg agtgaaacac aggaagacca gaaaatcctc atttcatcca 60
tattaacaat aatttcaaat gtttatttgc attatttgaa actagggaag acaagcaacg 120
aaacgttttt gaaaatttg agtattttca ataaatttgt agaggactca gatattgaaa 180
aaaagctaca gcaattaata cttgataaga agagtattga gaagggcaac ggttcatcat 240
ctcatggatc tgcacatgaa caaacaccag agtcaaacga cgttgaaatt gaggctactg 300
cgccaattga tgacaataca gacgatgata acaaaccgaa gttatctgat gtagaaaagg 360
attaaagatg ctaagagata gtgatgatat ttcataaata atgtaattct atatatgtta 420
attacctttt ttgcgaggca tatttatggt gaaggataag ttttgaccat caaagaaggt 480
taatgtggct gtggtttcag ggtccatacc cgggagttat gacaattaca acaacagaat 540
tctttctata tatgcacgaa cttgtaatat ggaagaaatt atgacgtaca aactataaag 600
taaatatttt acgtaacaca tggtgctgtt gtgcttcttt ttcaagagaa taccaatgac 660
gtatgactaa gtttaggatt taatgcaggt gacggaccca tctttcaaac gatttatatc 720
agtggcgtcc aaattgttag gttttgttgg ttcagcaggt ttcctgttgt gggtcatatg 780
actttgaacc aaatggccgg ctgctagggc agcacataag gataattcac ctgccaagac 840
ggcacaggca actattcttg ctaattgacg tgcgttggta ccaggagcgg tagcatgtgg 900
gcctcttaca cctaataagt ccaacatggc accttgtggt tctagaacag taccaccacc 960
gatggtacct acttcgatgg atggcatgga tacggaaatt ctcaaatcac cgtccacttc 1020
tttcatcaat gttatacagt tggaactttc gacattttgt gcaggatctt gtcctaatgc 1080
caagaaaaca gctgtcacta aattagctgc atgtgcgtta aatccaccaa cagacccagc 1140
cattgcagat ccaaccaaat tcttagcaat gttcaactca accaatgcgg aaacatcact 1200
ttttaacact tttctgacaa catcaccagg aatagtagct tctgcgacga cactcttacc 1260
acgaccttcg atccagttga tggcagctgg ttttttgtcg gtacagtagt taccagaaac 1320
ggagacaacc tccatatctt cccagccata ctcttctacc atttgcttta atgagtattc 1380
gacaccctta gaaatcatat tcatacccat tgcgtcacca gtagttgttc taaatctcat 1440
gaagagtaaa tctcctgcta gacaagtttg aatatgttgc agacgtgcaa atcttgatgt 1500

-continued

```
agagttaaaa gctttttttaa ttgcgttttg tccctcttct gagtctaacc atatcttaca   1560
ggcaccagat cttttcaaag ttgggaaacg gactactggg cctcttgtca taccatcctt   1620
agttaaaaca gttgttgcac caccgccagc attgattgcc ttacagccac gcatggcaga   1680
agctaccaaa caaccctctg tagttgccat tggtatatga taagatgtac catcgataac   1740
caaggggcct ataacaccaa cgggcaaagg catgtaacct ataacatttt cacaacaagc   1800
gccaaatacg cggtcgtagt cataattttt atatggtaaa cgatcagatg ctaatacagg   1860
agcttctgcc aaaattgaaa gagccttcct acgtaccgca accgctctcg tagtatcacc   1920
taattttttc tccaaagcgt acaaaggtaa cttaccgtga ataaccaagg cagcgacctc   1980
tttgttcttc aattgttttg tatttccact acttaataat gcttctaatt cttctaaagg   2040
acgtattttc ttatccaagc tttcaatatc gcgggaatca tcttcctcac tagatgatga   2100
aggtcctgat gagctcgatt gcgcagatga taaacttttg actttcgatc cagaaatgac   2160
tgttttattg gttaaaactg gtgtagaagc cttttgtaca ggagcagtaa aagacttctt   2220
ggtgacttca gtcttcacca attggtctgc agccattata gtttttttctc cttgacgtta   2280
aagtatagag gtatattaac aatttttttgt tgatactttt atgacatttg aataagaagt   2340
aatacaaacc gaaaatgttg aaagtattag ttaaagtggt tatgcagctt ttgcatttat   2400
atatctgtta atagatcaaa aatcatcgct tcgctgatta attaccccag aaataaggct   2460
aaaaaactaa tcgcattatt atcctatggt tgttaatttg attcgttgat ttgaaggttt   2520
gtggggccag gttactgcca atttttcctc ttcataacca taaaagctag tattgtagaa   2580
tctttattgt tcggagcagt gcggcgcgag gcacatctgc gtttcaggaa cgcgaccggt   2640
gaagaccagg acgcacggag gagagtcttc cgtcggaggg ctgtcgcccg ctcggcggct   2700
tctaatccgt acttcaatat agcaatgagc agttaagcgt attactgaaa gttccaaaga   2760
gaaggttttt ttaggctaag ataatggggc tctttacatt tccacaacat ataagtaaga   2820
ttagatatgg atatgtatat ggtggtattg ccatgtaata tgattattaa acttctttgc   2880
gtccatccaa aaaaaaagta agaatttttg aaaattcaat ataaatgaaa ctctcaacta   2940
aactttgttg gtgtggtatt aaaggaagac ttaggccgca aaagcaacaa caattacaca   3000
atacaaactt gcaaatgact gaactaaaaa aacaaaagac cgctgaacaa aaaaccagac   3060
ctcaaaatgt cggtattaaa ggtatccaaa tttacatccc aactcaatgt gtcaaccaat   3120
ctgagctaga gaaatttgat ggcgtttctc aaggtaaata cacaattggt ctgggccaaa   3180
ccaacatgtc ttttgtcaat gacagagaag atatctactc gatgtcccta actgttttgt   3240
ctaagttgat caagagttac aacatcgaca ccaacaaaat tggtagatta gaagtcggta   3300
ctgaaactct gattgacaag tccaagtctg tcaagtctgt cttgatgcaa ttgtttggtg   3360
aaaacactga cgtcgaaggt attgacacgc ttaatgcctg ttacggtggt accaacgcgt   3420
tgttcaactc tttgaactgg attgaatcta acgcatggga tggtagagac gccattgtag   3480
tttgcggtga tattgccatc tacgataagg gtgccgcaag accaaccggt ggtgccggta   3540
ctgttgctat gtggatcggt cctgatgctc caattgtatt tgactctgta agagcttctt   3600
acatggaaca cgcctacgat ttttacaagc cagatttcac cagcgaatat ccttacgtcg   3660
atggtcattt ttcattaact tgttacgtca aggctcttga tcaagtttac aagagttatt   3720
ccaagaaggc tatttctaaa gggttggtta gcgatcccgc tggttcggat gctttgaacg   3780
ttttgaaata tttcgactac aacgttttcc atgttccaac ctgtaaattg gtcacaaaat   3840
```

catacggtag attactatat aacgatttca gagccaatcc tcaattgttc ccagaagttg 3900
acgccgaatt agctactcgc gattatgacg aatctttaac cgataagaac attgaaaaaa 3960
cttttgttaa tgttgctaag ccattccaca aagagagagt tgcccaatct ttgattgttc 4020
caacaaacac aggtaacatg tacaccgcat ctgtttatgc cgcctttgca tctctattaa 4080
actatgttgg atctgacgac ttacaaggca agcgtgttgg tttattttct tacggttccg 4140
gtttagctgc atctctatat tcttgcaaaa ttgttggtga cgtccaacat attatcaagg 4200
aattagatat tactaacaaa ttagccaaga gaatcaccga aactccaaag gattacgaag 4260
ctgccatcga attgagagaa aatgcccatt tgaagaagaa cttcaaacct caaggttcca 4320
ttgagcattt gcaaagtggt gtttactact tgaccaacat cgatgacaaa tttagaagat 4380
cttacgatgt taaaaaataa tcttccccca tcgattgcat cttgctgaac ccccttcata 4440
aatgctttat ttttttggca gcctgctttt tttagctctc atttaataga gtagtttttt 4500
aatctatata ctaggaaaac tctttattta ataacaatga tatatatata cccgggaagc 4560
ttttcaattc atcttttttt tttttgttct ttttttttgat tccggtttct ttgaaatttt 4620
tttgattcgg taatctccga gcagaaggaa gaacgaagga aggagcacag acttagattg 4680
gtatatatac gcatatgtgg tgttgaagaa acatgaaatt gcccagtatt cttaacccaa 4740
ctgcacagaa caaaaacctg caggaaacga agataaatca tgtcgaaagc tacatataag 4800
gaacgtgctg ctactcatcc tagtcctgtt gctgccaagc tatttaatat catgcacgaa 4860
aagcaaacaa acttgtgtgc ttcattggat gttcgtacca ccaaggaatt actggagtta 4920
gttgaagcat taggtcccaa aatttgttta ctaaaaacac atgtggatat cttgactgat 4980
ttttccatgg agggcacagt taagccgcta aaggcattat ccgccaagta caatttttta 5040
ctcttcgaag acagaaaatt tgctgacatt ggtaatacag tcaaattgca gtactctgcg 5100
ggtgtataca gaatagcaga atgggcagac attacgaatg cacacggtgt ggtgggccca 5160
ggtattgtta gcggtttgaa gcaggcggcg gaagaagtaa caaaggaacc tagaggcctt 5220
ttgatgttag cagaattgtc atgcaagggc tccctagcta ctggagaata tactaagggt 5280
actgttgaca ttgcgaagag cgacaaagat tttgttatcg gctttattgc tcaaagagac 5340
atgggtggaa gagatgaagg ttacgattgg ttgattatga cacccggtgt gggtttagat 5400
gacaagggag acgcattggg tcaacagtat agaaccgtgg atgatgtggt ctctacagga 5460
tctgacatta ttattgttgg gtttaaac 5488

<210> SEQ ID NO 11
<211> LENGTH: 4933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
gtttaaacta ctcagtatat taagtttcga attgaagggc gaactcttat tcgaagtcgg 60
agtcaccaca acacttccgc ccatactctc cgaatcctcg tttcctaaag taagtttact 120
tccacttgta ggcctattat taatgatatc tgaataatcc tctattaggg ttggatcatt 180
cagtagcgcg tgcgattgaa aggagtccat gcccgacgtc gacgtgatta gcgaaggcgc 240
gtaaccattg tcatgtctag cagctataga actaacctcc ttgacaccac ttgcggaagt 300
ctcatcaaca tgctcttcct tattactcat tctcttacca agcagagaat gttatctaaa 360

-continued

```
aactacgtgt atttcacctc tttctcgact tgaacacgtc caactcctta agtactacca    420
cagccaggaa agaatggatc cagttctaca cgatagcaaa gcagaaaaca caaccagcgt    480
acccctgtag aagcttcttt gtttacagca cttgatccat gtagccatac tcgaaatttc    540
aactcatctg aaacttttcc tgaaggttga aaaagaatgc cataagggtc acccgaagct    600
tattcacgcc cgggagttat gacaattaca acaacagaat tctttctata tatgcacgaa    660
cttgtaatat ggaagaaatt atgacgtaca aactataaag taaatatttt acgtaacaca    720
tggtgctgtt gtgcttcttt ttcaagagaa taccaatgac gtatgactaa gtttaggatt    780
taatgcaggt gacggaccca tctttcaaac gatttatatc agtggcgtcc aaattgttag    840
gttttgttgg ttcagcaggt ttcctgttgt gggtcatatg actttgaacc aaatggccgg    900
ctgctagggc agcacataag gataattcac ctgccaagac ggcacaggca actattcttg    960
ctaattgacg tgcgttggta ccaggagcgg tagcatgtgg gcctcttaca cctaataagt   1020
ccaacatggc accttgtggt tctagaacag taccaccacc gatggtacct acttcgatgg   1080
atggcatgga tacggaaatt ctcaaatcac cgtccacttc tttcatcaat gttatacagt   1140
tggaactttc gacattttgt gcaggatctt gtcctaatgc caagaaaaca gctgtcacta   1200
aattagctgc atgtgcgtta aatccaccaa cagacccagc cattgcagat ccaaccaaat   1260
tcttagcaat gttcaactca accaatgcgg aaacatcact ttttaacact tttctgacaa   1320
catcaccagg aatagtagct tctgcgacga cactcttacc acgaccttcg atccagttga   1380
tggcagctgg tttttgtcg gtacagtagt taccagaaac ggagacaacc tccatatctt    1440
cccagccata ctcttctacc atttgcttta atgagtattc gacaccctta gaaatcatat   1500
tcatacccat tgcgtcacca gtagttgttc taaatctcat gaagagtaaa tctcctgcta   1560
gacaagtttg aatatgttgc agacgtgcaa atcttgatgt agagttaaaa gctttttttaa  1620
ttgcgttttg tccctcttct gagtctaacc atatcttaca ggcaccagat cttttcaaag   1680
ttgggaaacg gactactggg cctcttgtca taccatcctt agttaaaaca gttgttgcac   1740
caccgccagc attgattgcc ttacagccac gcatggcaga agctaccaaa caaccctctg   1800
tagttgccat tggtatatga taagatgtac catcgataac caaggggcct ataacaccaa   1860
cgggcaaagg catgtaacct ataacatttt cacaacaagc gccaaatacg cggtcgtagt   1920
cataattttt atatggtaaa cgatcagatg ctaatacagg agcttctgcc aaaattgaaa   1980
gagccttcct acgtaccgca accgctctcg tagtatcacc taatttttttc tccaaagcgt  2040
acaaaggtaa cttaccgtga ataaccaagg cagcgacctc tttgttcttc aattgttttg   2100
tatttccact acttaataat gcttctaatt cttctaaagg acgtattttc ttatccaagc   2160
tttcaatatc gcgggaatca tcttcctcac tagatgatga aggtcctgat gagctcgatt   2220
gcgcagatga taaacttttg actttcgatc cagaaatgac tgttttattg gttaaaactg   2280
gtgtagaagc cttttgtaca ggagcagtaa aagacttctt ggtgacttca gttttcacca   2340
attggtctgc agccattata gttttttctc cttgacgtta aagtatagag gtatattaac   2400
aattttttgt tgatactttt atgacatttg aataagaagt aatacaaacc gaaaatgttg   2460
aaagtattag ttaaagtggt tatgcagctt ttgcatttat atatctgtta atagatcaaa   2520
aatcatcgct tcgctgatta attaccccag aaataaggct aaaaaactaa tcgcattatt   2580
atcctatggt tgttaatttg attcgttgat ttgaaggttt gtggggccag gttactgcca   2640
atttttcctc ttcataacca taaaagctag tattgtagaa tctttattgt tcggagcagt   2700
gcggcgcgag gcacatctgc gtttcaggaa cgcgaccggt gaagaccagg acgcacggag   2760
```

-continued

```
gagagtcttc cgtcggaggg ctgtcgcccg ctcggcggct tctaatccgt acttcaatat   2820
agcaatgagc agttaagcgt attactgaaa gttccaaaga gaaggttttt ttaggctaag   2880
ataatggggc tctttacatt tccacaacat ataagtaaga ttagatatgg atatgtatat   2940
ggtggtattg ccatgtaata tgattattaa acttctttgc gtccatccaa aaaaaaagta   3000
agaatttttg aaaattcaat ataaatgact gccgacaaca atagtatgcc ccatggtgca   3060
gtatctagtt acgccaaatt agtgcaaaac caaacacctg aagacatttt ggaagagttt   3120
cctgaaatta ttccattaca acaaagacct aatacccgat ctagtgagac gtcaaatgac   3180
gaaagcggag aaacatgttt ttctggtcat gatgaggagc aaattaagtt aatgaatgaa   3240
aattgtattg ttttggattg ggacgataat gctattggtg ccggtaccaa gaaagtttgt   3300
catttaatgg aaaatattga aaagggttta ctacatcgtg cattctccgt ctttattttc   3360
aatgaacaag gtgaattact tttacaacaa agagccactg aaaaaataac tttccctgat   3420
ctttggacta acacatgctg ctctcatcca ctatgtattg atgacgaatt aggtttgaag   3480
ggtaagctag acgataagat taagggcgct attactgcgg cggtgagaaa actagatcat   3540
gaattaggta ttccagaaga tgaaactaag acaaggggta agtttcactt tttaaacaga   3600
atccattaca tggcaccaag caatgaacca tggggtgaac atgaaattga ttacatccta   3660
ttttataaga tcaacgctaa agaaaacttg actgtcaacc caaacgtcaa tgaagttaga   3720
gacttcaaat gggtttcacc aaatgatttg aaaactatgt ttgctgaccc aagttacaag   3780
tttacgcctt ggtttaagat tatttgcgag aattacttat tcaactggtg ggagcaatta   3840
gatgaccttt ctgaagtgga aaatgacagg caaattcata gaatgctata acaacgcgtc   3900
aataatatag gctacataaa aatcataata actttgttat catagcaaaa tgtgatataa   3960
aacgtttcat ttcacctgaa aaatagtaaa aataggcgac aaaaatcctt agtaatatgt   4020
aaactttatt ttctttattt acccgggagt cagtctgact cttgcgagag atgaggatgt   4080
aataatacta atctcgaaga tgccatctaa tacatataga catacatata tatatatata   4140
cattctatat attcttaccc agattctttg aggtaagacg gttgggtttt atcttttgca   4200
gttggtacta ttaagaacaa tcgaatcata agcattgctt acaaagaata cacatacgaa   4260
atattaacga taatgtcaat tacgaagact gaactggacg gtatattgcc attggtggcc   4320
agaggtaaag ttagagacat atatgaggta gacgctggta cgttgctgtt tgttgctacg   4380
gatcgtatct ctgcatatga cgttattatg gaaaacagca ttcctgaaaa ggggatccta   4440
ttgaccaaac tgtcagagtt ctggttcaag ttcctgtcca acgatgttcg taatcatttg   4500
gtcgacatcg ccccaggtaa gactattttc gattatctac ctgcaaaatt gagcgaacca   4560
aagtacaaaa cgcaactaga agaccgctct ctattggttc acaaacataa actaattcca   4620
ttggaagtaa ttgtcagagg ctacatcacc ggatctgctt ggaaagagta cgtaaaaaca   4680
ggtactgtgc atggtttgaa acaacctcaa ggacttaaag aatctcaaga gttcccagaa   4740
ccaatcttca ccccatcgac caaggctgaa caaggtgaac atgacgaaaa catctctcct   4800
gcccaggccg ctgagctggt gggtgaagat ttgtcacgta gagtggcaga actggctgta   4860
aaactgtact ccaagtgcaa agattatgct aaggagaagg gcatcatcat cgcagacact   4920
aaattgttta aac                                                      4933
```

<210> SEQ ID NO 12
<211> LENGTH: 6408
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 12
gtttaaacta ttgtgagggt cagttatttc atccagatat aacccgagag gaaacttctt 60
agcgtctgtt ttcgtaccat aaggcagttc atgaggtata ttttcgttat tgaagcccag 120
ctcgtgaatg cttaatgctg ctgaactggt gtccatgtcg cctaggtacg caatctccac 180
aggctgcaaa ggttttgtct caagagcaat gttattgtgc accccgtaat tggtcaacaa 240
gtttaatctg tgcttgtcca ccagctctgt cgtaaccttc agttcatcga ctatctgaag 300
aaatttacta ggaatagtgc catggtacag caaccgagaa tggcaatttc tactcgggtt 360
cagcaacgct gcataaacgc tgttggtgcc gtagacatat tcgaagatag gattatcatt 420
cataagtttc agagcaatgt ccttattctg gaacttggat ttatggctct tttggtttaa 480
tttcgcctga ttcttgatct cctttagctt ctcgacgtgg gcctttttct tgccatatgg 540
atccgctgca cggtcctgtt ccctagcatg tacgtgagcg tatttccttt taaaccacga 600
cgctttgtct tcattcaacg tttcccattg tttttttcta ctattgcttt gctgtgggaa 660
aaacttatcg aaagatgacg actttttctt aattctcgtt ttaagagctt ggtgagcgct 720
aggagtcact gccaggtatc gtttgaacac ggcattagtc agggaagtca taacacagtc 780
ctttcccgca attttctttt tctattactc ttggcctcct ctagtacact ctatattttt 840
ttatgcctcg gtaatgattt tcattttttt tttttccacc tagcggatga ctcttttttt 900
ttcttagcga ttggcattat cacataatga attatacatt atataaagta atgtgatttc 960
ttcgaagaat atactaaagt ttagcttgcc tcgtccccgc cgggtcaccc ggccagcgac 1020
atggaggccc agaataccct ccttgacagt cttgacgtgc gcagctcagg ggcatgatgt 1080
gactgtcgcc cgtacattta gcccatacat ccccatgtat aatcatttgc atccatacat 1140
tttgatggcc gcacggcgcg aagcaaaaat tacggctcct cgctgcagac ctgcgagcag 1200
ggaaacgctc ccctcacaga cgcgttgaat tgtccccacg ccgcgcccct gtagagaaat 1260
ataaaaggtt aggatttgcc actgaggttc ttctttcata tacttccttt taaaatcttg 1320
ctaggataca gttctcacat cacatccgaa cataaacaac catggcagaa ccagcccaaa 1380
aaaagcaaaa acaaactgtt caggagcgca aggcgtttat ctcccgtatc actaatgaaa 1440
ctaaaattca aatcgctatt tcgctgaatg gtggttatat tcaaataaaa gattcgattc 1500
ttcctgcaaa gaaggatgac gatgtagctt cccaagctac tcagtcacag gtcatcgata 1560
ttcacacagg tgttggcttt ttggatcata tgatccatgc gttggcaaaa cactctggtt 1620
ggtctcttat tgttgaatgt attggtgacc tgcacattga cgatcaccat actaccgaag 1680
attgcggtat cgcattaggg caagcgttca aagaagcaat gggtgctgtc cgtggtgtaa 1740
aaagattcgg tactgggttc gcaccattgg atgaggcgct atcacgtgcc gtagtcgatt 1800
tatctagtag accatttgct gtaatcgacc ttggattgaa gagagagatg attggtgatt 1860
tatccactga aatgattcca cactttttgg aaagtttcgc ggaggcggcc agaattactt 1920
tgcatgttga ttgtctgaga ggtttcaacg atcaccacag aagtgagagt gcgttcaagg 1980
ctttggctgt tgccataaga gaagctattt ctagcaatgg caccaatgac gttccctcaa 2040
ccaaaggtgt tttgatgtga agtactgaca ataaaaagat tcttgttttc aagaacttgt 2100
catttgtata gtttttttat attgtagttg ttctatttta atcaaatgtt agcgtgattt 2160
atattttttt tcgcctcgac atcatctgcc cagatgcgaa gttaagtgcg cagaaagtaa 2220
tatcatgcgt caatcgtatg tgaatgctgg tcgctatact gctgtcgatt cgatactaac 2280
gccgccatcc acccgggatg gtctgcttaa atttcattct gtcttcgaaa gctgaattga 2340
tactacgaaa aatttttttt tgtttctctt tctatcttta ttacataaaa cttcatacac 2400
agttaagatt aaaaacaact aataaataat gcctatcgca aattagctta tgaagtccat 2460
ggtaaattcg tgtttcctgg caataataga tcgtcaattt gttgctttgt ggtagtttta 2520
ttttcaaata attggaatac tagggatttg attttaagat ctttattcaa atttttttgcg 2580 cttaacaaac agcagccagt cccacccaag tctgtttcaa atgtctcgta actaaaatca 2640
tcttgcaatt tctttttgaa actgtcaatt tgctcttgag taatgtctct tcgtaacaaa 2700
gtcaaagagc aaccgccgcc accagcaccg gtaagttttg tggagccaat tctcaaatca 2760
tcgctcagat ttttaataag ttctaatcca ggatgagaaa caccgattga gacaagcagt 2820
ccatgattta ttcttatcaa ttccaatagt tgttcataca gttcattatt agtttctaca 2880
gcctcgtcat cggtgccttt acatttactt aacttagtca tgatctctaa gccttgtagg 2940
gcacattcac ccatggcatc tagaattggc ttcataactt caggaaattt ctcggtgacc 3000
aacacacgaa cgcgagcaac aagatctttt gtagaccttg gaattctagt ataggttagg 3060
atcattggaa tggctgggaa atcatctaag aacttaaaat tgtttgtgtt tattgttcca 3120
ttatgtgagt ctttttcaaa tagcagggca ttaccataag tggccacagc gttatctatt 3180
cctgaagggg taccgtgaat acacttttca cctatgaagg cccattgatt cactatatgc 3240
ttatcgtttt ctgacagctt ttccaagtca ttagatccta ttaacccccc caagtaggcc 3300
atagctaagg ccagtgatac agaaatagag gcgcttgagc ccaacccagc accgatgggt 3360
aaagtagact ttaaagaaaa cttaatattc ttggcatggg ggcataggca aacaaacata 3420
tacaggaaac aaaacgctgc atggtagtgg aaggattcgg atagttgagc taacaacgga 3480
tccaaaagac taacgagttc ctgagacaag ccatcggtgg cttgttgagc cttggccaat 3540
ttttgggagt ttacttgatc ctcggtgatg gcattgaaat cattgatgga ccacttatga 3600
ttaaagctaa tgtccgggaa gtccaattca atagtatctg gtgcagatga ctcgcttatt 3660
agcaggtagg ttctcaacgc agacacacta gcagcgacgg caggcttgtt gtacacagca 3720
gagtgttcac caaaaataat aacctttccc ggtgcagaag ttaagaacgg taatgacatt 3780
atagtttttt ctccttgacg ttaaagtata gaggtatatt aacaattttt tgttgatact 3840
tttatgacat ttgaataaga agtaatacaa accgaaaatg ttgaaagtat tagttaaagt 3900
ggttatgcag cttttgcatt tatatatctg ttaatagatc aaaaatcatc gcttcgctga 3960
ttaattaccc cagaaataag gctaaaaaac taatcgcatt attatcctat ggttgttaat 4020
ttgattcgtt gatttgaagg tttgtggggc caggttactg ccaatttttc ctcttcataa 4080
ccataaaagc tagtattgta gaatctttat tgttcggagc agtgcggcgc gaggcacatc 4140
tgcgtttcag gaacgcgacc ggtgaagacc aggacgcacg gaggagagtc ttccgtcgga 4200
gggctgtcgc ccgctcggcg gcttctaatc cgtacttcaa tatagcaatg agcagttaag 4260
cgtattactg aaagttccaa agagaaggtt tttttaggct aagataatgg ggctctttac 4320
atttccacaa catataagta agattagata tggatatgta tatggtggta ttgccatgta 4380
atatgattat taaacttctt tgcgtccatc caaaaaaaaa gtaagaattt ttgaaaattc 4440
aatataaatg tctcagaacg tttacattgt atcgactgcc agaaccccaa ttggttcatt 4500
ccagggttct ctatcctcca agacagcagt ggaattgggt gctgttgctt taaaaggcgc 4560

```
cttggctaag gttccagaat tggatgcatc caaggatttt gacgaaatta tttttggtaa   4620
cgttctttct gccaatttgg gccaagctcc ggccagacaa gttgctttgg ctgccggttt   4680
gagtaatcat atcgttgcaa gcacagttaa caaggtctgt gcatccgcta tgaaggcaat   4740
cattttgggt gctcaatcca tcaaatgtgg taatgctgat gttgtcgtag ctggtggttg   4800
tgaatctatg actaacgcac catactacat gccagcagcc cgtgcgggtg ccaaatttgg   4860
ccaaactgtt cttgttgatg gtgtcgaaag agatgggttg aacgatgcgt acgatggtct   4920
agccatgggt gtacacgcag aaaagtgtgc ccgtgattgg gatattacta gagaacaaca   4980
agacaatttt gccatcgaat cctaccaaaa atctcaaaaa tctcaaaagg aaggtaaatt   5040
cgacaatgaa attgtacctg ttaccattaa gggatttaga ggtaagcctg atactcaagt   5100
cacgaaggac gaggaacctg ctagattaca cgttgaaaaa ttgagatctg caaggactgt   5160
tttccaaaaa gaaaacggta ctgttactgc cgctaacgct tctccaatca acgatggtgc   5220
tgcagccgtc atcttggttt ccgaaaaagt tttgaaggaa aagaatttga agcctttggc   5280
tattatcaaa ggttggggtg aggccgctca tcaaccagct gattttacat gggctccatc   5340
tcttgcagtt ccaaaggctt tgaaacatgc tggcatcgaa gacatcaatt ctgttgatta   5400
ctttgaattc aatgaagcct tttcggttgt cggtttggtg aacactaaga ttttgaagct   5460
agacccatct aaggttaatg tatatggtgg tgctgttgct ctaggtcacc cattgggttg   5520
ttctggtgct agagtggttg ttacactgct atccatctta cagcaagaag gaggtaagat   5580
cggtgttgcc gccatttgta atggtggtgg tggtgcttcc tctattgtca ttgaaaagat   5640
atgattacgt tctgcgattt tctcatgatc tttttcataa aatacataaa tatataaatg   5700
gctttatgta taacaggcat aatttaaagt tttatttgcg attcatcgtt tttcaggtac   5760
tcaaacgctg aggtgtgcct tttgacttac ttttcccggg agaggctagc agaattaccc   5820
tccacgttga ttgtctgcga ggcaagaatg atcatcaccg tagtgagagt gcgttcaagg   5880
ctcttgcggt tgccataaga gaagccacct cgcccaatgg taccaacgat gttccctcca   5940
ccaaaggtgt tcttatgtag tgacaccgat tatttaaagc tgcagcatac gatatatata   6000
catgtgtata tatgtatacc tatgaatgtc agtaagtatg tatacgaaca gtatgatact   6060
gaagatgaca aggtaatgca tcattctata cgtgtcattc tgaacgaggc gcgctttcct   6120
tttttctttt tgctttttct tttttttct cttgaactcg agaaaaaaaa tataaaagag   6180
atggaggaac gggaaaaagt tagttgtggt gataggtggc aagtggtatt ccgtaagaac   6240
aacaagaaaa gcatttcata ttatggctga actgagcgaa caagtgcaaa atttaagcat   6300
caacgacaac aacgagaatg gttatgttcc tcctcactta agaggaaaac caagaagtgc   6360
cagaaataac agtagcaact acaataacaa caacggcggc gtttaaac                6408
```

<210> SEQ ID NO 13
<211> LENGTH: 6087
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
gtttaaactt ttccaatagg tggttagcaa tcgtcttact ttctaacttt tcttaccttt     60
tacatttcag caatatatat atatatattt caaggatata ccattctaat gtctgcccct    120
aagaagatcg tcgttttgcc aggtgaccac gttggtcaag aaatcacagc cgaagccatt    180
```

-continued

```
aaggttctta aagctatttc tgatgttcgt tccaatgtca agttcgattt cgaaaatcat    240
ttaattggtg gtgctgctat cgatgctaca ggtgttccac ttccagatga ggcgctggaa    300
gcctccaaga aggctgatgc cgttttgtta ggtgctgtgg gtggtcctaa atggggtacc    360
ggtagtgtta gacctgaaca aggtttacta aaaatccgta aagaacttca attgtacgcc    420
aacttaagac catgtaactt tgcatccgac tctcttttag acttatctcc aatcaagcca    480
caatttgcta aaggtactga cttcgttgtt gtcagagaat tagtgggagg tatttacttt    540
ggtaagagaa aggaagacgt ttagcttgcc tcgtccccgc cgggtcaccc ggccagcgac    600
atggaggccc agaataccct ccttgacagt cttgacgtgc gcagctcagg ggcatgatgt    660
gactgtcgcc cgtacattta gcccatacat ccccatgtat aatcatttgc atccatacat    720
tttgatggcc gcacggcgcg aagcaaaaat tacggctcct cgctgcagac ctgcgagcag    780
ggaaacgctc ccctcacaga cgcgttgaat tgtccccacg ccgcgcccct gtagagaaat    840
ataaaaggtt aggatttgcc actgaggttc ttctttcata tacttccttt taaaatcttg    900
ctaggataca gttctcacat cacatccgaa cataaacaac catggcagaa ccagcccaaa    960
aaaagcaaaa acaaactgtt caggagcgca aggcgtttat ctcccgtatc actaatgaaa   1020
ctaaaattca aatcgctatt tcgctgaatg gtggttatat tcaaataaaa gattcgattc   1080
ttcctgcaaa gaaggatgac gatgtagctt cccaagctac tcagtcacag gtcatcgata   1140
ttcacacagg tgttggcttt ttggatcata tgatccatgc gttggcaaaa cactctggtt   1200
ggtctcttat tgttgaatgt attggtgacc tgcacattga cgatcaccat actaccgaag   1260
attgcggtat cgcattaggg caagcgttca aagaagcaat gggtgctgtc cgtggtgtaa   1320
aaagattcgg tactgggttc gcaccattgg atgaggcgct atcacgtgcc gtagtcgatt   1380
tatctagtag accatttgct gtaatcgacc ttggattgaa gagagagatg attggtgatt   1440
tatccactga aatgattcca cactttttgg aaagtttcgc ggaggcggcc agaattactt   1500
tgcatgttga ttgtctgaga ggtttcaacg atcaccacag aagtgagagt gcgttcaagg   1560
ctttggctgt tgccataaga gaagctattt ctagcaatgg caccaatgac gttccctcaa   1620
ccaaaggtgt tttgatgtga agtactgaca ataaaaagat tcttgttttc aagaacttgt   1680
catttgtata gtttttttat attgtagttg ttctatttta atcaaatgtt agcgtgattt   1740
atattttttt tcgcctcgac atcatctgcc cagatgcgaa gttaagtgcg cagaaagtaa   1800
tatcatgcgt caatcgtatg tgaatgctgg tcgctatact gctgtcgatt cgatactaac   1860
gccgccatcc acccgggttt ctcattcaag tggtaactgc tgttaaaatt aagatattta   1920
taaattgaag cttggtcgtt ccgaccaata ccgtagggaa acgtaaatta gctattgtaa   1980
aaaaaggaaa agaaaagaaa agaaaaatgt tacatatcga attgatctta ttcctttggt   2040
agaccagtct ttgcgtcaat caaagattcg tttgtttctt gtgggcctga accgacttga   2100
gttaaaatca ctctggcaac atccttttgc aactcaagat ccaattcacg tgcagtaaag   2160
ttagatgatt caaattgatg gttgaaagcc tcaagctgct cagtagtaaa tttcttgtcc   2220
catccaggaa cagagccaaa caatttatag ataaatgcaa agagtttcga ctcattttca   2280
gctaagtagt acaacacagc atttggacct gcatcaaacg tgtatgcaac gattgtttct   2340
ccgtaaaact gattaatggt gtggcaccaa ctgatgatac gcttggaagt gtcattcatg   2400
tagaatattg gagggaaaga gtccaaacat gtggcatgga aagagttgga atccatcatt   2460
gtttcctttg caaaggtggc gaaatctttt tcaacaatgg ctttacgcat gacttcaaat   2520
```

```
ctctttggta cgacatgttc aattctttct ttaaatagtt cggaggttgc cacggtcaat   2580
tgcataccct gagtggaact cacatccttt ttaatatcgc tgacaactag gacacaagct   2640
ttcatctgag gccagtcaga gctgtctgcg atttgtactg ccatggaatc atgaccatct   2700
tcagcttttc ccatttccca ggccacgtat ccgccaaaca acgatctaca agctgaacca   2760
gacccctttc ttgctattct agatatttct gaagttgact gtggtaattg gtataactta   2820
gcaattgcag agaccaatgc agcaaagcca gcagcggagg aagctaaacc agctgctgta   2880
ggaaagttat tttcggagac aatgtggagt ttccattgag ataatgtggg caatgaggcg   2940
tccttcgatt ccatttcctt tcttaattgg cgtaggtcgc gcagacaatt ttgagttctt   3000
tcattgtcga tgctgtgtgg ttctccattt aaccacaaag tgtcgcgttc aaactcaggt   3060
gcagtagccg cagaggtcaa cgttctgagg tcatcttgcg ataaagtcac tgatatggac   3120
gaattggtgg gcagattcaa cttcgtgtcc cttttccccc aatacttaag ggttgcgatg   3180
ttgacgggtg cggtaacgga tgctgtgtaa acggtcatta tagtttttc tccttgacgt    3240
taaagtatag aggtatatta acaatttttt gttgatactt ttatgacatt tgaataagaa   3300
gtaatacaaa ccgaaaatgt tgaaagtatt agttaaagtg gttatgcagc ttttgcattt   3360
atatatctgt taatagatca aaaatcatcg cttcgctgat taattacccc agaaataagg   3420
ctaaaaaact aatcgcatta ttatcctatg gttgttaatt tgattcgttg atttgaaggt   3480
ttgtggggcc aggttactgc caatttttcc tcttcataac cataaaagct agtattgtag   3540
aatctttatt gttcggagca gtgcggcgcg aggcacatct gcgtttcagg aacgcgaccg   3600
gtgaagacca ggacgcacgg aggagagtct tccgtcggag ggctgtcgcc cgctcggcgg   3660
cttctaatcc gtacttcaat atagcaatga gcagttaagc gtattactga aagttccaaa   3720
gagaaggttt ttttaggcta agataatggg gctctttaca tttccacaac atataagtaa   3780
gattagatat ggatatgtat atggtggtat tgccatgtaa tatgattatt aaacttcttt   3840
gcgtccatcc aaaaaaaaag taagaatttt tgaaaattca atataaatgt cagagttgag   3900
agccttcagt gccccaggga aagcgttact agctggtgga tatttagttt tagatccgaa   3960
atatgaagca tttgtagtcg gattatcggc aagaatgcat gctgtagccc atccttacgg   4020
ttcattgcaa gagtctgata agtttgaagt gcgtgtgaaa agtaaacaat ttaaagatgg   4080
ggagtggctg taccatataa gtcctaaaac tggcttcatt cctgtttcga taggcggatc   4140
taagaaccct ttcattgaaa aagttatcgc taacgtattt agctacttta agcctaacat   4200
ggacgactac tgcaatagaa acttgttcgt tattgatatt ttctctgatg atgcctacca   4260
ttctcaggag gacagcgtta ccgaacatcg tggcaacaga agattgagtt ttcattcgca   4320
cagaattgaa gaagttccca aaacagggct gggctcctcg gcaggtttag tcacagtttt   4380
aactacagct ttggcctcct tttttgtatc ggacctggaa aataatgtag acaaatatag   4440
agaagttatt cataatttat cacaagttgc tcattgtcaa gctcagggta aaattggaag   4500
cgggtttgat gtagcggcgg cagcatatgg atctatcaga tatagaagat tcccacccgc   4560
attaatctct aatttgccag atattggaag tgctacttac ggcagtaaac tggcgcattt   4620
ggttaatgaa gaagactgga atataacgat taaaagtaac catttacctt cgggattaac   4680
tttatggatg ggcgatatta agaatggttc agaaacagta aaactggtcc agaaggtaaa   4740
aaattggtat gattcgcata tgccggaaag cttgaaaata tatacagaac tcgatcatgc   4800
aaattctaga tttatggatg gactatctaa actagatcgc ttacacgaga ctcatgacga   4860
ttacagcgat cagatatttg agtctcttga gaggaatgac tgtacctgtc aaaagtatcc   4920
```

-continued

```
tgagatcaca gaagttagag atgcagttgc cacaattaga cgttccttta gaaaaataac   4980

taaagaatct ggtgccgata tcgaacctcc cgtacaaact agcttattgg atgattgcca   5040

gaccttaaaa ggagttctta cttgcttaat acctggtgct ggtggttatg acgccattgc   5100

agtgattgct aagcaagatg ttgatcttag ggctcaaacc gctgatgaca aaagattttc   5160

taaggttcaa tggctggatg taactcaggc tgactggggt gttaggaaag aaaaagatcc   5220

ggaaacttat cttgataaat aacttaaggt agataatagt ggtccatgtg acatctttat   5280

aaatgtgaag tttgaagtga ccgcgcttaa catctaacca ttcatcttcc gatagtactt   5340

gaaattgttc ctttcggcgg catgataaaa ttcttttaat gggtacaagc tacccgggcc   5400

cgggaaagat tctctttttt tatgatattt gtacataaac tttataaatg aaattcataa   5460

tagaaacgac acgaaattac aaaatggaat atgttcatag ggtagacgaa actatatacg   5520

caatctacat acatttatca agaaggagaa aaaggaggat gtaaaggaat acaggtaagc   5580

aaattgatac taatggctca acgtgataag gaaaaagaat tgcactttaa cattaatatt   5640

gacaaggagg agggcaccac acaaaaagtt aggtgtaaca gaaaatcatg aaactatgat   5700

tcctaattta tatattggag gattttctct aaaaaaaaaa aaatacaaca aataaaaaac   5760

actcaatgac ctgaccattt gatggagttt aagtcaatac cttcttgaac catttcccat   5820

aatggtgaaa gttccctcaa gaattttact ctgtcagaaa cggccttaac gacgtagtcg   5880

acctcctctt cagtactaaa tctaccaata ccaaatctga tggaagaatg ggctaatgca   5940

tcatccttac ccagcgcatg taaaacataa gaaggttcta gggaagcaga tgtacaggct   6000

gaacccgagg ataatgcgat atcccttagt gccatcaata aagattctcc ttccacgtag   6060

gcgaaagaaa cgttaacacg tttaaac                                       6087
```

<210> SEQ ID NO 14
<211> LENGTH: 2733
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14

```
gtaaaacgac ggccagtatt aaccctcact aaagggaact cgaggctctt caaaggcgcg     60

ccacggtcgt gcggattggc agactccata tgctatgcgg catcagagca gattgtactg    120

agagtgcacc atatgcggtg tgaaataccg cacagatgcg taaggagaaa ataccgcatc    180

aggcgccatt cgccattcag gctgcgcaac tgttgggaag ggcgatcggt gcgggcctct    240

tcgctattac gccagctggc gaaaggggga tgtgctgcaa ggcgattaag ttgggtaacg    300

ccagggtttt cccagtcacg acgttgtaaa acgacggcca gtgaattcga gctcggtacc    360

cggggatcct ctagcgtcga cctgcaggca tgcaagcttg gcgtaatcat ggtcatagct    420

gtttcctgtg tgaaattgtt atccgctcac aattccacac aacatacgag ccggaagcat    480

aaagtgtaaa gcctggggtg cctaatgagt gagctaactc acattaattg cgttgcgcgc    540

tagcgagtca tccaagcccc tcagcccccc tagcgtcgtg aagagcgagc tcccgctgag    600

caataactag cgtcatagct gtttcctggg tcgttcggct gcggcgagcg gtatcagctc    660

actcaaaggc ggtaatacgg ttatccacag aatcagggga taacgcagga aagaacatgt    720

gagcaaaagg ccagcaaaag gccaggaacc gtaaaaaggc cgcgttgctg gcgtttttcc    780

ataggctccg cccccctgac gagcatcaca aaaatcgacg ctcaagtcag aggtggcgaa    840
```

acccgacagg actataaaga taccaggcgt ttccccctgg aagctccctc gtgcgctctc 900
ctgttccgac cctgccgctt acccgatacc tgtccgcctt tctcccttcg ggaagcgtgg 960
cgctttctca tagctcacgc tgtaggtatc tcagttcggt gtaggtcgtt cgctccaagc 1020
tgggctgtgt gcacgaaccc cccgttcagc ccgaccgctg cgccttatcc ggtaactatc 1080
gtcttgattc caacccggta agacacgact tatcgccact ggcagcagcc actggtaaca 1140
ggattagcag agcgaggtat gtaggcggtg ctacagagtt cttgaagtgg tggcctaact 1200
acggctacac tagaagaaca gtatttggta tctgcgctct gctgaagcca gttaccttcg 1260
gaaaaagagt tggtagctct tgatccggca aacaaaccac cgctggtagc ggtggttttt 1320
ttgtttgcaa gcagcagatt acgcgcagaa aaaaaggatc tcaagaagat cctttgatct 1380
tttctacggg gtctgacgct cagtggaacg aaaactcacg ttaagggatt ttggtcatga 1440
gattatcaaa aaggatcttc acctagatcc ttttaaatta aaaatgaagt tttaaatcaa 1500
tctaaagtat atatgagtaa cttggtcgca tgcttaccaa tgcttaatca gtgaggcacc 1560
tatctcagcg atctgtctat ttcgttcatc catagttgcc tgactgcccg tcgtgtagat 1620
aactacgata cgggagggct taccatctgg ccccagtgct gcaatgatac cgcgagaccc 1680
acgctcaccg gctccagatt tatcagcaat aaaccagcca gccggaaggg ccgagcgcag 1740
aagtggtcct gcaactttat ccgcctccat ccagtctatt aattgttgcc gggaagctag 1800
agtaagtagt tcgccagtta atagtttgcg caacgttgtt gccattgcta caggcatcgt 1860
ggtgtcacgc tcgtcgtttg gtatggcttc attcagctcc ggttcccaac gatcaaggcg 1920
agttacatga tcccccatgt tgtgcaaaaa agcggttagc tccttcggtc ctccgatcgt 1980
tgtcagaagt aagttggccg cagtgttatc actcatggtt atggcagcac tgcataattc 2040
tcttactgtc atgccatccg taagatgctt ttctgtgact ggtgagtact caaccaagtc 2100
attctgagaa tagtgtatgc ggcgaccgag ttgctcttgc ccggcgtcaa tacgggataa 2160
taccgcgcca catagcagaa ctttaaaagt gctcatcatt ggaaaacgtt cttcggggcg 2220
aaaactctca aggatcttac cgctgttgag atccagttcg atgtaaccca ctcgtgcacc 2280
caactgatct tcagcatctt ttactttcac cagcgtttct gggtgagcaa aaacaggaag 2340
gcaaaatgcc gcaaaaaagg gaataagggc gacacggaaa tgttgaatac tcatcaattg 2400
cctttttcaa tattattgaa gcatttatca gggttattgt ctcatgagcg gttacatatt 2460
tgaatgtatt tagaaaaata aacaaatagg ggttccgcgc acatttcccc gaaaagtgcc 2520
acctgacgtc taagaaacca ttattatcat gacattaacc tataaaaata ggcgtatcac 2580
gaggcccttt catctcgcgc gtttcggtga tgacggtgaa aacctctgac acatgcagct 2640
cccggagaca gtcacagctt gtctgtaagc ggatgccggg agcagacaag cccgtcaggg 2700
cgcgtcagcg ggtgttggcg ggtgtcgggg ctg 2733

<210> SEQ ID NO 15
<211> LENGTH: 4170
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15
ggtcgttcgg ctgcggcgag cggtatcagc tcactcaaag gcggtaatac ggttatccac 60
agaatcaggg gataacgcag gaaagaacat gtgagcaaaa ggccagcaaa aggccaggaa 120

-continued

```
ccgtaaaaag gccgcgttgc tggcgttttt ccataggctc cgcccccctg acgagcatca    180
caaaaatcga cgctcaagtc agaggtggcg aaacccgaca ggactataaa gataccaggc    240
gtttccccct ggaagctccc tcgtgcgctc tcctgttccg accctgccgc ttacccgata    300
cctgtccgcc tttctccctt cgggaagcgt ggcgctttct catagctcac gctgtaggta    360
tctcagttcg gtgtaggtcg ttcgctccaa gctgggctgt gtgcacgaac cccccgttca    420
gcccgaccgc tgcgccttat ccggtaacta tcgtcttgtg tccaacccgg taagacacga    480
cttatcgcca ctggcagcag ccactggtaa caggattagc agagcgaggt atgtaggcgg    540
tgctacagag ttcttgaagt ggtggcctaa ctacggctac actagaagaa cagtatttgg    600
tatctgcgct ctgctgaagc cagttacctt cggaaaaaga gttggtagct cttgatccgg    660
caaacaaacc accgctggta gcggtggttt ttttgtttgc aagcagcaga ttacgcgcag    720
aaaaaaagga tctcaagaag atcctttgat cttttctacg gggtctgacg ctcagtggaa    780
cgaaaactca cgttaaggga ttttggtcat gagattatca aaaaggatct tcacctagat    840
ccttttaaat taaaaatgaa gttttaaatc aatctaaagt atatatgagt aaacttggtc    900
gcatgcttac caatgcttaa tcagtgaggc acctatctca gcgatctgtc tatttcgttc    960
atccatagtt gcctgactgc ccgtcgtgta gataactacg atacgggagg gcttaccatc   1020
tggccccagt gctgcaatga taccgcgaga cccacgctca ccggctccag atttatcagc   1080
aataaaccag ccagccggaa gggccgagcg cagaagtggt cctgcaactt tatccgcctc   1140
catccagtct attaattgtt gccgggaagc tagagtaagt agttcgccag ttaatagttt   1200
gcgcaacgtt gttgccattg ctacaggcat cgtggtgtca cgctcgtcgt ttggtatggc   1260
ttcattcagc tccggttccc aacgatcaag gcgagttaca tgatccccca tgttgtgcaa   1320
aaaagcggtt agctccttcg gtcctccgat cgttgtcaga agtaagttgg ccgcagtgtt   1380
atcactcatg gttatggcag cactgcataa ttctcttact gtcatgccat ccgtaagatg   1440
cttttctgtg actggtgagt actcaaccaa gtcattctga gaatagtgta tgcggcgacc   1500
gagttgctct tgcccggcgt caatacggga taataccgcg ccacatagca gaactttaaa   1560
agtgctcatc attggaaaac gttcttcggg gcgaaaactc tcaaggatct taccgctgtt   1620
gagatccagt tcgatgtaac ccactcgtgc acccaactga tcttcagcat cttttacttt   1680
caccagcgtt tctgggtgag caaaaacagg aaggcaaaat gccgcaaaaa agggaataag   1740
ggcgacacgg aaatgttgaa tactcatcaa ttgccttttt caatattatt gaagcattta   1800
tcagggttat tgtctcatga gcggttacat atttgaatgt atttagaaaa ataaacaaat   1860
aggggttccg cgcacatttc cccgaaaagt gccacctgac gtctaagaaa ccattattat   1920
catgacatta acctataaaa ataggcgtat cacgaggccc tttcatctcg cgcgtttcgg   1980
tgatgacggt gaaaacctct gacacatgca gctcccggag acagtcacag cttgtctgta   2040
agcggatgcc gggagcagac aagcccgtca gggcgcgtca gcgggtgttg gcgggtgtcg   2100
gggctggtaa aacgacggcc agtattaacc ctcactaaag ggaactcgag gctcttcagc   2160
tcacacgcgg ccagggggag ccttcgacac tagtaataca catcatcgtc ctacaagttc   2220
atcaaagtgt tggacagaca actataccag catggatctc ttgtatcggt tcttttctcc   2280
cgctctctcg caataacaat gaacactggg tcaatcatag cctacacagg tgaacagagt   2340
agcgtttata cagggtttat acggtgattc ctacggcaaa aatttttcat ttctaaaaaa   2400
aaaaagaaaa atttttcttt ccaacgctag aaggaaaaga aaaatctaat taaattgatt   2460
```

-continued

```
tggtgatttt ctgagagttc cctttttcat atatcgaatt ttgaatataa aaggagatcg   2520

aaaaaatttt tctattcaat ctgttttctg gttttatttg atagtttttt tgtgtattat   2580

tattatggat tagtactggt ttatatgggt ttttctgtat aacttctttt tattttagtt   2640

tgtttaatct tattttgagt tacattatag ttccctaact gcaagagaag taacattaaa   2700

aatgaaaaag cctgaactca ccgcgacgtc tgtcgagaag tttctgatcg aaaagttcga   2760

cagcgtctcc gacctgatgc agctctcgga gggcgaagaa tctcgtgctt tcagcttcga   2820

tgtaggaggg cgtggatatg tcctgcgggt aaatagctgc gccgatggtt tctacaaaga   2880

tcgttatgtt tatcggcact ttgcatcggc cgcgctcccg attccggaag tgcttgacat   2940

tggggaattc agcgagagcc tgacctattg catctcccgc cgtgcacagg gtgtcacgtt   3000

gcaagacctg cctgaaaccg aactgcccgc tgttctgcag ccggtcgcgg aggccatgga   3060

tgcgatcgct gcggccgatc ttagccagac gagcgggttc ggcccattcg gaccgcaagg   3120

aatcggtcaa tacactacat ggcgtgattt catatgcgcg attgctgatc cccatgtgta   3180

tcactggcaa actgtgatgg acgacaccgt cagtgcgtcc gtcgcgcagg ctctcgatga   3240

gctgatgctt tgggccgagg actgccccga agtccggcac ctcgtgcacg cggatttcgg   3300

ctccaacaat gtcctgacgg acaatggccg cataacagcg gtcattgact ggagcgaggc   3360

gatgttcggg gattcccaat acgaggtcgc caacatcttc ttctggaggc cgtggttggc   3420

ttgtatggag cagcagacgc gctacttcga gcggaggcat ccggagcttg caggatcgcc   3480

gcggctccgg gcgtatatgc tccgcattgg tcttgaccaa ctctatcaga gcttggttga   3540

cggcaatttc gatgatgcag cttgggcgca gggtcgatgc gacgcaatcg tccgatccgg   3600

agccgggact gtcgggcgta cacaaatcgc ccgcagaagc gcggccgtct ggaccgatgg   3660

ctgtgtagaa gtactcgccg atagtggaaa ccgacgcccc agcactcgtc cgagggcaaa   3720

ggaataggtt taacttgata ctactagatt ttttctcttc atttataaaa tttttggtta   3780

taattgaagc tttagaagta tgaaaaaatc cttttttttc attctttgca accaaaataa   3840

gaagcttctt ttattcattg aaatgatgaa tataaaccta acaaaagaaa aagactcgaa   3900

tatcaaacat taaaaaaaaa taaaagaggt tatctgtttt cccatttagt tggagtttgc   3960

attttctaat agatagaact ctcaattaat gtggatttag tttctctgtt cgtttttttt   4020

tgttttgttc tcactgtatt tacatttcta tttagtattt agttattcat ataatcttaa   4080

cttctcgagg agctctcgct cgtccaacgc cggcggacct tgaagagcga gctcccgctg   4140

agcaataact agcgtcatag ctgtttcctg                                   4170
```

<210> SEQ ID NO 16
<211> LENGTH: 2519
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
ggtcgttcgg ctgcggcgag cggtatcagc tcactcaaag gcggtaatac ggttatccac     60

agaatcaggg gataacgcag gaaagaacat gtgagcaaaa ggccagcaaa aggccaggaa    120

ccgtaaaaag gccgcgttgc tggcgttttt ccataggctc cgcccccctg acgagcatca    180

caaaaatcga cgctcaagtc agaggtggcg aaacccgaca ggactataaa gataccaggc    240

gtttccccct ggaagctccc tcgtgcgctc tcctgttccg accctgccgc ttacccgata    300
```

```
cctgtccgcc tttctccctt cgggaagcgt ggcgctttct catagctcac gctgtaggta    360
tctcagttcg gtgtaggtcg ttcgctccaa gctgggctgt gtgcacgaac cccccgttca    420
gcccgaccgc tgcgccttat ccggtaacta tcgtcttgtg tccaacccgg taagacacga    480
cttatcgcca ctggcagcag ccactggtaa caggattagc agagcgaggt atgtaggcgg    540
tgctacagag ttcttgaagt ggtggcctaa ctacggctac actagaagaa cagtatttgg    600
tatctgcgct ctgctgaagc cagttacctt cggaaaaaga gttggtagct cttgatccgg    660
caaacaaacc accgctggta gcggtggttt ttttgtttgc aagcagcaga ttacgcgcag    720
aaaaaaagga tctcaagaag atcctttgat cttttctacg gggtctgacg ctcagtggaa    780
cgaaaactca cgttaaggga ttttggtcat gagattatca aaaaggatct tcacctagat    840
ccttttaaat taaaaatgaa gttttaaatc aatctaaagt atatatgagt aaacttggtc    900
gcatgcttac caatgcttaa tcagtgaggc acctatctca gcgatctgtc tatttcgttc    960
atccatagtt gcctgactgc ccgtcgtgta gataactacg atacgggagg gcttaccatc   1020
tggccccagt gctgcaatga taccgcgaga cccacgctca ccggctccag atttatcagc   1080
aataaaccag ccagccggaa gggccgagcg cagaagtggt cctgcaactt tatccgcctc   1140
catccagtct attaattgtt gccgggaagc tagagtaagt agttcgccag ttaatagttt   1200
gcgcaacgtt gttgccattg ctacaggcat cgtggtgtca cgctcgtcgt ttggtatggc   1260
ttcattcagc tccggttccc aacgatcaag gcgagttaca tgatccccca tgttgtgcaa   1320
aaaagcggtt agctccttcg gtcctccgat cgttgtcaga agtaagttgg ccgcagtgtt   1380
atcactcatg gttatggcag cactgcataa ttctcttact gtcatgccat ccgtaagatg   1440
cttttctgtg actggtgagt actcaaccaa gtcattctga gaatagtgta tgcggcgacc   1500
gagttgctct tgcccggcgt caatacggga taataccgcg ccacatagca gaactttaaa   1560
agtgctcatc attggaaaac gttcttcggg gcgaaaactc tcaaggatct taccgctgtt   1620
gagatccagt tcgatgtaac ccactcgtgc acccaactga tcttcagcat cttttacttt   1680
caccagcgtt tctgggtgag caaaaacagg aaggcaaaat gccgcaaaaa agggaataag   1740
ggcgacacgg aaatgttgaa tactcatcaa ttgccttttt caatattatt gaagcattta   1800
tcagggttat tgtctcatga gcggttacat atttgaatgt atttagaaaa ataaacaaat   1860
aggggttccg cgcacatttc cccgaaaagt gccacctgac gtctaagaaa ccattattat   1920
catgacatta acctataaaa ataggcgtat cacgaggccc tttcatctcg cgcgtttcgg   1980
tgatgacggt gaaaacctct gacacatgca gctcccggag acagtcacag cttgtctgta   2040
agcggatgcc gggagcagac aagcccgtca gggcgcgtca gcgggtgttg gcgggtgtcg   2100
gggctggtaa aacgacggcc agtattaacc ctcactaaag ggaactcgag gctcttcacg   2160
ctcgtccaac gccggcggac ctaagccaat atccccaaaa ttattaagag cgcctccatt   2220
attaactaaa atttcactca gcatccacaa tgtatcaggt atctactaca gatattacat   2280
gtggcgaaaa agacaagaac aatgcaatag cgcatcaaga aaaaacacaa agctttcaat   2340
caatgaatcg aaaatgtcat taaaatagta tataaattga aactaagtca taaagctata   2400
aaaagaaaat ttatttaaat gcaagattta aagtaaattc acttaatccc cgcgtgcttg   2460
gccggccgtt gaagagcgag ctcccgctga gcaataacta gcgtcatagc tgtttcctg    2519
```

<210> SEQ ID NO 17
<211> LENGTH: 2121
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (2109)..(2109)
<223> OTHER INFORMATION: a, c, t, g, unknown or other

<400> SEQUENCE: 17

```
gaattcgccc ttntggatgg cggcgttagt atcgaatcga cagcagtata gcgaccagca     60
ttcacatacg attgacgcat gatattactt tctgcgcact taacttcgca tctgggcaga    120
tgatgtcgag gcgaaaaaaa atataaatca cgctaacatt tgattaaaat agaacaacta    180
caatataaaa aaactataca aatgacaagt tcttgaaaac aagaatcttt ttattgtcag    240
tactgattag aaaaactcat cgagcatcaa atgaaactgc aatttattca tatcaggatt    300
atcaatacca tatttttgaa aaagccgttt ctgtaatgaa ggagaaaact caccgaggca    360
gttccatagg atggcaagat cctggtatcg gtctgcgatt ccgactcgtc caacatcaat    420
acaacctatt aatttcccct cgtcaaaaat aaggttatca agtgagaaat caccatgagt    480
gacgactgaa tccggtgaga atggcaaaag cttatgcatt tctttccaga cttgttcaac    540
aggccagcca ttacgctcgt catcaaaatc actcgcatca accaaaccgt tattcattcg    600
tgattgcgcc tgagcgagac gaaatacgcg atcgctgtta aaaggacaat tacaaacagg    660
aatcgaatgc aaccggcgca ggaacactgc cagcgcatca acaatatttt cacctgaatc    720
aggatattct tctaatacct ggaatgctgt tttgccgggg atcgcagtgg tgagtaacca    780
tgcatcatca ggagtacgga taaaatgctt gatggtcgga agaggcataa attccgtcag    840
ccagtttagt ctgaccatct catctgtaac atcattggca acgctacctt tgccatgttt    900
cagaaacaac tctggcgcat cgggcttccc atacaatcga tagattgtcg cacctgattg    960
cccgacatta tcgcgagccc atttataccc atataaatca gcatccatgt tggaatttaa   1020
tcgcggcctc gaaacgtgag tcttttcctt acccatggtt gtttatgttc ggatgtgatg   1080
tgagaactgt atcctagcaa gattttaaaa ggaagtatat gaaagaagaa cctcagtggc   1140
aaatcctaac cttttatatt tctctacagg ggcgcggcgt ggggacaatt caacgcgtct   1200
gtgaggggag cgtttccctg ctcgcaggtc tgcagcgagg agccgtaatt tttgcttcgc   1260
gccgtgcggc catcaaaatg tatggatgca aatgattata catggggatg tatgggctaa   1320
atgtacgggc gacagtcaca tcatgcccct gagctgcgca cgtcaagact gtcaaggagg   1380
gtattctggg cctccatgtc gctggccggg tgacccggcg gggacgaggc aagctaaaca   1440
gatctgatct tgaaactgag taagatgctc agaatacccg tcaagataag agtataatgt   1500
agagtaatat accaagtatt cagcatattc tcctcttctt ttgtataaat cacggaaggg   1560
atgatttata agaaaaatga atactattac acttcattta ccaccctctg atctagattt   1620
tccaacgata tgtacgtagt ggtataaggt gagggggtcc acagatataa catcgtttaa   1680
tttagtacta acagagactt ttgtcacaac tacatataag tgtacaaata tagtacagat   1740
atgacacact tgtagcgcca acgcgcatcc tacggattgc tgacagaaaa aaaggtcacg   1800
tgaccagaaa agtcacgtgt aattttgtaa ctcaccgcat tctagcggtc cctgtcgtgc   1860
acactgcact caacaccata aaccttagca acctccaaag gaaatcaccg tataacaaag   1920
ccacagtttt acaacttagt ctcttatgaa gttacttacc aatgagaaat agaggctctt   1980
```

```
tctcgagaaa tatgaatatg gatatatata tatatatata tatatatata tatatatgta   2040

aacttggttc ttttttagct tgtgatctct agcttgggtc tctctctgtc gtaacagttg   2100

tgatatcgna agggcgaatt c                                             2121
```

<210> SEQ ID NO 18
<211> LENGTH: 8425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatcga ctacgtcgta aggccgtttc tgacagagta aaattcttga gggaactttc    240

accattatgg gaaatgcttc aagaaggtat tgacttaaac tccatcaaat ggtcaggtca    300

ttgagtgttt tttatttgtt gtattttttt ttttttagag aaaatcctcc aatatcaaat    360

taggaatcgt agtttcatga ttttctgtta cacctaactt tttgtgtggt gccctcctcc    420

ttgtcaatat taatgttaaa gtgcaattct ttttccttat cacgttgagc cattagtatc    480

aatttgctta cctgtattcc tttactatcc tccttttttct ccttcttgat aaatgtatgt    540

agattgcgta tatagtttcg tctaccctat gaacatattc cattttgtaa tttcgtgtcg    600

tttctattat gaatttcatt tataaagttt atgtacaaat atcataaaaa aagagaatct    660

ttttaagcaa ggattttctt aacttcttcg gcgacagcat caccgacttc ggtggtactg    720

ttggaaccac ctaaatcacc agttctgata cctgcatcca aaaccttttt aactgcatct    780

tcaatggcct taccttcttc aggcaagttc aatgacaatt tcaacatcat tgcagcagac    840

aagatagtgg cgatagggtc aaccttattc tttggcaaat ctggagcaga accgtggcat    900

ggttcgtaca aaccaaatgc ggtgttcttg tctggcaaag aggccaagga cgcagatggc    960

aacaaaccca aggaacctgg gataacggag gcttcatcgg agatgatatc accaaacatg   1020

ttgctggtga ttataatacc atttaggtgg gttgggttct taactaggat catggcggca   1080

gaatcaatca attgatgttg aaccttcaat gtagggaatt cgttcttgat ggtttcctcc   1140

acagtttttc tccataatct tgaagaggcc aaaagattag ctttatccaa ggaccaaata   1200

ggcaatggtg gctcatgttg tagggccatg aaagcggcca ttcttgtgat tctttgcact   1260

tctggaacgg tgtattgttc actatcccaa gcgacaccat caccatcgtc ttcctttctc   1320

ttaccaaagt aaatacctcc cactaattct ctgacaacaa cgaagtcagt acctttagca   1380

aattgtggct tgattggaga taagtctaaa agagagtcgg atgcaaagtt acatggtctt   1440

aagttggcgt acaattgaag ttctttacgg atttttagta aaccttgttc aggtctaaca   1500

ctaccggtac cccatttagg accagccaca gcacctaaca aaacggcatc aaccttcttg   1560

gaggcttcca gcgcctcatc tggaagtggg acacctgtag catcgatagc agcaccacca   1620

attaaatgat tttcgaaatc gaacttgaca ttggaacgaa catcagaaat agctttaaga   1680

accttaatgg cttcggctgt gatttcttga ccaacgtggt cacctggcaa aacgacgatc   1740

ttcttagggg cagacattac aatggtatat ccttgaaata tatataaaaa aaggcgcctt   1800

agaccgctcg gccaaacaac caattacttg ttgagaaata gagtataatt atcctataaa   1860
```

```
tataacgttt ttgaacacac atgaacaagg aagtacagga caattgattt tgaagagaat   1920
gtggattttg atgtaattgt tgggattcca tttttaataa ggcaataata ttaggtatgt   1980
ggatatacta gaagttctcc tcgaccgtcg atatgcggtg tgaaataccg cacagatgcg   2040
taaggagaaa ataccgcatc aggaaattgt aaacgttaat attttgttaa aattcgcgtt   2100
aaatttttgt taaatcagct catttttttaa ccaataggcc gaaatcggca aaatccctta   2160
taaatcaaaa gaatagaccg agatagggtt gagtgttgtt ccagtttgga acaagagtcc   2220
actattaaag aacgtggact ccaacgtcaa agggcgaaaa accgtctatc agggcgatgg   2280
cccactacgt ggaagatccg aggcctagct ttaacgaacg cagaattttc gagttattaa   2340
acttaaaata cgctgaaccc gaacatagaa atatcgaatg ggaaaaaaaa actgcataaa   2400
ggcattaaaa gaggagcgaa ttttttttta ataaaaatct taataatcat taaaagataa   2460
ataatagtct atatatacgt atataaataa aaaatattca aaaaataaaa taaactatta   2520
ttttagcgta aaggatgggg aaagagaaaa gaaaaaaatt gatctatcga tttcaattca   2580
attcaattta tttcttttcg gataagaaag caacacctgg caattcctta ccttccaata   2640
attccaaaga agcaccacca ccagtagaga catgggagac ccgggccatg gttagataga   2700
catagggtaa actagcaatg atttgatcaa atgcttgtat tcatctccca ttctcgtaaa   2760
attgtcttta cctgcatatt ggacctctaa aaattggcaa agatatataa cagccataag   2820
taaaggtctt gggatattct ttgttgttaa atactctctg tttatgtctt tccaaacgtc   2880
ctccacttcc ttataaatca gtgtctgagc atattcttcg ttgacattgt attccttcat   2940
gtaagattct aaagagcttg aactatgttt tctctcctgt tccgctttat gagtcatcag   3000
gtcatttaat ctcctaccca gaataccact gtaacggaat aaaggcggag cagatacagc   3060
ccactcaact gattccttag tgaaaatatc gctcattcct agataacagg tagttgttag   3120
caagtttgca ccaccagtga taataactac gggatcgtgc tcttcagttg tcggtatgtg   3180
tccttcatta gcccatttcg cttctaccat tagattcctt acgaattctt taacgaactc   3240
cttcccacag ttgaataaat cagttctacc ttctttggcc agaaactcct ccatttctgt   3300
gtaggtatcc atgaataatt tgtaaatagg cttcatgtat tccggcaacg tgtctaagca   3360
ggtgatcgac catctttcca cggcttcagt gaaaatcttt aactcctcgt aagttccata   3420
tgcgtcatac gtgtcatcaa taagtgttat cacagcaact gccttagtga aaaaaactct   3480
agctcttgaa tactggggtt cgtaaccaga acctaaaccc caaaaatagc attcaacgat   3540
acgatctctc agacatgggg catttttctt aatatcaaat gccttccacc acttgcatac   3600
gtgactcaac tcttccttat gtaggctctg caatagattg aactccagtt tagctaactt   3660
tagcagagtt ttattatggg agtcttgttg ctgatagaag ggtatgtact gggcggcctc   3720
gatccttggc aatctcttcc acaatggttg ctttaaagct ctctggattt cagtgaataa   3780
agcggggttt gtactaaacg cgtcctttgt cataatcgat agccttgatc ttgtgaatcc   3840
cagggcatct tcaagaatta tttcgcccgg aactctcatg gacgtagcct catataattc   3900
caacaatcct tcaacatcat tcgctaacga ttgtttaaaa gcaccattct tgtctttata   3960
gttattaaac acatcacacg tgacatagta tccttgttta cgcatcagcc taaaccataa   4020
gctagacctg tcgccattcc aattatcacc ataggtctcg taaatacatt gcaatgcatg   4080
atcaatttca cgttcaaaat gatacggaat acctaaacgt tgaatctcgt caatcagctt   4140
caacaaattt gcatgtttca taggaatatc caatgcttcc tttaacaact gtcttacttc   4200
```

-continued

```
cttctttaga tcgtttacta tttgctccac accctgttca acttgtttct cataaatcaa   4260
aaattgatcg ccccaaatag aaggtgggaa atttgcaatt ggccttatag gtttctcttc   4320
agtcaaggcc attgttttct gcagatccgg ggtttttttct ccttgacgtt aaagtataga   4380
ggtatattaa caatttttttg ttgatacttt tattacattt gaataagaag taatacaaac   4440
cgaaaatgtt gaaagtatta gttaaagtgg ttatgcagtt tttgcattta tatatctgtt   4500
aatagatcaa aaatcatcgc ttcgctgatt aattacccca gaaataaggc taaaaaacta   4560
atcgcattat catcctatgg ttgttaattt gattcgttca tttgaaggtt tgtggggcca   4620
ggttactgcc aatttttcct cttcataacc ataaaagcta gtattgtaga atctttattg   4680
ttcggagcag tgcggcgcga ggcacatctg cgtttcagga acgcgaccgg tgaagacgag   4740
gacgcacgga ggagagtctt ccttcggagg gctgtcaccc gctcggcggc ttctaatccg   4800
tactaagatc tgctttaatt tggccggcga acgtggcgag aaaggaaggg aagaaagcga   4860
aaggagcggg cgctagggcg ctggcaagtg tagcggtcac gctgcgcgta accaccacac   4920
ccgccgcgct taatgcgccg ctacagggcg cgtcgcgcca ttcgccattc aggctgcgca   4980
actgttggga agggcgatcg gtgcgggcct cttcgctatt acgccagctg cattaatgaa   5040
tcggccaacg cgcggggaga ggcggtttgc gtattgggcg ctcttccgct tcctcgctca   5100
ctgactcgct gcgctcggtc gttcggctgc ggcgagcggt atcagctcac tcaaaggcgg   5160
taatacggtt atccacagaa tcaggggata acgcaggaaa gaacatgtga gcaaaaggcc   5220
agcaaaaggc caggaaccgt aaaaaggccg cgttgctggc gtttttccat aggctccgcc   5280
cccctgacga gcatcacaaa aatcgacgct caagtcagag gtggcgaaac ccgacaggac   5340
tataaagata ccaggcgttt ccccctggaa gctccctcgt gcgctctcct gttccgaccc   5400
tgccgcttac cggatacctg tccgcctttc tcccttcggg aagcgtggcg ctttctcata   5460
gctcacgctg taggtatctc agttcggtgt aggtcgttcg ctccaagctg ggctgtgtgc   5520
acgaaccccc cgttcagccc gaccgctgcg ccttatccgg taactatcgt cttgagtcca   5580
acccggtaag acacgactta tcgccactgg cagcagccac tggtaacagg attagcagag   5640
cgaggtatgt aggcggtgct acagagttct tgaagtggtg gcctaactac ggctacacta   5700
gaaggacagt atttggtatc tgcgctctgc tgaagccagt taccttcgga aaaagagttg   5760
gtagctcttg atccggcaaa caaaccaccg ctggtagcgg tggttttttt gtttgcaagc   5820
agcagattac gcgcagaaaa aaaggatctc aagaagatcc tttgatcttt tctacggggt   5880
ctgacgctca gtggaacgaa aactcacgtt aagggatttt ggtcatgaga ttatcaaaaa   5940
ggatcttcac ctagatcctt ttaaattaaa aatgaagttt taaatcaatc taaagtatat   6000
atgagtaaac ttggtctgac agttaccaat gcttaatcag tgaggcacct atctcagcga   6060
tctgtctatt tcgttcatcc atagttgcct gactccccgt cgtgtagata actacgatac   6120
gggagggctt accatctggc cccagtgctg caatgatacc gcgagaccca cgctcaccgg   6180
ctccagattt atcagcaata aaccagccag ccggaagggc cgagcgcaga agtggtcctg   6240
caactttatc cgcctccatc cagtctatta attgttgccg ggaagctaga gtaagtagtt   6300
cgccagttaa tagtttgcgc aacgttgttg ccattgctac aggcatcgtg gtgtcacgct   6360
cgtcgtttgg tatggcttca ttcagctccg gttcccaacg atcaaggcga gttacatgat   6420
cccccatgtt gtgcaaaaaa gcggttagct ccttcggtcc tccgatcgtt gtcagaagta   6480
agttggccgc agtgttatca ctcatggtta tggcagcact gcataattct cttactgtca   6540
tgccatccgt aagatgcttt tctgtgactg gtgagtactc aaccaagtca ttctgagaat   6600
```

agtgtatgcg gcgaccgagt tgctcttgcc cggcgtcaat acgggataat accgcgccac 6660
atagcagaac tttaaaagtg ctcatcattg gaaaacgttc ttcggggcga aaactctcaa 6720
ggatcttacc gctgttgaga tccagttcga tgtaacccac tcgtgcaccc aactgatctt 6780
cagcatcttt tactttcacc agcgtttctg ggtgagcaaa aacaggaagg caaaatgccg 6840
caaaaaaggg aataagggcg acacggaaat gttgaatact catactcttc ctttttcaat 6900
attattgaag catttatcag ggttattgtc tcatgagcgg atacatattt gaatgtattt 6960
agaaaaataa acaaataggg gttccgcgca catttccccg aaaagtgcca cctgaacgaa 7020
gcatctgtgc ttcattttgt agaacaaaaa tgcaacgcga gagcgctaat ttttcaaaca 7080
aagaatctga gctgcatttt tacagaacag aaatgcaacg cgaaagcgct atttaccaa 7140 cgaagaatct gtgcttcatt tttgtaaaac aaaaatgcaa cgcgagagcg ctaatttttc 7200
aaacaaagaa tctgagctgc atttttacag aacagaaatg caacgcgaga gcgctatttt 7260
accaacaaag aatctatact tcttttttgt tctacaaaaa tgcatcccga gagcgctatt 7320
tttctaacaa agcatcttag attacttttt ttctcctttg tgcgctctat aatgcagtct 7380
cttgataact tttgcactg taggtccgtt aaggttagaa gaaggctact tggtgtcta 7440 ttttctcttc cataaaaaaa gcctgactcc acttcccgcg tttactgatt actagcgaag 7500
ctgcgggtgc atttttcaa gataaaggca tccccgatta tattctatac cgatgtggat 7560
tgcgcatact ttgtgaacag aaagtgatag cgttgatgat tcttcattgg tcagaaaatt 7620
atgaacggtt tcttctattt tgtctctata tactacgtat aggaaatgtt tacattttcg 7680 tattgtttc gattcactct atgaatagtt cttactacaa ttttttgtc taaagagtaa 7740 tactagagat aaacataaaa aatgtagagg tcgagtttag atgcaagttc aaggagcgaa 7800
aggtggatgg gtaggttata tagggatata gcacagagat atatagcaaa gagatacttt 7860
tgagcaatgt ttgtggaagc ggtattcgca atattttagt agctcgttac agtccggtgc 7920
gtttttggtt ttttgaaagt gcgtcttcag agcgcttttg gttttcaaaa gcgctctgaa 7980
gttcctatac tttctagaga ataggaactt cggaatagga acttcaaagc gtttccgaaa 8040
acgagcgctt ccgaaaatgc aacgcgagct gcgcacatac agctcactgt tcacgtcgca 8100
cctatatctg cgtgttgcct gtatatatat atacatgaga agaacggcat agtgcgtgtt 8160
tatgcttaaa tgcgtactta tatgcgtcta tttatgtagg atgaaaggta gtctagtacc 8220
tcctgtgata ttatcccatt ccatgcgggg tatcgtatgc ttccttcagc actacccttt 8280
agctgttcta tatgctgcca ctcctcaatt ggattagtct catccttcaa tgctatcatt 8340
tcctttgata ttggatcata ctaagaaacc attattatca tgacattaac ctataaaaat 8400
aggcgtatca cgaggccctt tcgtc 8425

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gagtgaacct gctgcctggc gtgctctgac tcagtacatt tcatagtgga tggcggcgtt 60
agtatc 66

<210> SEQ ID NO 20
<211> LENGTH: 65
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
cgtgtatacg ttttccgctt ctgctcttcg tcttttctct tcttccgata tcacaactgt 60
tacga 65

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
taataaggat ccatgtcaac tttgcctatt tc 32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
ttatagctag ctcaaacgac cataggatga ac 32

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
gtttaaacta ctattagctg aattgccact 30

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
actgcaaagt acacatatat cccgggtgtc agctctttta gatcgg 46

<210> SEQ ID NO 25
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ccgatctaaa agagctgaca cccgggatat atgtgtactt tgcagt 46

-continued

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
gtttaaacgg cgtcagtcca ccagctaaca 30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gtttaaactt gctaaattcg agtgaaacac 30

<210> SEQ ID NO 28
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
aaagatgaat tgaaaagctt cccgggtatg gaccctgaaa ccacag 46

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ctgtggtttc agggtccata cccgggaagc ttttcaattc atcttt 46

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gtttaaaccc aacaataata atgtcagatc 30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gtttaaacta ctcagtatat taagtttcga 30

-continued

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
atctctcgca agagtcagac tgactcccgg gcgtgaataa gcttcgggtg acccttatgg 60
cattcttttt 70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
aaaaagaatg ccataagggt cacccgaagc ttattcacgc ccgggagtca gtctgactct 60
tgcgagagat 70

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gtttaaacaa tttagtgtct gcgatgatga 30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gtttaaacta ttgtgagggt cagttatttc 30

<210> SEQ ID NO 36
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gcggggacga ggcaagctaa actttagtat attcttcgaa gaaa 44

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
tttcttcgaa gaatatacta aagtttagct tgcctcgtcc ccgc 44

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
caatcaacgt ggagggtaat tctgctagcc tctcccgggt ggatggcggc gttagtatcg 60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cgatactaac gccgccatcc acccgggaga ggctagcaga attaccctcc acgttgattg 60

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gtttaaacgc cgccgttgtt gttattgtag 30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
gtttaaactt ttccaatagg tggttagcaa 30

<210> SEQ ID NO 42
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gggtgacccg gcggggacga ggcaagctaa acgtcttcct ttctcttacc aaagt 55

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
actttggtaa gagaaaggaa gacgtttagc ttgcctcgtc cccgccgggt caccc 55

<210> SEQ ID NO 44
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
aatatcataa aaaaagagaa tctttcccgg gtggatggcg gcgttagtat cgaatcgaca 60
gc 62

<210> SEQ ID NO 45
<211> LENGTH: 62
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gctgtcgatt cgatactaac gccgccatcc acccgggaaa gattctcttt ttttatgata 60
tt 62

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gtttaaacgt gttaacgttt ctttcgccta cgtggaagga gaatc 45

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tccccccggg ttaaaaaaaa tccttggact agtca 35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tccccccggg agttatgaca attacaacaa cagaa 35

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tccccccggg tatatatata tcattgttat 30

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tccccccggg aaaagtaagt caaaaggcac 30

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tccccccggg atggtctgct taaatttcat 30

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tccccccggg tagcttgtac ccattaaaag aattttatca tgccg 45

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
tccccccggg tttctcattc aagtggtaac 30

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
tccccccggg taaataaaga aaataaagtt 30

<210> SEQ ID NO 55
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
aatttttgaa aattcaatat aaatggcttc agaaaaagaa attagga      47

<210> SEQ ID NO 56
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcctaatttc tttttctgaa gccatttata ttgaattttc aaaaatt      47

<210> SEQ ID NO 57
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agttttcacc aattggtctg cagccattat agttttttct ccttgacgtt a      51

<210> SEQ ID NO 58
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
taacgtcaag gagaaaaaac tataatggct gcagaccaat tggtgaaaac t      51

<210> SEQ ID NO 59
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aatttttgaa aattcaatat aaatgaaact ctcaactaaa ctttgtt      47

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aacaaagttt agttgagagt ttcatttata ttgaattttc aaaaatt      47

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aatttttgaa aattcaatat aaatgtctca gaacgtttac attgtat                          47

<210> SEQ ID NO 62
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atacaatgta aacgttctga gacatttata ttgaattttc aaaaatt                          47

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgcagaagtt aagaacggta atgacattat agttttttct ccttgacgtt a                    51

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
taacgtcaag gagaaaaaac tataatgtca ttaccgttct taacttctgc a                    51

<210> SEQ ID NO 65
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65 aattttgaa aattcaatat aaatgtcaga gttgagagcc ttcagtg                          47

<210> SEQ ID NO 66
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cactgaaggc tctcaactct gacatttata ttgaattttc aaaaatt                         47

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggtaacggat gctgtgtaaa cggtcattat agttttttct ccttgacgtt a                   51

<210> SEQ ID NO 68
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
taacgtcaag gagaaaaaac tataatgacc gtttacacag catccgttac c 51

<210> SEQ ID NO 69
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
aatttttgaa aattcaatat aaatgactgc cgacaacaat agtatgc 47

<210> SEQ ID NO 70
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gcatactatt gttgtcggca gtcatttata ttgaattttc aaaaatt 47

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ggtaagacgg ttgggtttta tcttttgcag ttggtactat taagaacaat cacaggaaac 60
agctatgacc 70

<210> SEQ ID NO 72
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ttgcgttttg tactttggtt cgctcaattt tgcaggtaga taatcgaaaa gttgtaaaac 60
gacggccagt 70

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
tgaagagcga gctcccgctg 20

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
tgaagagcct cgagttccct ttag 24

<210> SEQ ID NO 75
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
atatactagg aaaactcttt atttaataac aatgatatat atatattcca gtggtgcatg 60
aac 63

<210> SEQ ID NO 76
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
aatttgtgag tttagtatac atgcatttac ttataataca gtttttcaac gcattacgta 60
ggc 63

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
cgctcgtcca acgccggcgg acct 24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
acggccggcc aagcacgcgg ggat 24

<210> SEQ ID NO 79
<211> LENGTH: 30
<212> TYPE: DNA
<213> ORGANISM: Artificial Sequence
<220> FEATURE:

<223> OTHER INFORMATION: Description of Artificial Sequence: Synthetic
primer

<400> SEQUENCE: 79
atggctacca atttgttgtg cttgtctaac 30

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
tcagacatac atcaactgat taataggaaa agggtc 36

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
atggctaccg agttgttgtg cttg 24

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
tcacctctca aaaggtaata taggttcagt aataac 36

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
atggccaccg agttgttgtg c 21

<210> SEQ ID NO 84
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
tcacctctca aaaggtaaga ttggttc 27

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
tttaaaggat ccatggctac caatttgttg tg 32

<210> SEQ ID NO 86
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tatttcgcta gctcagacat acatcaactg attaatag 38

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
tttaaaggat ccatggctac cgagttgttg tg 32

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
catatcgcta gctcacctct caaaaggtaa tataggttc 39

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
aatttaggat ccatggccac cgagttgttg 30

<210> SEQ ID NO 90
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
tatatcgcta gctcacctct caaaaggtaa gattggttc 39

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
caaataggat ccatggcaaa ttaccagcct aatttg 36

<210> SEQ ID NO 92
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
caaataggat ccatggctaa ttacgagcca aactcatg 38

<210> SEQ ID NO 93
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
caaataggat ccatggccaa ctacgagcca aattc 35

<210> SEQ ID NO 94
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
gcgtacaaag gtaacttacc gtgaataacc aaggcagcga cc 42

<210> SEQ ID NO 95
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
ggctccccct ggccgcgtgt gagcttatat tgaattttca aaaattc 47

<210> SEQ ID NO 96
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gctcacacgc ggccaggggg agccatggct accgagttgt tgtg 44

<210> SEQ ID NO 97
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
gctcacacgc ggccaggggg agccatggct aattacgagc caaactcatg 50

<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
aggtccgccg gcgttggacg agcgtcacct ctcaaaaggt aatatagg 48

<210> SEQ ID NO 99
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
ctagcgattc tcattggaat acgtcgacac tagtaataca catc 44

<210> SEQ ID NO 100
<211> LENGTH: 95
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
cgatgcgttc aattcctcta ctaatttagg gaaaacgttc aagaatctct ctctcctaat 60
ttctttttct gaagccatct ttgtatagcc cttaa 95

<210> SEQ ID NO 101
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
gatgtgtatt actagtgtcg acgtattcca atgagaatcg ctag 44

<210> SEQ ID NO 102
<211> LENGTH: 3901
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102
gtttaaactt caaagctcga tgcctcataa acttcggtag ttatattact ctgagatgac 60
ttatactctt tttccaaatc cacattattt ggcgcaaagg tctcattgga agattccata 120
agttggcgag agttcaatct ttttgaagag ccgcttaaat gtaatgatag attgtctggc 180
attattccct cctattctta ttatgcgtag gaatgtcttc gaaccgaaag atcttctcta 240
tggggtatgc tttagagtga aattaagaaa ggagttttat acagatgata cctaatcatc 300

-continued

```
atataagtaa gagagaacag agatttaatg gaaaatggaa aagggcaaat tggcgctgaa    360
tcaaatagtt tattatatct ttacaatttg tcctgatttt gtccttgtct aacttgaaaa    420
tttttcattc tgatgtcata cgactttttt ccggtctagg aaatcggtga aagctttttt    480
tttttcctat cttcttgtcc atcggaattt ttctgtcatt tcttttcctc ctcgcgcttg    540
tctactaaaa tctgaattgt ccaaattcag tacaaaatta atcagtagga caaagggttc    600
tcgtagagtc cccggaaaaa aaaaaggaca aaaagtttca agacggcaat ctctttttac    660
tgcatctcgt cagttggcaa cttgccaaga acttcgcaaa tgactttgac atatgataag    720
acgtcaactg ccccacgtac aataacaaaa tggtagtcat atcatgtcaa gaataggtat    780
ccaaaacgca gcggttgaaa gcatatcaag aattttgtcc ctgtgtttta aagtttgtgg    840
ataatcgaaa tctcttacat tgaaaacatt atcatacaat catttattaa gtagttgaag    900
catgtatgaa ctataaaagt gttactactc gttattattg cgtattttgt gatgctaaag    960
ttatgagtct cgagaagtta agattatatg aataactaaa tactaaatag aaatgtaaat   1020
acagtgagaa caaaacaaaa aaaaacgaac agagaaacta aatccacatt aattgagagt   1080
tctatctatt agaaaatgca aactccaact aaatgggaaa acagataacc tcttttattt   1140
ttttttaatg tttgatattc gagtcttttt cttttgttag gtttatattc atcatttcaa   1200
tgaataaaag aagcttctta ttttggttgc aaagaatgaa aaaaaaggat tttttcatac   1260
ttctaaagct tcaattataa ccaaaaaattt tataaatgaa gagaaaaaat ctagtagtat   1320
caagttaaac ctattccttt gccctcggac gagtgctggg gcgtcggttt ccactatcgg   1380
cgagtacttc tacacagcca tcggtccaga cggccgcgct tctgcgggcg atttgtgtac   1440
gcccgacagt cccggctccg gatcggacga ttgcgtcgca tcgaccctgc gcccaagctg   1500
catcatcgaa attgccgtca accaagctct gatagagttg gtcaagacca atgcggagca   1560
tatacgcccg gagccgcggc gatcctgcaa gctccggatg cctccgctcg aagtagcgcg   1620
tctgctgctc catacaagcc aaccacggcc tccagaagaa gatgttggcg acctcgtatt   1680
gggaatcccc gaacatcgcc tcgctccagt caatgaccgc tgttatgcgg ccattgtccg   1740
tcaggacatt gttggagccg aaatccgcgt gcacgaggtg ccggacttcg gggcagtcct   1800
cggcccaaag catcagctca tcgagagcct gcgcgacgga cgcactgacg gtgtcgtcca   1860
tcacagtttg ccagtgatac acatggggat cagcaatcgc gcatatgaaa tcacgccatg   1920
tagtgtattg accgattcct tgcggtccga atgggccgaa cccgctcgtc tggctaagat   1980
cggccgcagc gatcgcatcc atggcctccg cgaccggctg cagaacagcg ggcagttcgg   2040
tttcaggcag gtcttgcaac gtgacaccct gtgcacggcg ggagatgcaa taggtcaggc   2100
tctcgctgaa ttccccaatg tcaagcactt ccggaatcgg gagcgcggcc gatgcaaagt   2160
gccgataaac ataacgatct ttgtagaaac catcggcgca gctatttacc cgcaggacat   2220
atccacgccc tcctacatcg aagctgaaag cacgagattc ttcgccctcc gagagctgca   2280
tcaggtcgga gacgctgtcg aactttcga tcagaaactt ctcgacagac gtcgcggtga    2340
gttcaggctt tttcattttt aatgttactt ctcttgcagt tagggaacta taatgtaact   2400
caaaataaga ttaaacaaac taaaataaaa agaagttata cagaaaaacc catataaacc   2460
agtactaatc cataataata atacacaaaa aaactatcaa ataaaaccag aaaacagatt   2520
gaatagaaaa attttttcga tctcctttta tattcaaaat tcgatatatg aaaaagggaa   2580
ctctcagaaa atcaccaaat caatttaatt agatttttct tttccttcta gcgttggaaa   2640
gaaaaatttt tcttttttttt tttagaaatg aaaaattttt gccgtaggaa tcaccgtata   2700
```

aaccctgtat aaacgctact ctgttcacct gtgtaggcta tgattgaccc agtgttcatt 2760
gttattgcga gagagcggga gaaaagaacc gatacaagag atccatgctg gtatagttgt 2820
ctgtccaaca ctttgatgaa cttgtaggac gatgatgtgt attactagtg tcgacactgc 2880
tgaagaattt gatttttcta gccattccca tagacgttac aatccactaa ccgattcatg 2940
gatcttagtt tctccacaca gagctaaaag accttggtta ggtcaacagg aggctgctta 3000
caagcccaca gctccattgt atgatccaaa atgctatcta tgtcctggta acaaaagagc 3060
tactggtaac ctaaacccaa gatatgaatc aacgtatatt ttccccaatg attatgctgc 3120
cgttaggctc gatcaaccta ttttaccaca gaatgattcc aatgaggata atcttaaaaa 3180
taggctgctt aaagtgcaat ctgtgagagg caattgtttc gtcatatgtt ttagccccaa 3240
tcataatcta accattccac aaatgaaaca atcagatctg gttcatattg ttaattcttg 3300
gcaagcattg actgacgatc tctccagaga agcaagagaa aatcataagc ctttcaaata 3360
tgtccaaata tttgaaaaca aaggtacagc catgggttgt tccaacttac atccacatgg 3420
ccaagcttgg tgcttagaat ccatccctag tgaagtttcg caagaattga aatcttttga 3480
taaatataaa cgtgaacaca atactgattt gtttgccgat tacgtcaaat tagaatcaag 3540
agagaagtca agagtcgtag tggagaatga atcctttatt gttgttgttc catactgggc 3600
catctggcca tttgagacct tggtcatttc aaagaagaag cttgcctcaa ttagccaatt 3660
taaccaaatg gtgaaggagg acctcgcctc gattttaaag caactaacta ttaagtatga 3720
taatttattt gaaacgagtt tcccatactc aatgggtatc catcaggctc ctttgaatgc 3780
gactggtgat gaattgagta atagttggtt tcacatgcat ttctacccac ctttactgag 3840
atcagctact gttcggaaat tcttggttgg ttttgaattg ttaggtgagc ctcgtttaaa 3900
c 3901

<210> SEQ ID NO 103
<211> LENGTH: 1118
<212> TYPE: DNA
<213> ORGANISM: Saccharomyces cerevisiae

<400> SEQUENCE: 103
accataccac agcttttcaa ttcaattcat catttttttt ttattctttt ttttgatttc 60
ggtttctttg aaattttttt gattcggtaa tctccgaaca gaaggaagaa cgaaggaagg 120
agcacagact tagattggta tatatacgca tatgtagtgt tgaagaaaca tgaaattgcc 180
cagtattctt aacccaactg cacagaacaa aaacctgcag gaaacgaaga taaatcatgt 240
cgaaagctac atataaggaa cgtgctgcta ctcatcctag tcctgttgct gccaagctat 300
ttaatatcat gcacgaaaag caaacaaact tgtgtgcttc attggatgtt cgtaccacca 360
aggaattact ggagttagtt gaagcattag gtcccaaaat ttgtttacta aaaacacatg 420
tggatatctt gactgatttt tccatggagg gcacagttaa gccgctaaag gcattatccg 480
ccaagtacaa tttttttactc ttcgaagaca gaaaatttgc tgacattggt aatacagtca 540
aattgcagta ctctgcgggt gtatacagaa tagcagaatg ggcagacatt acgaatgcac 600
acggtgtggt gggcccaggt attgttagcg gtttgaagca ggcggcagaa gaagtaacaa 660
aggaacctag aggccttttg atgttagcag aattgtcatg caagggctcc ctatctactg 720
gagaatatac taagggtact gttgacattg cgaagagcga caaagatttt gttatcggct 780
ttattgctca aagagacatg ggtggaagag atgaaggtta cgattggttg attatgacac 840

-continued

```
ccggtgtggg tttagatgac aagggagacg cattgggtca acagtataga accgtggatg    900

atgtggtctc tacaggatct gacattatta ttgttggaag aggactattt gcaaagggaa    960

gggatgctaa ggtagagggt gaacgttaca gaaaagcagg ctgggaagca tatttgagaa   1020

gatgcggcca gcaaaactaa aaaactgtat tataagtaaa tgcatgtata ctaaactcac   1080

aaattagagc ttcaatttaa ttatatcagt tattaccc                           1118


<210> SEQ ID NO 104
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104

tccttattac tgcgatatac agtgtgaggt attctaagcg gtatattcac ctcgagaagt     60

taagattata                                                            70


<210> SEQ ID NO 105
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105

atccccgcgt gcttggccgg ccgtttcgac actagtaata cacatc                    46


<210> SEQ ID NO 106
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106

atcggcgctc gcggcctgca ggttagagct cctcgagaag ttaag                     45


<210> SEQ ID NO 107
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107

aacctgcagg ccgcgagcgc cgatatatat gtgtactttg cagttatg                  48


<210> SEQ ID NO 108
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108

cgaggaactc ttggtattct tgccacgact catctccatg cagttg                    46


<210> SEQ ID NO 109
```

<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
atatactagg aaaactcttt atttaataac aatgatatat atatattcca gtggtgcatg 60
aac 63

<210> SEQ ID NO 110
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
aatttgtgag tttagtatac atgcatttac ttataataca gtttttcaac gcattacgta 60
ggc 63

<210> SEQ ID NO 111
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ttctgtaatg aaggagaaaa ctcaccgagg cagttccata ggatgaccat accacagctt 60
ttcaa 65

<210> SEQ ID NO 112
<211> LENGTH: 65
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
gccgcgcccc tgtagagaaa tataaaaggt taggatttgc cactggggta ataactgata 60
taatt 65

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
tcgactctag gcagataagg 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
gtcgataacc atggtactcc 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
atcctaagtc gtggctattg 20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
accgaatgat gctctagatg 20

<210> SEQ ID NO 117
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
tggcttcaga aaaagaaatt aggagagaga gattcttgaa cgttttccct accataccac 60
agcttttcaa 70

<210> SEQ ID NO 118
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
tatttttcaa taaagaatat cttccactac tgccatctgg cgtcataact gggtaataac 60
tgatataatt 70

<210> SEQ ID NO 119
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
attactgcag gacggtagca acaagaatat ag 32

<210> SEQ ID NO 120
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
gaaataggca aagttgacat ttttgaggga atattcaact g 41

<210> SEQ ID NO 121
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
cagttgaata ttccctcaaa aatgtcaact ttgcctattt c 41

<210> SEQ ID NO 122
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
tataggatcc cttcgagcgt cccaaaacct tc 32

<210> SEQ ID NO 123
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
ttgtgatgct aaagttatga gtctcgagaa gttaagatta tatg 44

<210> SEQ ID NO 124
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
catataatct taacttctcg agactcataa ctttagcatc acaa 44

<210> SEQ ID NO 125
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
gtttaaactt caaagctcga tgcctcat 28

<210> SEQ ID NO 126
<211> LENGTH: 28
<212> TYPE: DNA
<213> ORGANISM: Artificial Sequence
<220> FEATURE:

-continued

```
<223> OTHER INFORMATION: Description of Artificial Sequence: Synthetic
      primer

<400> SEQUENCE: 126

gtttaaacga ggctcaccta acaattca                                    28


<210> SEQ ID NO 127
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127

gatgtgtatt actagtgtcg acactgctga agaatttgat tttt                  44


<210> SEQ ID NO 128
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

aaaaatcaaa ttcttcagca gtgtcgacac tagtaataca catc                  44
```

MICROBIAL DERIVED ISOPRENE AND METHODS FOR MAKING THE SAME

CROSS REFERENCE TO RELATED APPLICATION

This is a divisional application of the U.S. Non-Provisional application Ser. No. 13/887,381, which is a divisional application of the U.S. Non-Provisional application Ser. No. 13/629,623, now U.S. Pat. No. 8,492,605, which is a divisional application of the U.S. Non-Provisional application Ser. No. 12/659,216, now U.S. Pat. No. 8,324,442, which claims the benefit of priority from U.S. Provisional Application No. 61/202,474, filed Mar. 3, 2009, all of which in their entirety are incorporated herein by reference.

BACKGROUND OF THE INVENTION

Isoprene is a five carbon hydrocarbon (2-methyl-1,3-butadiene), that is an industrial chemical used in a range of industrial application such as tires, footwear, sporting goods, latex, tapes, labels, and medical disposables. Isoprene is also a natural compound produced in biological systems. While isoprene is made naturally in various organisms ranging from microbes to animals, most naturally occurring isoprene has traditionally been extracted from rubber plants. However, extraction yields are low and these quantities are far less than are required for many commercial applications. As a result, isoprene is primarily produced synthetically from petroleum sources, most often from ethylene using a steam cracking process.

Due to the growing concern for climate change and thus a need to make products we need more sustainably, there is an urgent need for bio- or renewable isoprene that will help meet global isoprene demands but that can be produced in a more environmentally friendly way. The current invention addresses this need.

SUMMARY OF THE INVENTION

The present invention provides microbial derived isoprene compositions and methods for making and purifying the same.

In one aspect of the invention, a gaseous isoprene composition is provided comprising: isoprene, carbon dioxide and water, wherein the isoprene is in an amount between about 0.1% and about 15% by volume; wherein the carbon dioxide is in an amount between about 0.04% and about 35% by volume; wherein the water is in an amount greater than about 70% of its saturation amount; and wherein the gaseous isoprene composition comprises 1 part per million or less than 1 part per million of any one of the following impurities: $C_2$-$C_5$ alkynes, cyclopentadiene, piperylene, and 1,4-pentadiene.

In some embodiments, the gaseous composition comprises less than about 3% by weight of water. In certain embodiments, the gaseous composition further comprises oxygen in an amount between about 1% and about 20% by volume. In some embodiments, the gaseous composition further comprises nitrogen in an amount greater than about 50% by volume. In certain embodiments, the gaseous composition further comprises argon in an amount less than about 0.9% by volume or greater than about 1.0% by volume. In certain embodiments, the gaseous composition further comprises ethanol in an amount less than about 0.5% by volume or more than about 1% by volume. In certain embodiments, the gaseous composition further comprises 1 part per million or less of cyclopentadiene, piperylene, 1,4-pentadiene, or a combination thereof.

In another aspect a liquid isoprene composition is provided comprising: isoprene in an amount of at least 65% by weight and carbon dioxide in an amount between about 0.01% and about 1% by weight, wherein the isoprene composition comprises 1 part per million or less than 1 part per million of any one of the following impurities: $C_2$-$C_5$ alkynes, cyclopentadiene, piperylene, and 1,4-pentadiene.

In some embodiments, the liquid isoprene composition disclosed herein comprises at least about 80% or at least about 95% isoprene by weight. In some embodiments, the liquid isoprene composition comprises less than about 1% by weight of water. In certain embodiments, the liquid isoprene composition further comprises nitrogen in an amount between about 0.001% and about 1% by weight. In some embodiments, the liquid isoprene composition further comprises ethanol in an amount greater than about 0.01% by weight. In certain embodiments, the carbon dioxide is in an amount between about 0.05% and about 1% by weight, or between about 0.1% and about 1% by weight, or between about 0.2% and about 0.7% by weight.

In another aspect, a method for making and purifying isoprene is provided. The method comprises:

a. obtaining a first gaseous composition comprising isoprene and water wherein the gaseous composition comprises 1 part per million or less of $C_2$-$C_5$ alkynes;
b. flowing the first gaseous composition through a first chiller wherein the first chiller has a temperature of between about 10° C. and about −15° C. thereby resulting in a second gaseous composition and wherein the second gaseous composition comprises less water than the first gaseous composition;
c. flowing the second gaseous composition through a second chiller wherein the second chiller has a temperature below −35° C.; and
d. collecting the resulting liquid isoprene composition.

In another aspect, another method is provided. The method comprises:

a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition; and
d. subjecting the second gaseous composition to a second cooling step whereby a liquid isoprene composition is collected.

In another aspect, another method is provided. The method comprises:

a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition;
d. subjecting the second gaseous composition to a second cooling step whereby a liquid isoprene composition is collected; and e. optionally, contacting either the first gaseous composition, the second gaseous composition and/or the liquid isoprene composition with a membrane containing modified zeolites or molecular seive to provide a purified isoprene composition.

In another aspect, another method is provided. The method comprises:

a. contacting a plurality of host cells capable of making isoprene in an aqueous medium wherein the aqueous medium is in contact with an immiscible organic liquid and the aqueous medium, the host cells, and the immiscible organic liquid is in a closed vessel; and
b. culturing the host cells in the aqueous medium whereby the host cells make isoprene and the isoprene is captured in the immiscible organic liquid.

In another aspect, another method is provided. The method comprises:

a. obtaining a first gaseous composition comprising:
    i. isoprene in an amount between about 0.1% and about 15% by volume;
    ii. carbon dioxide in an amount between about 0.04% and about 35% by volume;
    iii. oxygen in an amount between about 1% and about 20% by volume;
    iv. nitrogen in an amount greater than about 50% by volume;
    v. argon in an amount less than about 0.9% by volume;
    vi. water in an amount greater than about 70% of its saturation amount;
    vii. 1 part per million or less of C2-C5 alkyne, cyclopentadiene, piperylene, and 1,4-pentadiene; and
    viii. ethanol;
b. flowing the first gaseous composition through a first chiller and an operably connected flash drum, wherein the first chiller has a temperature of between about 10° C. and about −15° C. thereby resulting in a second gaseous composition and wherein the second gaseous composition comprises less water than the first gaseous composition;
c. flowing the second gaseous composition through a second chiller and an operably connected flash drum, wherein the second chiller has a temperature between about 35° C. and about −85° C.; and
d. collecting the resulting liquid isoprene composition.

An isoprene production system comprising:

a. a bioreactor capable of culturing a plurality of host cells;
b. a first chiller and flash drum operably connected to the overhead stream of the bioreactor, the first chiller capable of operating in a temperature range of between 10° C. and −15° C.; and
c. a second chiller and flash drum operably connected to the overhead stream exiting from the first chiller and flash drum, the second chiller capable of operating in a temperature below −35° C.

In yet another aspect, an isoprene production system is provided. The system comprises:

a. a closed vessel;
b. an aqueous medium, within the vessel, forming a first phase;
c. a plurality of host cells, within the aqueous medium, capable of making isoprene; and,
d. a liquid organic second phase, capable of capturing the isoprene made by the host cells, in contact with the first phase.

BRIEF DESCRIPTION OF THE DRAWINGS

FIG. 4 is a schematic representation of the DXP pathway for the production of IPP and dimethylallyl pyrophosphate ("DMAPP"). Dxs is 1-deoxy-D-xylulose-5-phosphate synthase; Dxr is 1-deoxy-D-xylulose-5-phosphate reductoisomerase (also known as IspC); IspD is 4-diphosphocytidyl-2C-methyl-D-erythritol synthase; IspE is 4-diphosphocytidyl-2C-methyl-D-erythritol synthase; IspF is 2C-methyl-D-erythritol 2,4-cyclodiphosphate synthase; IspG is 1-hydroxy-2-methyl-2-(E)-butenyl 4-diphosphate synthase (IspG); and ispH is isopentenyl/dimethylallyl diphosphate synthase.

DETAILED DESCRIPTION OF THE INVENTION

Definitions

Figure 1:
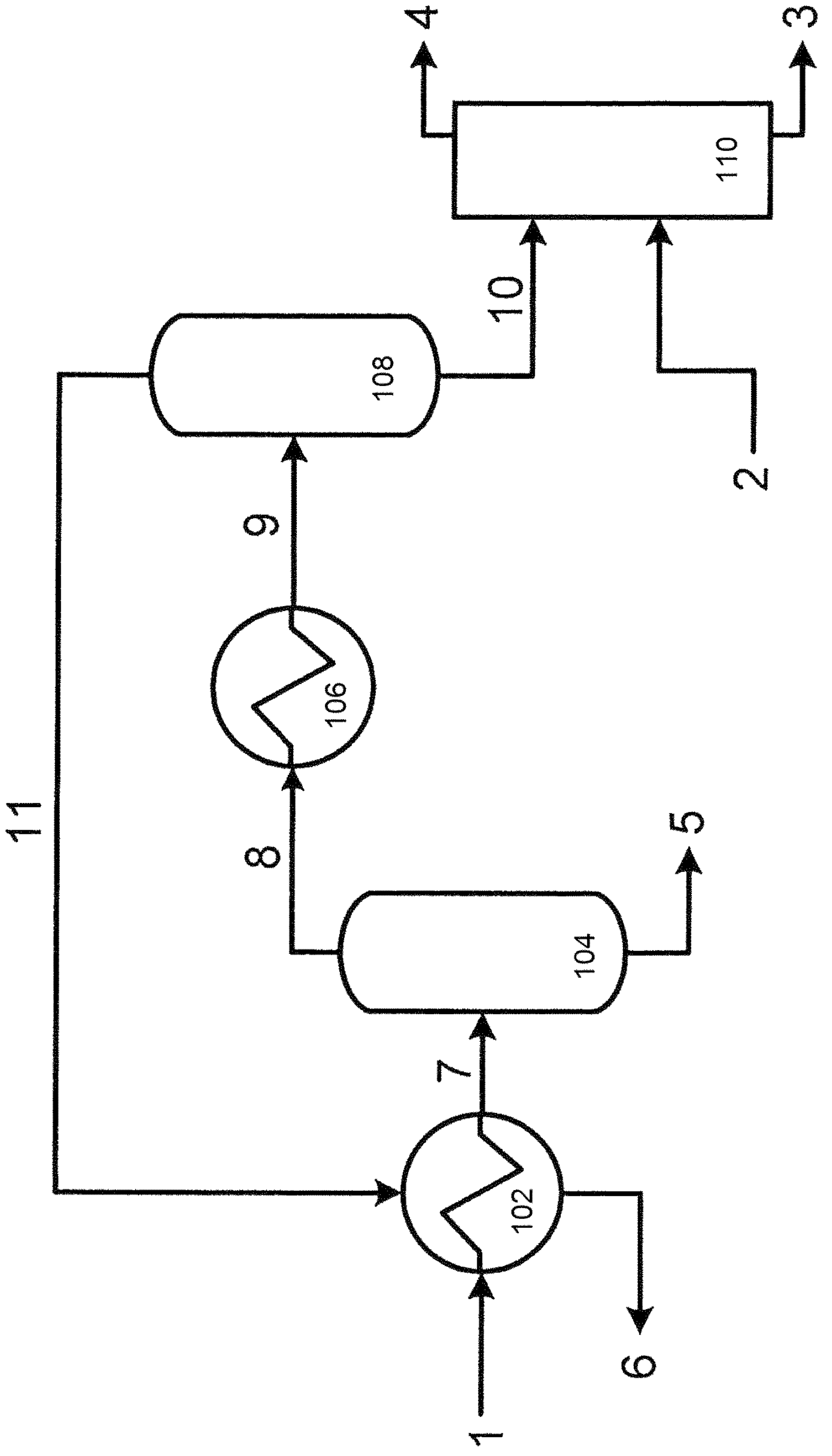
FIG. 1 is a schematic representation of an exemplary separation system.

Unless defined otherwise, all technical and scientific terms used herein have the same meaning as commonly understood by one of ordinary skill in the art to which this invention belongs. Reference is made here to a number of terms that shall be defined to have the following meanings:

"Bio-organic compound" refers to an organic compound having at least five carbon atoms that can be made by a host cell by taking a carbohydrate carbon source and converting the carbohydrate carbon source into the desired product.

"Deoxyxylulose 5-phosphate pathway" or "DXP pathway" is used herein to refer to the pathway that converts glyceraldehyde-3-phosphate and pyruvate to IPP and DMAPP. The DXP pathway is illustrated schematically in FIG. 4.

"Endogenous" refers to a substance or process that can occur naturally, e.g., in a non-recombinant host cell.

"Heterologous nucleic acid" as used herein refers to a nucleic acid wherein at least one of the following is true: (a) the nucleic acid is foreign ("exogenous") to (that is, not naturally found in) a given host cell; (b) the nucleic acid comprises a nucleotide sequence that is naturally found in (that is, is "endogenous to") a given host cell, but the nucleotide sequence is produced in an unnatural (for example, greater than expected or greater than naturally found) amount in the cell; (c) the nucleic acid comprises a nucleotide sequence that differs in sequence from an endogenous nucleotide sequence, but the nucleotide sequence encodes the same protein (having the same or substantially the same amino acid sequence) and is produced in an unnatural (for example, greater than expected or greater than naturally found) amount in the cell; or (d) the nucleic acid comprises two or more nucleotide sequences that are not found in the same relationship to each other in nature (for example, the nucleic acid is recombinant).

"Host cell" and "microorganism" are used interchangeably herein to refer to any archae, bacterial, or eukaryotic living cell into which a heterologous nucleic acid can be or has been inserted. The term also relates to the progeny of the original cell, which may not necessarily be completely identical in morphology or in genoic or total DNA complement to the original parent, due to natural, accidental, or deliberate mutation.

"Isoprenoid" and "isoprenoid compound" are used interchangeably herein and refer to a compound derivable from isopentenyl diphosphate.

"Isolate" and "isolating" when referred to a bio-organic compound is the enrichment of the amount of the bio-organic compound in a composition. Consequently, the amount of the bio-organic compound in a composition after the bio-organic compound has been isolated or subject to an isolating step is greater than the amount present in the composition prior to such step.

"Mevalonate pathway" or "MEV pathway" is used herein to refer to the biosynthetic pathway that converts acetyl-CoA to IPP. The MEV pathway is illustrated schematically in FIG. 3.

"Naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

"Optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

"Pyrophosphate" is used interchangeably herein with "diphosphate".

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, greater than 99.9 vol. % of the compound; or less than 20 vol. %, less than 10 vol. %, less than 5 vol. %, less than 4 vol. %, less than 3 vol. %, less than 2 vol. %, less than 1 vol. %, less than 0.5 vol. %, less than 0.1 vol. %, or less than 0.01 vol. % of the one ore more other compounds, based on the total volume of the composition.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: $R=RL+k*(RU-RL)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

In addition to the definitions above, certain compounds described herein have one or more double bonds that can exist as either the Z or E isomer. The invention in certain embodiments encompasses these compounds as individual isomers in a substantially pure form as well as mixtures of various isomers, e.g., racemic mixtures of stereoisomer.

Current Sources of Isoprene

Isoprene currently is made naturally by rubber plants (typically *Hevea brasiliensis*) or is made synthetically from petroleum sources. When made naturally, the sap-like extract (known as latex and is a polymerized version of isoprene) is collected from the rubber plants and is the primary source of natural rubber. Because latex and natural rubber can be of varying quality (irregular molecular distribution), the synthetic analog of natural rubber or polyisoprene is often preferred due to its higher uniformity.

Chemically synthesized isoprene is made primarily from petroleum sources. The most common method involves stream cracking a petroleum stream to make ethylene which in turn is subsequently converted into isoprene. Other methods for making isoprene include isobutylene carbonylation and isopentane dehydrogenation. The resulting isoprene is produced and sold in different concentrations. Crude isoprene has a purity between 15% and 65%. Refined isoprene is defined as isoprene having a purity between 65% and 95%. High purity isoprene is defined as isoprene having a purity between 95% and 99.5%. Polymer grade isoprene is isoprene with a purity exceeding 99.5%.

As a consequence of how it is made, synthetic isoprene contains a number of impurities including various acetylenes and dienes such as cyclopentadiene and piperylene. Although these catalysts are undesirable as they inhibit polymerization, it is not often economical to entirely eliminate them and the purity of the isoprene is matched to the desired end product. For example, the isoprene purity required to make butyl rubber is substantially less that required to make SIS polymers (polymer grade).

Microbially Derived Gaseous Isoprene Compositions

The present invention provides microbial derived isoprene compositions and methods for making and purifying the same. Microbial-derived isoprene compositions differ from petroleum derived sources in that the compositions include virtually none of the following impurities: $C_2$-$C_5$ alkynes; cyclopentadiene, piperylene and 1,4-pentadiene.

In one aspect of the invention, a gaseous isoprene composition is provided. The composition comprises isoprene and water wherein the water is present in an amount that is at least about 70% of its saturation amount and the composition comprises 1 part per million or less of $C_2$-$C_5$ alkynes. Illustrative examples of $C_2$-$C_5$ alkynes include acetylene, isopropylacetylene, 1-pentyne, 2-pentyne, and 2-butyne.

In another aspect of the invention, another gaseous isoprene composition is provided. The composition comprises isoprene and water wherein the water is present in an amount that is at least about 70% of its saturation amount and the composition comprises 1 part per million or less of cyclopentadiene.

In another aspect of the invention, another gaseous isoprene composition is provided. The composition comprises isoprene and water wherein the water is present in an amount that is at least about 70% of its saturation amount and the composition comprises 1 part per million or less of piperylene.

In another aspect of the invention, another gaseous isoprene composition is provided. The composition comprises isoprene and water wherein the water is present in an amount that is at least about 70% of its saturation amount and the composition comprises 1 part per million or less of 1,4-pentadiene.

In another aspect of the invention, another gaseous isoprene composition is provided. The composition comprises isoprene and water wherein the water is present in an amount that is at least about 70% of its saturation amount and the composition comprises 1 part per million or less of each of $C_2$-$C_5$ alkynes, cyclopentadiene, piperylene, and 1,4-pentadiene.

In some embodiments, the gaseous isoprene composition comprises isoprene that is present between about 0.1% and about 15% by volume. In other embodiments, the isoprene is present between about 1 and 10% by volume. In still other embodiments, the isoprene is present between about 1 and 5% by volume. In yet other embodiments, the isoprene is present between about 5% and about 10% by volume. In further embodiments, the isoprene is present between in an amount greater than about 10% by volume.

In other embodiments, the gaseous isoprene composition comprises water in an amount that is greater than about 70%, 75%, 80%, 85%, 90%, 95% and 99% of its saturation amount. In still other embodiments, the gaseous isoprene composition comprises saturated water.

In other embodiments, the gaseous isoprene composition further comprises carbon dioxide that is present in an amount that is greater than about 0.04% by volume. In still other embodiments, the carbon dioxide is present in an amount that is greater than about 0.05%, 0.1%, 0.5%, 1.0%, and 5% by volume. In further embodiments, the carbon dioxide is present in an amount that is greater than about 10%, about 20%, about 30% by volume. In still further embodiments, the carbon dioxide is present in an amount that is between about 1% and about 35% by volume. In still other embodiments, the carbon dioxide is present in an amount that is between about 10% and about 30% by volume.

In other embodiments, the gaseous isoprene composition further comprises oxygen. In some embodiments, the oxygen is present in an amount that is less than about 20.9% by volume. In other embodiments, the oxygen is present in an amount that is between about 1% by volume and about 20% by volume. In other embodiments, the oxygen is present in an amount that is between about 8% and about 15% by volume. In other embodiments, the oxygen is present in an amount that is less than about 20%, 15%, 10%, 9%, 8%, 7%, 6%, 5%, 4%, 3%, and 2%. In still other embodiments, the oxygen is present in an amount that is less than about 1% by volume. In further embodiments, the oxygen is present between about 1% and about 15% by volume. In still further embodiments, the oxygen is present between about 5% and about 15% by volume.

In other embodiments, the gaseous isoprene composition further comprises nitrogen. In some embodiments, the nitrogen is present in an amount between about 50% and about 75% by volume. In further embodiments, the nitrogen is present in an amount that is greater than about 70%. In other embodiments, the nitrogen is present in an amount that is greater than about 75%, 76%, 77%, 78%, 79%, and 80%.

In other embodiments, the gaseous isoprene composition further comprises argon. In some embodiments, the argon is present in an amount that is less than about 0.9% by volume. In other embodiments, the argon is present in an amount that is greater than about 1.0% by volume.

In other embodiments, the gaseous isoprene composition further comprises ethanol. In some embodiments, the ethanol is present in an amount that is less than about 0.5% by volume. In other embodiments, the ethanol is present in an amount that is more than about 1% by volume.

In other embodiments, the microbial-derived gaseous isoprene composition may comprise: isoprene in an amount between about 0.1% and about 15% by volume; water in an amount that is greater than about 70% of its saturation amount; carbon dioxide in an amount that is between about 0.04% and about 35% by volume; oxygen in an amount that is between about 1% and about 20% by volume; nitrogen in an amount that is greater than about 50% by volume; argon in an amount that is less than about 0.9% by volume; ethanol in an amount that is less than about 0.5% by volume; 1 part per million or less of $C_2$-$C_5$ alkynes; 1 part per million or less of cyclopentadiene; 1 part per million or less of piperylene; and 1 part per million or less of 1,4-pentadiene.

In other embodiments, the microbial-derived gaseous isoprene composition may comprise: isoprene in an amount between about 0.1% and about 15% by volume; water in an amount that is greater than about 70% of its saturation amount; carbon dioxide in an amount that is between about 0.04% and about 35% by volume; oxygen in an amount that is between about 1% and about 20% by volume; nitrogen in an amount that is greater than about 50% by volume; argon in an amount that is greater than about 1.0% by volume; ethanol in an amount that is more than about 1% by volume; 1 part per million or less of $C_2$-$C_5$ alkynes; 1 part per million or less of cyclopentadiene; 1 part per million or less of piperylene; and 1 part per million or less of 1,4-pentadiene.

In certain other embodiments, another gaseous isoprene composition is provided. This composition comprises:

a. isoprene in an amount between about 0.1% and 15% by volume;
b. carbon dioxide in an amount between about 1% and 35% by volume; and,
c. water in an amount that is greater that about 70% of its saturation amount and wherein the gaseous isoprene composition comprises 1 part per million or less of $C_2$-$C_5$ alkynes. In other embodiments, the gaseous isoprene composition comprises 1 part per million or less of each of $C_2$-$C_5$ alkynes, cyclopentadiene, piperylene, and 1,4-pentadiene. In still other embodiments, the gaseous isoprene composition comprises saturated water. In yet other embodiments, the gaseous isoprene composition further comprises oxygen in an amount between about 8% and about 15% by volume or nitrogen in an amount between about 50% and 75% by volume or both.

The temperature of the above described gaseous compositions is at least 30° C. In some cases, the temperature is between about 30° C. and about 60° C. In other cases, the temperature is between about 30° C. and about 38° C.

The pressure of the above described gaseous compositions is between about 1 and about 2.5 atmospheres.

For some of the above described gaseous compositions, the temperature is between about 30° C. and about 35° C. and is at a pressure between about 1 and about 2.5 atmospheres.

Microbially Derived Liquid Isoprene Compositions

Using the methods described herein, the gaseous isoprene compositions of the present invention can be further purified to liquid isoprene. Thus in another aspect of the invention, a liquid isoprene composition is provided that results from the inventive methods. The resulting liquid isoprene composition comprises at least 65% isoprene by weight and wherein the liquid isoprene composition comprises 1 part per million or less of $C_2$-$C_5$ alkynes, cyclopentadiene, piperylene, and 1,4-pentadiene.

In some embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the liquid isoprene composition further comprises carbon dioxide. In some embodiments, the carbon dioxide is present in an amount that is between about 0.01% by weight and about 1% by weight. In other embodiments, the carbon dioxide is present in an amount that is between about 0.05% and about 1% by weight. In further embodiments, the carbon dioxide is present in an amount that is between about 0.1% and about 1% by weight. In still further embodiments, the carbon dioxide is present in an amount that is between about 0.2% and about 0.7% by weight.

In other embodiments, the liquid isoprene composition further comprises nitrogen. In some embodiments, the nitrogen is present in an amount that is between about 0.001% by weight and about 1% by weight. In other embodiments, the carbon dioxide is present in an amount that is between about 0.01% and about 0.5% by weight. In further embodiments, the carbon dioxide is present in an amount that is between about 0.05% and about 0.5% by weight.

In other embodiments, the liquid isoprene composition further comprises ethanol. In some embodiments, the ethanol is present in an amount that is greater than about 0.01% by weight. In other embodiments, the ethanol is present in an amount that is greater than about 0.1%, 0.2%, 0.3%, 0.4%, 0.5%, 0.6%, 0.7%, 0.8%, and 0.9% by weight. In further embodiments, the ethanol is present in an amount that is greater than about 1% by weight.

In other embodiments, the liquid isoprene composition may comprise water in an amount that is less than about 1%, 0.5%, 0.1%, and 0.05% by weight. In other embodiments, the liquid isoprene composition may comprise water in an amount that is less than about 500 ppm, 250 ppm, 100 ppm, and 50 ppm by weight. In other embodiments, the liquid isoprene composition may comprise water in an amount, by weight, that is less than the level of detection.

In other embodiments, the microbial-derived liquid isoprene composition may comprise: isoprene in an amount of at least about 65% to an amount greater than about 99.5% by weight; carbon dioxide in an amount that is between about 0.01% and about 1% by weight; nitrogen in an amount that is between about 0.001% and about 1% by weight; ethanol in an amount greater than about 0.01% to an amount greater than about 1% by weight; water in an amount that is less than about 1% by weight to an amount that is less than the level of detection; $C_2$-$C_5$ alkynes in an amount 1 part per million or less; cyclopentadiene in an amount 1 part per million or less; piperylene in an amount 1 part per million or less; and 1,4-pentadiene in an amount 1 part per million or less.

In certain other embodiments, another liquid isoprene composition is provided. This composition comprises:

a. isoprene in an amount greater than about 65% by weight;
b. ethanol in an amount greater than about 0.01% by weight; and,
c. carbon dioxide in an amount between about 0.01% and about 1% by weight wherein the liquid isoprene composition comprises 1 part per million or less of $C_2$-$C_5$ alkynes, cyclopentadiene and piperylene $C_2$-$C_5$ alkynes. In some embodiments, the isoprene is present in an amount greater than about 85% by weight. In still other embodiments, the isoprene is present in an amount greater than about 90% by weight. In further embodiments, the isoprene is present in an amount greater than about 90% by weight and ethanol is present in an amount that is between about 0.01% and about 1% by weight.

For some of the above described liquid isoprene compositions, the compositions have a temperature below −35° C. and a pressure between 0.01 and about 2 atmospheres. In other embodiments, the compositions have a temperature between −45° C. and about −85° C. and a pressure below about 1 atmosphere. In still further embodiments, the compositions have a temperature below −45° C. and a pressure below about 0.5 atmosphere.

Microbial Host Cells

Any microbial host cells capable of making isoprene can be used in the methods herein which would result in the inventive isoprene compositions.

Illustrative examples of suitable host cells are microbes that have been shown to make isoprene naturally. These strains include those described by U.S. Pat. No. 5,849,970 and include: *Bacillus amyloliquiefaciens; Bacillus cereus; Bacillus subtillis* 6051; *Basillus substillis* 23059; *Bacillus subtillis* 23856; *Micrococcus luteus; Rhococcus rhodochrous; Acinetobacter calcoacetiucus; Agrobacternum rhizogenes; Escherichia coli; Erwinia herbicola; Pseudomonoas aeruginosa*; and *Psuedomonas citronellolis*. However, microbes that make isoprene naturally are produced at extremely low levels.

Isoprene is made from isopentenyl pyrophosphate (IPP) by isoprene synthase. Because all microbial host cells are capable of making IPP, any host cells can be made to make isoprene by the insertion of isoprene synthase into its genome. Illustrative examples of suitable nucleotide sequences include but are not limited to: (EF638224, *Populus alba*); (AJ294819, *Populus alba*×*Populus tremula*); (AM410988, *Populus nigra*); (AY341431, *Populus tremuloides*); (EF147555, *Populus trichocarpa*); and (AY316691, *Pueraria montana* var. *lobata*). The addition of a heterologous isoprene synthase to a microbial host cells that make isoprene naturally will improve isoprene yields of natural isoprene producers as well.

Any suitable microbial host cell can be genetically modified to make isoprene. A genetically modified host cell is one in which nucleic acid molecules have been inserted, deleted or modified (i.e., mutated; e.g., by insertion, deletion, substitution, and/or inversion of nucleotides), to produce isoprene. Illustrative examples of suitable host cells include any archae, bacterial, or eukaryotic cell. Examples of archae cells include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae species include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium.*

Examples of bacterial cells include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*.

Illustrative examples of bacterial species include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of species with non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of eukaryotic cells include but are not limited to fungal cells. Examples of fungal cells include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic species include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of species with non-pathogenic strains include but are not limited to: *Fusarium graminearum, Fusarium venenatum, Pichia pastoris, Saccaromyces boulardi,* and *Saccaromyces cerevisiae.*

In some embodiments, the host cells of the present invention have been designated by the Food and Drug Administration as GRAS or Generally Regarded As Safe. Illustrative examples of such strains include: *Bacillus subtilis, Lactibacillus acidophilus, Lactobacillus helveticus*, and *Saccharomyces cerevisiae.*

In addition to the heterologous nucleic acid encoding an isoprene synthase, the microbial host cell can be further modified to increase isoprene yields. These modifications include but are not limited to the expression of one or more heterologous nucleic acid molecules encoding one or more enzymes in the mevalonate or DXP pathways.

MEV Pathway

Figure 3:
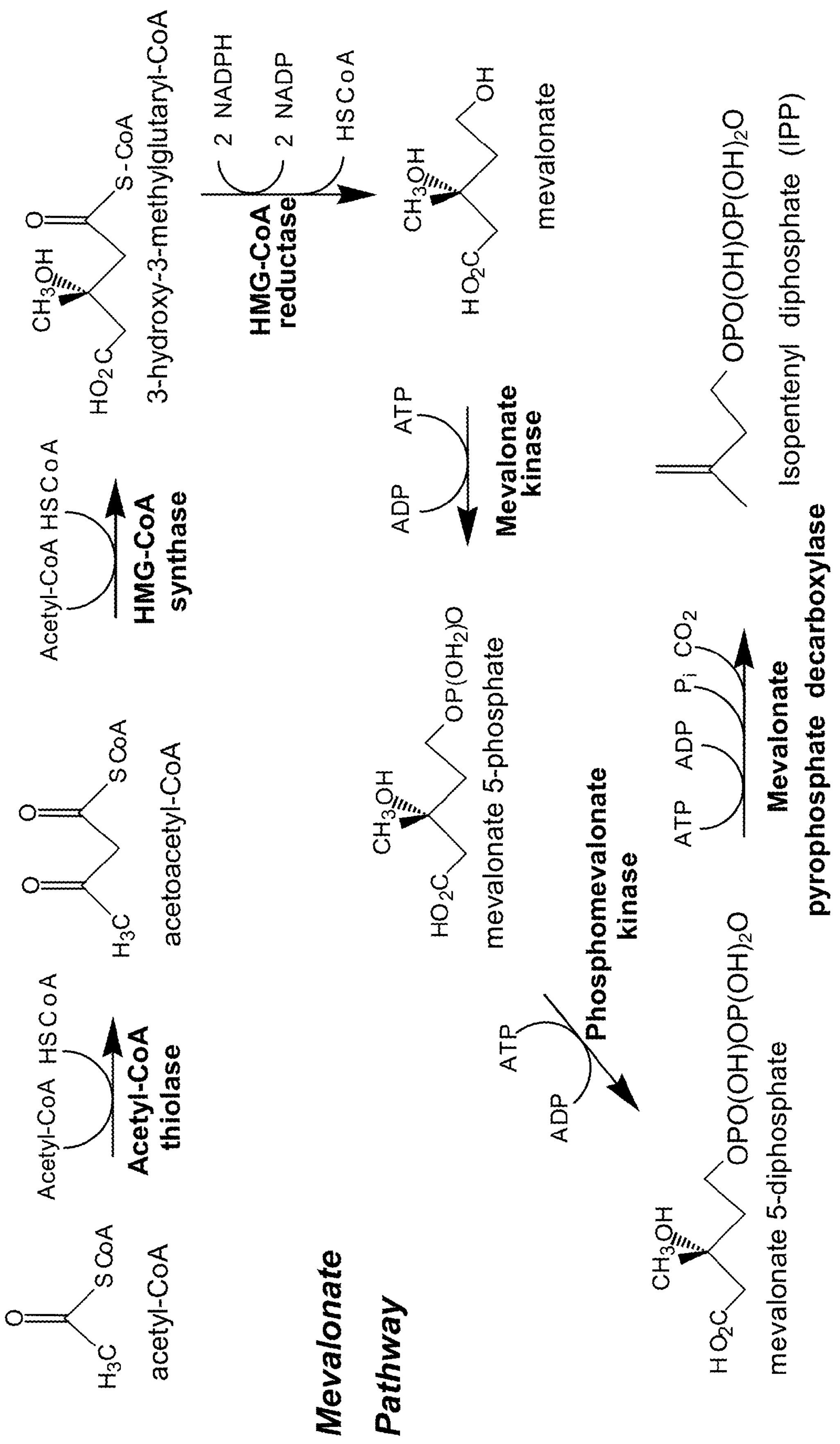
FIG. 3 is a schematic representation of the mevalonate ("MEV") pathway for the production of isopentenyl diphosphate ("IPP").

A schematic representation of the MEV pathway is described in FIG. 3. In general, the pathway comprises six steps.

In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). Illustrative examples of nucleotide sequences include but are not limited to the following GenBank accession numbers and the organism from which the sequences derived: (NC_000913 REGION: 2324131 . . . 2325315; *Escherichia coli*), (D49362; *Paracoccus denitrificans*), and (L20428; *Saccharomyces cerevisiae*).

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Illustrative examples of nucleotide sequences include but are not limited to: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In the third step, HMG-CoA is enzymatically converted to mevalonate. An enzyme known to catalyze this step is, for example, HMG-CoA reductase. Illustrative examples of nucleotide sequences include but are not limited to: (NM_206548; *Drosophila melanogaster*), (NC_002758, Locus tag SAV2545, GeneID 1122570; *Staphylococcus aureus*), (NM_204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*).

In the fourth step, mevalonate is enzymatically phosphorylated to form mevalonate 5-phosphate. An enzyme known to catalyze this step is, for example, mevalonate kinase. Illustrative examples of nucleotide sequences include but are not limited to: (L77688; *Arabidopsis thaliana*), and (X55875; *Saccharomyces cerevisiae*).

In the fifth step, a second phosphate group is enzymatically added to mevalonate 5-phosphate to form mevalonate 5-pyrophosphate. An enzyme known to catalyze this step is, for example, phosphomevalonate kinase. Illustrative examples of nucleotide sequences include but are not limited to: (AF429385; *Hevea brasiliensis*), (NM_006556; *Homo sapiens*), and (NC_001145. complement 712315 . . . 713670; *Saccharomyces cerevisiae*).

In the sixth step, mevalonate 5-pyrophosphate is enzymatically converted into IPP. An enzyme known to catalyze this step is, for example, mevalonate pyrophosphate decarboxylase. Illustrative examples of nucleotide sequences include but are not limited to: (X97557; *Saccharomyces cerevisiae*), (AF290095; *Enterococcus faecium*), and (U49260; *Homo sapiens*).

DXP Pathway

A schematic representation of the DXP pathway is described in FIG. 4. In general, the DXP pathway comprises seven steps. In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Illustrative examples of nucleotide sequences include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP_0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula1*), and (NC_003076, locus tag AT5G11380; *Arabidopsis thaliana*).

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SCO5694; *Streptomyces coelicolor* A3(2)), (NC_007493, locus tag RSP_2709; *Rhodobacter sphaeroides* 2.4.1), and (NC_007492, locus tag Pfl_1107; *Pseudomonas fluorescens* PfO-1).

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Illustrative examples of nucleotide sequences include but are not limited to: (AF230736; *Escherichia coli*), (NC_007493, locus_tag RSP_2835; *Rhodobacter sphaeroides* 2.4.1), (NC_003071, locus_tag AT2G02500; *Arabidopsis thaliana*), and (NC_002947, locus_tag PP1614; *Pseudomonas putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Illustrative examples of nucleotide sequences include but are not limited to: (AF216300; *Escherichia coli*) and (NC_007493, locus_tag RSP_1779; *Rhodobacter sphaeroides* 2.4.1).

In the fifth step, 4-diphosphocytidyl-2C-methyl-D-erythritol-2-phosphate is converted to 2C-methyl-D-erythritol 2, 4-cyclodiphosphate. An enzyme known to catalyze this step is, for example, 2C-methyl-D-erythritol 2, 4-cyclodiphosphate synthase. Illustrative examples of nucleotide sequences include but are not limited to: (AF230738; *Escherichia coli*), (NC_007493, locus_tag RSP_6071; *Rhodobacter sphaeroides* 2.4.1), and (NC_002947, locus_tag PP1618; *Pseudomonas putida* KT2440).

In the sixth step, 2C-methyl-D-erythritol 2, 4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Illustrative examples of nucleotide sequences include but are not limited to: (AY033515; *Escherichia coli*), (NC_002947, locus_tag PP0853; *Pseudomonas putida* KT2440), and (NC_007493, locus_tag RSP_2982; *Rhodobacter sphaeroides* 2.4.1).

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Illustrative examples of nucleotide sequences include but are not limited to: (AY062212; *Escherichia coli*) and (NC_002947, locus_tag PP0606; *Pseudomonas putida* KT2440).

In some embodiments, "cross talk" (or interference) between the host cell's own metabolic processes and those processes involved with the production of IPP as provided by the present invention are minimized or eliminated entirely. For example, cross talk is minimized or eliminated entirely when the host microorganism relies exclusively on the DXP pathway for synthesizing IPP, and a MEV pathway is introduced to provide additional IPP. Such host organisms would not be equipped to alter the expression of the MEV pathway enzymes or process the intermediates associated with the MEV pathway. Organisms that rely exclusively or predominately on the DXP pathway include, for example, *Escherichia coli.*

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the naturally occurring DXP pathway enzymes.

In other embodiments, the host cell produces IPP via the DXP pathway, either exclusively or in combination with the MEV pathway. In other embodiments, a host's MEV pathway is functionally disabled so that the host cell produces IPP exclusively through a heterologously introduced DXP pathway. The MEV pathway can be functionally disabled by disabling gene expression or inactivating the function of one or more of the naturally occurring MEV pathway enzymes.

Methods for genetically modifying host organisms and their cultivation have been previously described. Illustrative examples include U.S. Pat. Nos. 6,689,593; 7,172,886; 7,183,089; U.S. Patent Publication Nos. US 2008/0171378; US 2008/0274523; and US 2009/0203102 and PCT Publication Nos. WO 2007/139924; WO 2009/076676; WO 2010/003007; and WO 2009/132220, which are all incorporated herein by reference in their entirety. Additional methods for modifying host organisms to make isoprene are also provided in the Examples below.

Purification and Recovery of Microbially Derived Gaseous Isoprene

The present invention provides methods for handling a gaseous isoprene composition produced from the microbial host cells. When the resulting gaseous isoprene compositions or the above-described gaseous isoprene compositions are treated with the following methods, then the results are the liquid isoprene compositions described above.

In one aspect, a system for purifying isoprene without extractive distillation is provided. Extractive distillation is defined as distillation in the presence of a solvent that forms no azeotrope with other components in the mixture and is used to separate mixtures that cannot be separated by simple distillation because the volatility of at least two of the components in the mixture is nearly the same, causing them to evaporate at nearly the same temperature at a similar rate. Generally miscible, high boiling, and relatively non-volatile, the extraction distillation solvent interacts differently with the components in the mixture enabling the mixture to be separated by normal distillation. Extractive distillation is almost always used in purifying petroleum-derived isoprene. Because extractive distillation requires special equipment and is inherently energy intensive, it is substantial part of the costs associated with making isoprene. In many embodiments of the present invention, the resulting isoprene compositions do not include trace amounts of an extraction distillation solvent because extractive distillation solvents are not used. Illustrative examples of such solvents include but are not limited to acetonitrile and dimethylformamide.

FIG. 1 is a schematic representation of an exemplary separation system. Host cells are cultivated in a bioreactor and the isoprene produced by the cells vaporizes and forms a gaseous isoprene composition (1). Optionally, the gaseous isoprene composition may pass through a drying process to remove some of the water vapor (not shown). The gaseous isoprene composition (1) is directed to a first chiller 102 which cools the gaseous isoprene composition to a temperature between about 10° C. and about −15° C. The cooled gaseous isoprene composition (7) then passes through drum 104, where the water vapor in the gaseous isoprene composition condenses into a liquid and discharged from the process (5). The exiting gaseous isoprene composition (8) may pass through a drying process to remove any remaining water (not shown). The gaseous isoprene composition (8) is directed to a second chiller 106 further cooling the composition to a temperature below −35° C. The resulting liquid isoprene composition (9) flows to drum 108. Optionally, the bottom stream (10) from drum 108 may then be passed to nitrogen stripper 110 while the top stream (11) is recycled back to the first chiller 102 to assist in (or to serve as the refrigerant for) chilling the incoming gaseous isoprene (1) and then exiting a by-product stream (6). Substantially pure nitrogen (2) is introduced into nitrogen stripper 110 whereby the liquid isoprene composition (3) is recovered and the by-product nitrogen gas (4) can be discharged or recovered in a subsequent recovery step (not shown).

In another embodiment, the system comprises:

a. a bioreactor capable of culturing a plurality of host cells, preferably the bioreactor has a capacity of greater than 100 liters;

b. a first chiller and flash drum operably connected to the overhead stream of the bioreactor, the first chiller preferably capable of operating in a temperature range of between 10° C. and −15° C.;

c. a second chiller and flash drum operably connected to the overhead stream exiting from the first chiller and flash drum, the second chiller preferably capable of operating in a temperature below −35° C., for example between about −65° C. and about −85° C.;

d. optionally, the exiting overhead stream from the second chiller and flash drum may be operably connected to the inlet of the refrigerant or cooling stream of the first chiller; and e. optionally, the condensed stream exiting from the second chiller and flash drum may be operably connected to a nitrogen stripper.

In another aspect, method for recovering isoprene using such a system is provided. The method comprises:

a. obtaining a first gaseous composition comprising isoprene and water wherein the gaseous composition comprises 1 part per million or less of $C_2$-$C_5$ alkynes;

b. flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises about 3% by weight or less of water;

c. flowing the second gaseous composition through a second chiller wherein the second chiller has a temperature below −35° C.; and d. collecting the resulting liquid isoprene composition.

In other embodiments, the method for recovering isoprene comprises reducing the water content present in the first gaseous composition by flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises less than about 3% by weight of water. In other embodiments, the second gas composition comprises less than about 2% by weight of water, less than 1%, 0.5%, 0.1%, and 0.05% by weight. In other embodiments, the second gas composition comprises less than about 500 ppm by weight of water, less than 250 ppm, 100 ppm and 50 ppm by weight.

In another aspect, method for recovering isoprene using such a system is provided. The method comprises:

a. obtaining a first gaseous composition comprising isoprene and water wherein the gaseous composition comprises 1 part per million or less of $C_2$-$C_5$ alkynes;

b. flowing the first gaseous composition through a first chiller wherein the first chiller has a temperature of between about 10° C. and about −15° C. thereby resulting in a second gaseous composition and wherein the second gaseous composition comprises less water than the first gaseous composition, for example the second gas composition comprises about 3% by weight or less of water;

c. flowing the second gaseous composition through a second chiller wherein the second chiller has a temperature below −35° C. thereby resulting in a liquid isoprene composition, wherein the liquid isoprene composition comprises less of one or more of the following components than the second gaseous composition, comprising:

i. water in amount less than about 1% by weight or less;

ii. carbon dioxide in amount less than 1% by weight;

iii. nitrogen in amount less than 1% by weight; and d. collecting the resulting liquid isoprene composition.

In some embodiments, the method further comprises nitrogen stripping the liquid isoprene composition. This nitrogen stripping may be accomplished by any suitable method including passing a substantially pure nitrogen stream through the liquid isoprene enriched composition. This nitrogen stream serves to further remove dissolved gases (such, as for example oxygen, carbon dioxide, nitrogen, and argon) and or/remaining water. In other embodiments, nitrogen stripping of the liquid isoprene composition may comprise removing: dissolved oxygen to levels less than about 1%, 0.5%, 0.1%, and 0.05% by weight; dissolved carbon dioxide to levels less than about 1%, 0.5%, 0.1%, and 0.05% by weight; dissolved nitrogen to levels less than about 1%, 0.5%, 0.1%, and 0.05% by weight; dissolved argon to levels less than about 1%, 0.5%, 0.1%, and 0.05% by weight; and any remaining water to levels less than about 1%, 0.5%, 0.1%, 0.05% by weight to levels lower than the level of detection.

In some embodiments, the method further comprises extracting hydrocarbon impurities at some point in the purifying isoprene process. This hydrocarbon extraction may be accomplished by passing a portion or all of the first gaseous composition, second gaseous composition and/or the liquid isoprene composition over or through a modified zeolite membrane and/or molecular sieve. The zeolite membrane and/or molecular sieves may be modified to selectively adsorb either isoprene and not the other hydrocarbons present in the treated composition or vice versa (adsorb other hydrocarbons in the treated composition and not isoprene). In some embodiments, the zeolites and/or molecular sieves are modified by carbonization to provide the selected adsorbtivity. In some embodiments, the zeolites may be L-type, Y-type, ZSM-5, and/or beta-type. In some embodiments a method for enhancing the selectivity of a zeolite by controlled carbonization as detailed in U.S. Pat. No. 7,041,616, which is hereby incorporated in its entirety by reference, may be used.

In other embodiments, the first gaseous composition further comprises carbon dioxide. In still other embodiments, the first gaseous composition further comprises oxygen. In still other embodiments, the first gaseous composition further comprises nitrogen.

In other embodiments, the first gaseous composition comprises 1 part per million or less of $C_2$-$C_5$ alkynes and cyclopentadiene. In further embodiments, the first gaseous composition further comprises 1 part per million or less of $C_2$-$C_5$ alkynes and piperylene. In still other embodiments, the first gaseous composition comprises 1 part per million or less of $C_2$-$C_5$ alkynes and 1,4-pentadiene. In still other embodiments, the first gaseous composition comprises 1 part per million or less of $C_2$-$C_5$ alkynes, cyclopentadiene, piperylene, and 1,4-pentadiene.

In other embodiments, the first gaseous composition is flowed through a drier prior to flowing through the first chiller. In still other embodiments, the first gaseous composition is flowed through a drier after flowing through the first chiller but prior to flowing through the second chiller.

In other embodiments, the first chiller has a temperature of about −5° C. In other embodiments, the first chiller is cooled using a propylene refrigeration system. In still other embodiments, the first chiller is cooled using an ammonium refrigeration system.

In other embodiments, the second chiller has a temperature less than about −50° C. In other embodiments, the second chiller has a temperature of about −60° C. to about −85° C. In still other embodiments, the second chiller has a temperature of less than about −65° C. In still other embodiments, the second chiller has a temperature between about −35° C. and about −85° C.

In other embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the second chiller is cooled using an ethylene refrigeration system.

In another aspect, another method is provided. The method comprises:

a. culturing a plurality of host cells capable of making isoprene;
b. forming a first gaseous composition comprising isoprene and water wherein the water is present in an amount greater than about 70% of its saturation amount;
c. subjecting the first gaseous composition to a first cooling step whereby substantially all of the water is removed from the first gaseous composition resulting a second gaseous composition;
d. subjecting the second gaseous composition to a second cooling step whereby a liquid isoprene composition is collected.

In some embodiments, the method further comprises nitrogen stripping the liquid isoprene composition.

In other embodiments, the first gaseous composition further comprises carbon dioxide. In still other embodiments, the first gaseous composition further comprises oxygen. In still other embodiments, the first gaseous composition further comprises nitrogen.

In other embodiments, the first gaseous composition comprises 1 part per million or less of $C_2$-$C_5$ alkynes and cyclopentadiene. In further embodiments, the first gaseous composition further comprises 1 part per million or less of $C_2$-$C_5$ alkynes and piperylene. In still other embodiments, the first gaseous composition comprises 1 part per million or less of $C_2$-$C_5$ alkynes and 1,4-pentadiene. In still other embodiments, the first gaseous composition comprises 1 part per million or less of $C_2$-$C_5$ alkynes, cyclopentadiene, piperylene, and 1,4-pentadiene.

In other embodiments, the first gaseous composition is subjected through a drier prior to the first cooling step. In still other embodiments, the first gaseous composition is subjected through a drier after the first cooling step but prior to the second cooling step.

In other embodiments, the first cooling step cools the first gaseous isoprene composition to a temperature between about 10° C. and about −15° C., between about 10° C. and about −10° C., about 5° C. and about −5° C., and about 5° C. and about −10° C.

In other embodiments, the first cooling step uses a propylene refrigeration system. In still other embodiments, the first cooling step uses chiller an ammonium refrigeration system.

In other embodiments, the second cooling step cools the second gaseous isoprene composition to a temperature less than −35° C. In other embodiments, the second cooling step cools the second gaseous isoprene composition to a temperature less than about −50° C. In still other embodiments, the second cooling step cools the second gaseous isoprene composition to a temperature about −60° C. to about −85° C. In still further embodiments, the second cooling step cools the second gaseous isoprene composition to a temperature of less than about −65° C.

In other embodiments, the second cooling step uses an ethylene refrigeration system.

In other embodiments, the liquid isoprene composition comprises at least about 70%, 75%, 80%, 85%, and 90% isoprene by weight. In other embodiments, the liquid isoprene comprises at least about 95%, 96%, 97%, 98%, 99% and 99.5% isoprene by weight. In still other embodiments, the liquid isoprene composition comprises isoprene in an amount that is greater than about 99.5% by weight.

In other embodiments, the host cells are are selected from the genus *Bacillus, Escherichia* or *Acinetobacter*. In still other embodiments, the host cells are *Escherichia coli*. In further embodiments, the host cells are yeast. In still further embodiments, the host cells are *Saccharomyces cerevisiae*.

In another aspect, another method is provided. The method comprises:

a. contacting a plurality of host cells capable of making isoprene in an aqueous medium wherein the aqueous medium is in contact with an immiscible organic liquid and the aqueous medium, the host cells, and the immiscible organic liquid is in a closed vessel; and
b. culturing the host cells in the aqueous medium whereby the host cells make isoprene and the isoprene is captured in the immiscible organic liquid.

In some embodiments, the method further comprises separating the immiscible organic liquid from the aqueous medium and separating the isoprene from the immiscible organic liquid.

In other embodiments, the immiscible organic liquid is selected from butyl acetate, ethyl acetate, isopropyl myristate, methyl isobutyl ketone, methyl oleate, and toluene. In certain embodiments, the solvent is butyl acetate. In other embodiments, the immiscible organic liquid is isopropyl myristrate.

In other embodiments, the isoprene is separated from the immiscible organic liquid by heating the immiscible organic liquid to a temperature above 34° C.

The resulting gaseous isoprene composition can then be further purified using the methods described above.

Figure 2:
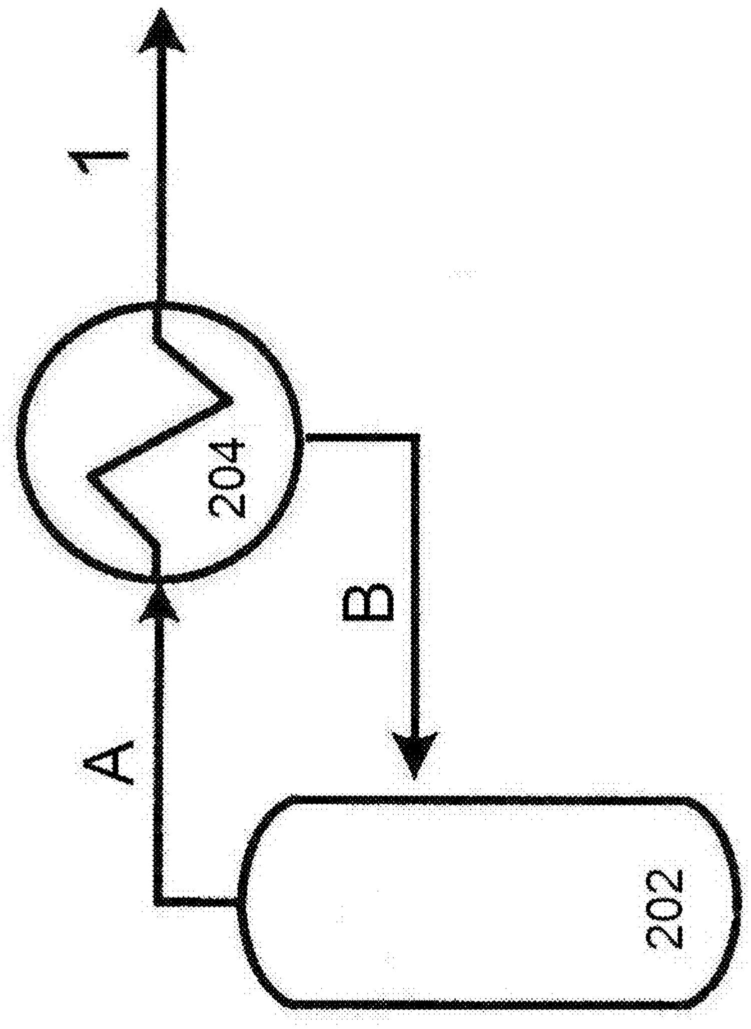
FIG. 2 is another schematic representation of another exemplary separation system.

In another aspect, a system for making microbial isoprene is provided. An illustrative example of such a system is shown in FIG. 2. Bioreactor 202 is a closed system where host cells capable of making isoprene are cultivated in an aqueous medium and with an immiscible organic liquid on top of the aqueous medium. Because bioreactor 202 is a closed system, the isoprene produced by the host cells is captured by the immiscible organic liquid. The isoprene-enriched immiscible organic liquid (A) may then directed be directed to any suitable gas-liquid separation method. In this example, the isoprene-enriched immiscible organic liquid is directed to a heater 204 which volatizes the isoprene into a gaseous isoprene composition (1). This gaseous isoprene composition (1) can then be further purified using the sytems and methods described above. The immiscible organic liquid (B) can optionally be recycled and used in subsequent bioreactions to make isoprene.

In another embodiment, the system comprises:

a. a closed vessel;

b. an aqueous medium, within the vessel, forming a first phase;

c. a plurality of host cells, within the aqueous medium, capable of making isoprene; and, d. a liquid organic second phase, capable of capturing the isoprene made by the host cells, in contact with the first phase.

In some embodiments, the immiscible organic liquid is selected from butyl acetate, ethyl acetate, isopropyl myristate, methyl isobutyl ketone, methyl oleate, and toluene. In certain embodiments, the solvent is butyl acetate. In other embodiments, the immiscible organic liquid is isopropyl myristrate.

In other embodiments, the host cells are selected from the genus *Bacillus, Escherichia* or *Acinetobacter*. In still other embodiments, the host cells are *Escherichia coli*. In further embodiments, the host cells are yeast. In still further embodiments, the host cells are *Saccharomyces cerevisiae*.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

In the following examples, efforts have been made to ensure accuracy with respect to numbers used (for example, amounts, temperature, and so on), but variation and deviation can be accommodated, and in the event a clerical error in the numbers reported herein exists, one of ordinary skill in the arts to which this invention pertains can deduce the correct amount in view of the remaining disclosure herein. Unless indicated otherwise, temperature is reported in degrees Celsius, and pressure is at or near atmospheric pressure at sea level. All reagents, unless otherwise indicated, were obtained commercially. The following examples are intended for illustrative purposes only and do not limit in any way the scope of the present invention.

Example 1

This example describes methods for detecting isoprene trapped in an immiscible organic liquid in a closed fermentation system.

In this example, isopropyl myristate (IPM) and solutions of IPM spiked with 103 mg/L, 10.3 mg/L and 0 mg/L isoprene were prepared and stored in 100 ml capped media bottles.

125 ml unbaffled flasks with screw caps/septa were set up in triplicate. The flasks contained 40 ml medium (Yeast Nitrogen Base media with 4% galactose, 0.2% glucose, Leu) inoculated with overnight yeast culture (which does not make isoprene) grown to an OD=0.05 with 8 ml of IPM solutions with the various concentrations of isoprene. The sealed flasks were incubated for 72 hours at 30° C. and 200 rpm.

Post-incubation, the IPM overlay was phase-separated by manual transfer to primary GC vials, then transferred to secondary GC vials and run undiluted on GC-FID. In addition to samples from flasks, the original solutions of 103 and 10.3 mg/L isoprene in IPM (NOT shaken for 72 hours at 200 rpm, 30° C.) were also analyzed.

Figure 5:
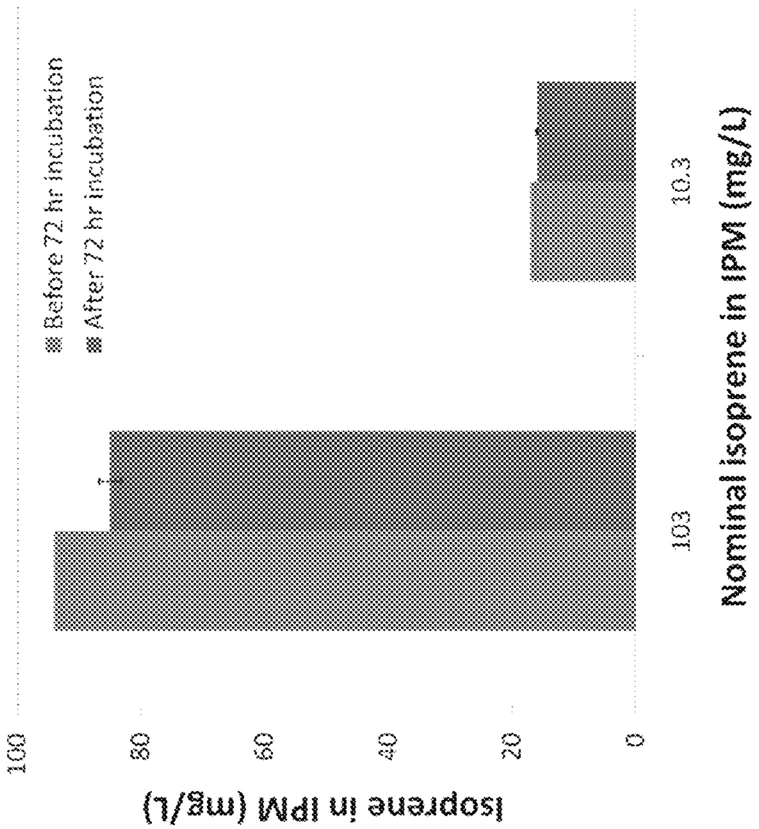
FIG. 5 shows the recovery of isoprene from an immiscible organic liquid (isopropyl myristate) from a closed fermentation system.

As shown by FIG. 5, over 90% of the spiked isoprene was recovered from the IPM layer. Cell growth for cultures with 103, 10.3, and 0 mg/L isoprene in the IPM layer was indistinguishable.

Example 2

This example describes methods for making nucleic acids for expressing in *Saccharomyces cerevisiae* heterologous isoprene synthases.

Genomic DNA was isolated from *Saccharomyces cerevisiae* strains Y002 (CEN.PK2 background MATA ura3-52 trp1-289 leu2-3,112 his3Δ1 MAL2-8C SUC2) (van Dijken et al. (2000) Enzyme and Microbial Technology 26:706-714), Y007 (S288C background MATA trp1Δ63) (ATCC number 200873), Y051 (S288C background), and EG123 (ATCC number 204278). The strains were grown overnight in liquid medium containing 1% Yeast extract, 2% Bacto-peptone, and 2% Dextrose (YPD medium). Cells were isolated from 10 mL liquid cultures by centrifugation at 3,100 rpm, washing of cell pellets in 10 mL ultra-pure water, and re-centrifugation. Genomic DNA was extracted using the Y-DER yeast DNA extraction kit (Pierce Biotechnologies, Rockford, Ill.) as per manufacturer's suggested protocol. Extracted genomic DNA was re-suspended in 100 uL 10 mM Tris-Cl, pH 8.5, and $OD_{260/280}$ readings were taken on a ND-1000 spectrophotometer (NanoDrop Technologies, Wilmington, Del.) to determine genomic DNA concentration and purity.

DNA amplification by Polymerase Chain Reaction (PCR) was done in an Applied Biosystems 2720 Thermocycler (Applied Biosystems Inc, Foster City, Calif.) using the Phusion High Fidelity DNA Polymerase system (Finnzymes OY, Espoo, Finland) as per manufacturer's suggested protocol. Upon the completion of a PCR amplification of a DNA fragment that was to be inserted into the pCR®4Blunt-TOPO vector (Invitrogen, Carlsbad, Calif.), A nucleotide overhangs were created by adding 1 uL of Qiagen Taq Polymerase (Qiagen, Valencia, Calif.) to the reaction mixture and performing an additional 10 minute, 72° C. PCR extension step, followed by cooling to 4° C. Upon completion of a PCR amplification, 8 uL of a 50% glycerol solution was added to the reaction mix.

Agarose gel electrophoresis was performed using a 1% TBE (0.89 M Tris, 0.89 M Boric acid, 0.02 M EDTA sodium salt) agarose gel containing 0.5 μg/mL ethidium bromide, at 120 V, 400 mA for 30 minutes. DNA bands were visualized using ultraviolet light. DNA bands were excised from the gel with a sterile razor blade, and the excised DNA was gel purified using the Zymoclean Gel DNA Recovery Kit (Zymo Research, Orange, Calif.) according to manufacturer's suggested protocols. The purified DNA was eluted into 10 uL ultra-pure water, and $OD_{260/280}$ readings were taken on a ND-1000 spectrophotometer to determine DNA concentration and purity.

Ligations were performed using 100-500 µg of purified PCR product and High Concentration T4 DNA Ligase (New England Biolabs, Ipswich, Mass.) as per manufacturer's suggested protocol. For plasmid propagation, ligated constructs were transformed into *Escherichia coli* DH5α chemically competent cells (Invitrogen, Carlsbad, Calif.) as per manufacturer's suggested protocol. Positive transformants were selected on solid media containing 1.5% Bacto Agar, 1% Tryptone, 0.5% Yeast Extract, 1% NaCl, and an appropriate antibiotic. Isolated transformants were grown for 16 hours in liquid LB medium containing 50 µg/mL carbenicillin or kanamycin antibiotic at 37° C., and plasmid was isolated and purified using a QIAprep Spin Miniprep kit (Qiagen, Valencia, Calif.) as per manufacturer's suggested protocol. Constructs were verified by performing diagnostic restriction enzyme digestions, resolving DNA fragments on an agarose gel, and visualizing the bands using ultraviolet light. Select constructs were also verified by DNA sequencing, which was done by Elim Biopharmaceuticals Inc. (Hayward, Calif.).

Expression plasmid pAM353 was generated by inserting a nucleotide sequence encoding a β-farnesene synthase into the pRS425-Gall vector (Mumberg et. al. (1994) *Nucl. Acids. Res.* 22(25): 5767-5768). The nucleotide sequence insert was generated synthetically, using as a template the coding sequence of the β-farnesene synthase gene of *Artemisia annua* (GenBank accession number AY835398) codon-optimized for expression in *Saccharomyces cerevisiae* (SEQ ID NO: 1). The synthetically generated nucleotide sequence was flanked by 5' BamHI and 3' XhoI restriction sites, and could thus be cloned into compatible restriction sites of a cloning vector such as a standard pUC or pACYC origin vector. The synthetically generated nucleotide sequence was isolated by digesting to completion the construct using BamHI and XhoI restriction endonucleases. The reaction mixture was resolved by gel electrophoresis, the approximately 1.7 kb DNA fragment comprising the β-farnesene synthase coding sequence was gel purified, and the isolated DNA fragment was ligated into the BamHI XhoI restriction site of the pRS425-Gall vector, yielding expression plasmid pAM353.

Expression plasmid pAM404 was generated by inserting a nucleotide sequence encoding the β-farnesene synthase of *Artemisia annua* (GenBank accession number AY835398) codon-optimized for expression in *Saccharomyces cerevisiae* into vector pAM178 (SEQ ID NO: 2). The nucleotide sequence encoding the β-farnesene synthase was PCR amplified from pAM353 using primers 52-84 pAM326 BamHI (SEQ ID NO: 21) and 52-84 pAM326 NheI (SEQ ID NO: 22). The resulting PCR product was digested to completion using BamHI and NheI restriction endonucleases, the reaction mixture was resolved by gel electrophoresis, the approximately 1.7 kb DNA fragment comprising the β-farnesene synthase coding sequence was gel purified, and the isolated DNA fragment was ligated into the BamHI NheI restriction site of vector pAM178, yielding expression plasmid pAM404.

Plasmid Genetrix2080 was generated by inserting a nucleotide sequence encoding an isoprene synthase into vector pUC19. The insert was generated synthetically as two approximately equal sized DNA fragments, fragment 2080_1 (SEQ ID NO: 3) and fragment 2080_2 (SEQ ID NO: 4), using as a template the coding sequence of the isoprene synthase gene of Kudzu codon-optimized for expression in *Saccharomyces cerevisiae*. Each DNA fragment was flanked by LguI restriction sites, and comprised a 40 base pair overlapping sequence at one end. The synthetically generated DNA fragments were blunt ligated into the SmaI restriction site of the pUC19 cloning vector, from which the two inserts were excised again by digesting to completion 500 µg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_494 (SEQ ID NO: 79) and TRIX_L_495 (SEQ ID NO: 80) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2080.

Plasmid Genetrix2081 was generated by inserting a nucleotide sequence encoding an isoprene synthase into vector pUC19. The insert was generated synthetically as two approximately equal sized DNA fragments, fragment 2081_1 (SEQ ID NO: 5) and fragment 2081_2 (SEQ ID NO: 6), using as a template the coding sequence of the isoprene synthase gene of *Populus nigra* codon-optimized for expression in *Saccharomyces cerevisiae*. Each DNA fragment was flanked by LguI restriction sites, and comprised a 30 base pair overlapping sequence at one end. The synthetically generated DNA fragments were blunt ligated into the SmaI restriction site of the pUC19 cloning vector, from which the two inserts were excised again by digesting to completion 500 µg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_497 (SEQ ID NO: 81) and TRIX_L_498 (SEQ ID NO: 82) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2081.

Plasmid Genetrix2082 was generated by inserting a nucleotide sequence encoding an isoprene synthase into vector pUC19. The insert was generated synthetically as two approximately equal sized DNA fragments, fragment 2082_1 (SEQ ID NO: 7) and fragment 2082_2 (SEQ ID NO: 8), using as a template the coding sequence of the isoprene synthase gene of *Populus alba×Populus tremula* codon-optimized for expression in *Saccharomyces cerevisiae*. Each DNA fragment was flanked by LguI restriction sites, and comprised a 40 base pair overlapping sequence at one end. The synthetically generated DNA fragments were blunt ligated into the SmaI restriction site of the pUC19 cloning vector, from which the two inserts were excised again by digesting to completion 500 μg of the construct using LguI restriction endonuclease (Fermentas, Glen Burnie, Md.). The restriction endonuclease was heat inactivated for 20 minutes at 65° C., and the DNA fragments were stitched together by a first round of PCR amplification (one cycle of denature at 98° C. for 2 minutes; 5 cycles of denature at 98° C. for 30 seconds and anneal/extend at 72° C. for 30 seconds per kilobase PCR product; no primers were used). Samples were placed on ice, 0.5 uM of each terminal primer TRIX_L_500 (SEQ ID NO: 83) and TRIX_L_501 (SEQ ID NO: 84) were added to the reaction mixture, and a second round of PCR amplification was performed (one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.). The reaction mixture was resolved by gel electrophoresis, the assembled DNA fragment was gel purified, treated with T4 polynucleotide kinase (PNK) (New England Biolabs, Ipswich, Mass.), and blunt ligated into the SmaI restriction site of vector pUC19, yielding plasmid Genetrix2082.

Figure 6:
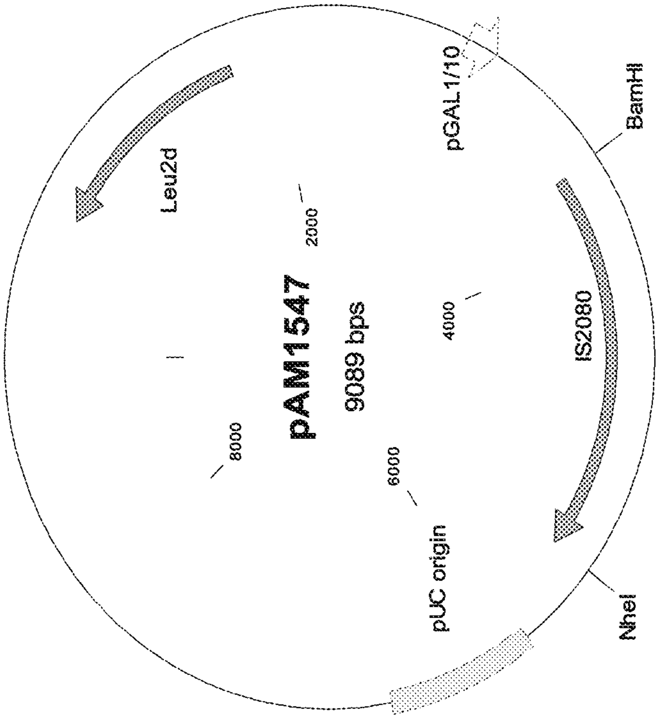
FIG. 6 shows a map of plasmid pAM1547.

Expression plasmid pAM1547 was generated by replacing the β-farnesene synthase coding sequence of expression plasmid pAM404 with the isoprene synthase coding sequence of plasmid Genetrix2080. DNA fragment IS2080 was generated by PCR amplifying plasmid Genetrix2080 using primers YD-198-70A (SEQ ID NO: 85) and YD-198-70B (SEQ ID NO: 86), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2080, yielding pAM1547 (see FIG. 6 for a plasmid map).

Expression plasmid pAM1548 was generated by replacing the β-farnesene synthase coding sequence of expression plasmid pAM404 with a truncated version of the isoprene synthase coding sequence of plasmid Genetrix2080. DNA fragment IS2080T was generated by PCR amplifying plasmid Genetrix2080 using primers YD-198-70B (SEQ ID NO: 86) and YD-198-70G (SEQ ID NO: 91), digesting the PCR product to completion using restriction endonucleases BamHI and NheI, resolving the reaction mixture by gel electrophoresis, and gel purifying the approximately 1.65 kb DNA fragment comprising the truncated isoprene synthase coding sequence. pAM404 was digested to completion using restriction endonucleases BamHI and NheI, the reaction mixture was resolved by gel electrophoresis, the approximately 7.3 kb backbone (lacking the β-farnesene synthase coding sequence) was gel purified, and the purified vector backbone was ligated with the amplified DNA fragment IS2080T, yielding pAM1548.

Expression plasmid pAM1549 was generated by replacing the β-farnesene synthase coding sequence of expression plasmid pAM404 with the isoprene synthase coding sequence of plasmid Genetrix2081. DNA fragment IS2081 was generated by PCR amplifying plasmid Genetrix2081 using primers YD-198-70C (SEQ ID NO: 87) and YD-198-70D (SEQ ID NO: 88), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2081, yielding pAM1549.

Expression plasmid pAM1550 was generated by replacing the β-farnesene synthase coding sequence of expression plasmid pAM404 with a truncated version of the isoprene synthase coding sequence of plasmid Genetrix2081. DNA fragment IS2081T was generated by PCR amplifying plasmid Genetrix2081 using primers YD-198-70D (SEQ ID NO: 88) and YD-198-70H (SEQ ID NO: 92), digesting the PCR product to completion using restriction endonucleases BamHI and NheI, resolving the reaction mixture by gel electrophoresis, and gel purifying the approximately 1.6 kb DNA fragment comprising the truncated isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the 0-farnesene synthase coding sequence) was gel purified, and the purified vector backbone was ligated with DNA fragment IS2081T, yielding pAM1550.

Expression plasmid pAM1551 was generated by replacing the β-farnesene synthase coding sequence of expression plasmid pAM404 with the isoprene synthase coding sequence of plasmid Genetrix2082. DNA fragment IS2082 was generated by PCR amplifying plasmid Genetrix2082 using primers YD-198-70E (SEQ ID NO: 89) and YD-198-70F (SEQ ID NO: 90), digesting the PCR product to completion using restriction endonucleases BamHI and NheI, resolving the reaction mixture by gel electrophoresis, and gel purifying the approximately 1.8 kb DNA fragment comprising the isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2082, yielding pAM1551.

Expression plasmid pAM1552 was generated by replacing the β-farnesene synthase coding sequence of expression plasmid pAM404 with a truncated version of the isoprene synthase coding sequence of plasmid Genetrix2082. DNA fragment IS2082T was generated by PCR amplifying plasmid Genetrix2082 using primers YD-198-70F (SEQ ID NO: 90) and YD-198-70I (SEQ ID NO: 93), digesting the PCR product to completion using restriction endonucleases BamHI and NheI, resolving the reaction mixture by gel electrophoresis, and gel purifying the approximately 1.64 kb DNA fragment comprising the truncated isoprene synthase coding sequence. Expression plasmid pAM404 was digested to completion using restriction endonucleases BamHI and NheI, the reaction mixture was resolved by gel electrophoresis, the approximately 7.3 kb vector backbone (lacking the β-farnesene synthase coding sequence) was gel purified, and the purified vector backbone was ligated with DNA fragment IS2082T, yielding pAM1552.

Plasmid pAM840 was generated by inserting the coding sequence of the hisG gene into the pCR®2.1-TOPO vector (Invitrogen, Carlsbad, Calif.). The coding sequence of the hisG gene was PCR amplified using primers KB34 (SEQ ID NO: 75) and KB39 (SEQ ID NO: 76) and plasmid pNKY51 (Alani et al. (1987) Genetics 116(4):541-555) as template. The amplified DNA fragment was ligated with the Topo vector as per manufacturer's suggested protocol, yielding pAM840.

Plasmid pAM728 was generated by introducing the coding sequence of the farnesene synthase gene of *Artemisia annua* (GenBank accession number AY835398) codon-optimized for expression in *Saccharomyces cerevisiae* and under control of the promoter of the GALT gene of *Sacharomyces cerevisiae* ($P_{GAL7}$) into plasmid pRS425 (Christianson et al. (1992) Gene 110(1):119-122). An approximately 0.5 kb DNA fragment comprising $P_{GAL7}$ was PCR amplified from Y002 genomic DNA using primers GW-110-26-pGAL7-PstI F (SEQ ID NO: 119) and GW-110-26-pGAL7 R (SEQ ID NO: 120) and was gel purified. An approximately 2 kb DNA fragment comprising the coding sequence of the farnesene synthase gene was PCR amplified using primers GW-110-26-pGAL7-FS F (SEQ ID NO: 121) and GW-110-26-FS-BamHI R (SEQ ID NO: 122). The two DNA fragments were stitched together using PCR primers GW-110-26-pGAL7-PstI F (SEQ ID NO: 119) and GW-110-26-FS-BamHI R (SEQ ID NO: 122) to create a $P_{GAL7}$-FS-tCYC1 insert. The $P_{GAL7}$-FS-tCYC1 insert and plasmid pRS425 were digested to completion using PstI and BamHI restriction endonucleases, and the two DNA fragments were ligated, yielding pAM728.

Plasmid pAM940 was generated by introducing the farnesene synthase sequence of plasmid pAM728 into plasmid pRS426 (Christianson et al. (1992) Gene 110(1):119-122). Plasmids pAM728 and pRS426 were digested to completion using XhoI and BamHI restriction endonucleases, the reaction mixtures were resolved by gel electrophoresis, the approximately 5.7 kb pRS426 vector backbone and the approximately 2.5 kb $P_{GAL7}$-FS-tCYC1 insert of pAM728 were gel purified, and the two DNA fragments were ligated, yielding plasmid pAM940.

Figure 7:
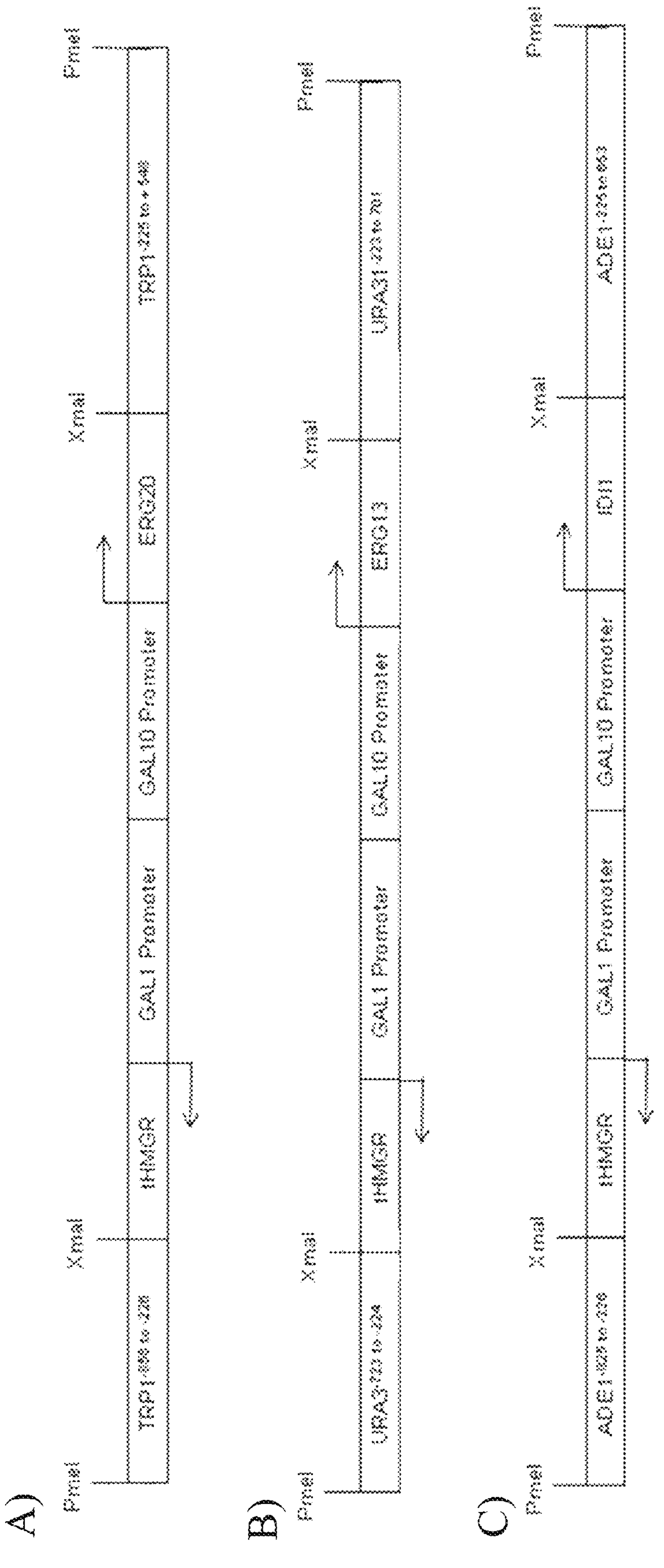
FIGS. 7A-G show maps of the inserts of vectors pAM489, pAM491, pAM493, pAM495, pAM497, and pAM584, and of the integration cassette natA-$P_{CTR3}^{-1\ to\ -734}$.
Figure 7:
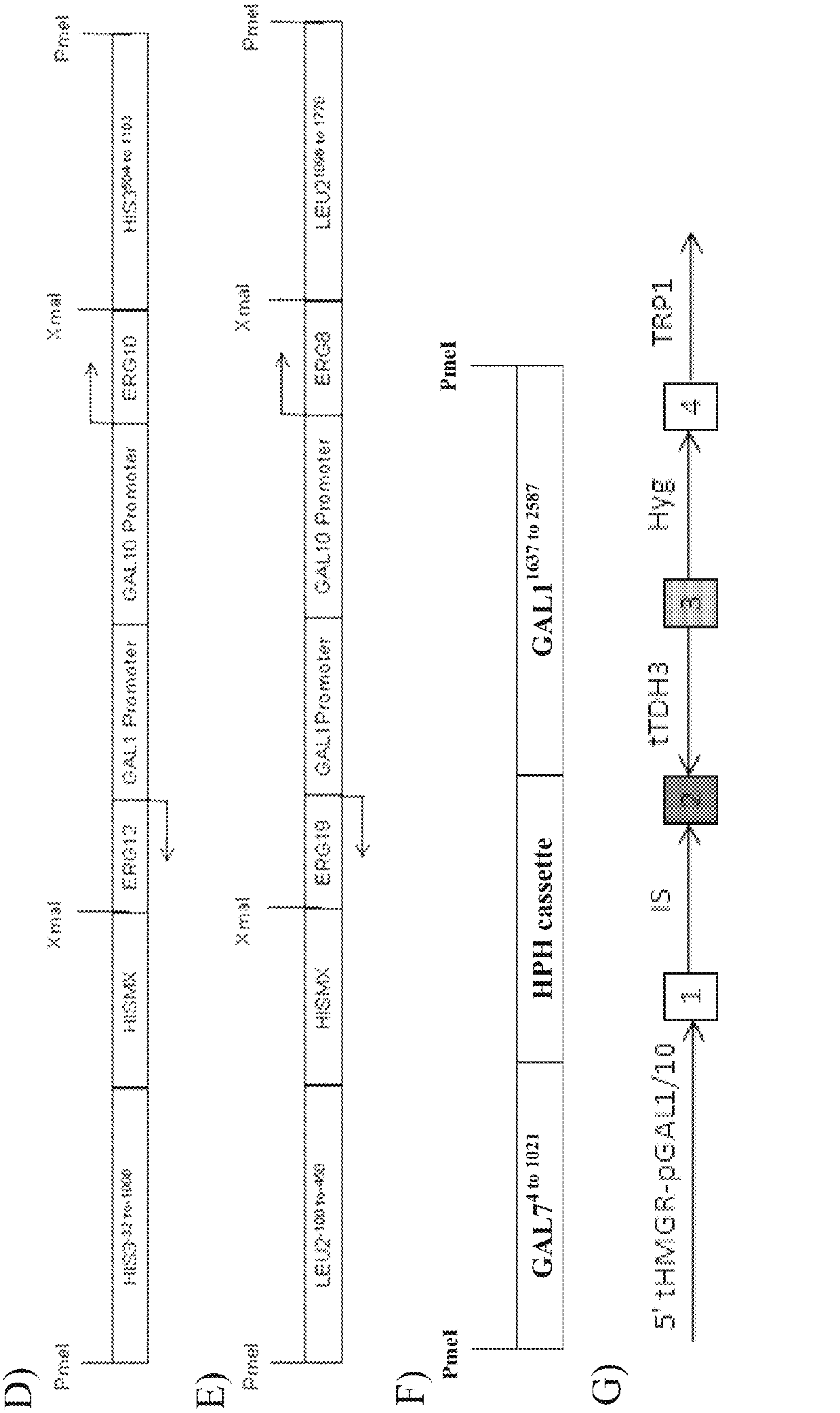

Plasmid pAM489 was generated by inserting the ERG20-$P_{GAL}$-tHMGR insert of vector pAM471 into vector pAM466. Vector pAM471 was generated by inserting DNA fragment ERG20-$P_{GAL}$-tHMGR, which comprises the open reading frame (ORF) of the ERG20 gene of *Saccharomyces cerevisiae* (ERG20 nucleotide positions 1 to 1208; A of ATG start codon is nucleotide 1) (ERG20), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide positions 1586 to 3323) (tHMGR), into the TOPO Zero Blunt II cloning vector (Invitrogen, Carlsbad, Calif.). Vector pAM466 was generated by inserting DNA fragment $TRP1^{-856\ to\ +548}$ which comprises a segment of the wild-type TRP1 locus of *Saccharomyces cerevisiae* that extends from nucleotide position −856 to position 548 and harbors a non-native internal XmaI restriction site between bases −226 and −225, into the TOPO TA pCR2.1 cloning vector (Invitrogen,q Carlsbad, Calif.). DNA fragments ERG20-$P_{GAL}$-tHMGR and $TRP1^{-856\ to\ +548}$ were generated by PCR amplification as outlined in Table 1. For the construction of pAM489, 400 ng of pAM471 and 100 ng of pAM466 were digested to completion using XmaI restriction enzyme (New England Biolabs, Ipswich, Mass.), DNA fragments corresponding to the ERG20-$P_{GAL}$-tHMGR insert and the linearized pAM466 vector were gel purified, and 4 molar equivalents of the purified insert was ligated with 1 molar equivalent of the purified linearized vector, yielding pAM489. FIG. 7A shows a map of the ERG20-$P_{GAL}$-tHMGR insert, and SEQ ID NO: 9 shows the nucleotide sequence of the DNA fragment and the flanking TRP1 sequences.

TABLE 1

PCR amplifications performed to generate pAM489

| PCR Round | Template | Primer 1 | Primer 2 | PCR Product |
|---|---|---|---|---|
| 1 | 100 ng of Y051 genomic DNA | 61-67-CPK001-G (SEQ ID NO: 23) | 61-67-CPK002-G (SEQ ID NO: 24) | $TRP1^{-856\ to\ -226}$ |
| | | 61-67-CPK003-G (SEQ ID NO: 25) | 61-67-CPK004-G (SEQ ID NO: 26) | $TRP1^{-225-to\ +548}$ |
| | 100 ng of EG123 genomic DNA | 61-67-CPK025-G (SEQ ID NO: 47) | 61-67-CPK050-G (SEQ ID NO: 55) | ERG20 |
| | 100 ng of Y002 genomic DNA | 61-67-CPK051-G (SEQ ID NO: 56) | 61-67-CPK052-G (SEQ ID NO: 57) | $P_{GAL}$ |
| | | 61-67-CPK053-G (SEQ ID NO: 58) | 61-67-CPK031-G (SEQ ID NO: 48) | tHMGR |
| 2 | 100 ng each of $TRP1^{-856\ to\ -226}$ and $TRP1^{-225-to\ +548}$ purified PCR products | 61-67-CPK001-G (SEQ ID NO: 23) | 61-67-CPK004-G (SEQ ID NO: 26) | $TRP1^{-856\ to\ +548}$ |
| | 100 ng each of ERG20 and $P_{GAL}$ purified PCR products | 61-67-CPK025-G (SEQ ID NO: 47) | 61-67-CPK052-G (SEQ ID NO: 57) | ERG20-$P_{GAL}$ |
| 3 | 100 ng each of ERG20-$P_{GAL}$ and tHMGR purified PCR products | 61-67-CPK025-G (SEQ ID NO: 47) | 61-67-CPK031-G (SEQ ID NO: 48) | ERG20-$P_{GAL}$-tHMGR |

Plasmid pAM491 was generated by inserting the ERG13-$P_{GAL}$-tHMGR insert of vector pAM472 into vector pAM467. Vector pAM472 was generated by inserting DNA fragment ERG13-$P_{GAL}$-tHMGR, which comprises the ORF of the ERG13 gene of *Saccharomyces cerevisiae* (ERG13 nucleotide positions 1 to 1626) (ERG13), the genomic locus containing the divergent GAL1 and GAL10 promoter of

*Saccharomyces cerevisiae* (GAL1 nucleotide position −1 to −668) ($P_{GAL}$), and a truncated ORF of the HMG1 gene of *Saccharomyces cerevisiae* (HMG1 nucleotide position 1586 to 3323) (tHMGR), into the TOPO Zero Blunt II cloning vector. Vector pAM467 was generated by inserting DNA fragment $URA3^{-723\ to\ 701}$, which comprises a segment of the wild-type URA3 locus of *Saccharomyces cerevisiae* that extends from nucleotide position −723 to position −224 and harbors a non-native internal XmaI restriction site between bases −224 and −223, into the TOPO TA pCR2.1 cloning vector. DNA fragments ERG13-$P_{GAL}$-tHMGR and $URA3^{-723\ to\ 701}$ were generated by PCR amplification as outlined in Table 2. For the construction of pAM491, 400 ng of pAM472 and 100 ng of pAM467 were digested to completion using XmaI restriction enzyme, DNA fragments corresponding to the ERG13-$P_{GAL}$-tHMGR insert and the linearized pAM467 vector were gel purified, and 4 molar equivalents of the purified insert was ligated with 1 molar equivalent of the purified linearized vector, yielding pAM491. FIG. 7B shows a map of the ERG13-$P_{GAL}$-tHMGR insert, and SEQ ID NO: 10 shows the nucleotide sequence of the DNA fragment and the flanking URA3 sequences.

TABLE 2

PCR amplifications performed to generate pAM491

| PCR Round | Template | Primer 1 | Primer 2 | PCR Product |
|---|---|---|---|---|
| 1 | 100 ng of Y007 genomic DNA | 61-67-CPK005-G (SEQ ID NO: 27) | 61-67-CPK006-G (SEQ ID NO: 28) | $URA3^{-723\ to\ -224}$ |
| | | 61-67-CPK007-G (SEQ ID NO: 29) | 61-67-CPK008-G (SEQ ID NO: 30) | $URA3^{-223\ to\ 701}$ |
| | 100 ng of Y002 genomic DNA | 61-67-CPK032-G (SEQ ID NO: 49) | 61-67-CPK054-G (SEQ ID NO: 59) | ERG13 |
| | | 61-67-CPK052-G (SEQ ID NO: 57) | 61-67-CPK055-G (SEQ ID NO: 60) | $P_{GAL}$ |
| | | 61-67-CPK031-G (SEQ ID NO: 48) | 61-67-CPK053-G (SEQ ID NO: 58) | tHMGR |
| 2 | 100 ng each of $URA3^{-723\ to\ -224}$ and $URA3^{-223\ to\ 701}$ purified PCR products | 61-67-CPK005-G (SEQ ID NO: 27) | 61-67-CPK008-G (SEQ ID NO: 30) | $uRA3^{-723\ to\ 701}$ |
| | 100 ng each of ERG13 and $P_{GAL}$ purified PCR products | 61-67-CPK032-G (SEQ ID NO: 49) | 61-67-CPK052-G (SEQ ID NO: 57) | ERG13-$P_{GAL}$ |
| 3 | 100 ng each of ERG13-$P_{GAL}$ and tHMGR purified PCR products | 61-67-CPK031-G (SEQ ID NO: 48) | 61-67-CPK032-G (SEQ ID NO: 49) | ERG13-$P_{GAL}$-tHMGR |

Plasmid pAM493 was generated by inserting the IDI1-$P_{GAL}$-tHMGR insert of vector pAM473 into vector pAM468. Vector pAM473 was generated by inserting DNA fragment IDI1-$P_{GAL}$-tHMGR, which comprises the ORF of the IDI1 gene of *Saccharomyces cerevisiae* (IDI1 nucleotide position 1 to 1017) (IDI1), the genomic locus containing the divergent GAL1 and GAL10 promoter of *Saccharomyces cerevisiae* (GAL1 nucleotide position −1 to −668) ($P_{GAL}$), and a truncated ORF of the HMG1 gene of *Saccharomyces cerevisiae* (HMG1 nucleotide positions 1586 to 3323) (tHMGR), into the TOPO Zero Blunt II cloning vector. Vector pAM468 was generated by inserting DNA fragment $ADE1^{-825\ to\ 653}$, which comprises a segment of the wild-type ADE1 locus of *Saccharomyces cerevisiae* that extends from nucleotide position −225 to position 653 and harbors a non-native internal XmaI restriction site between bases −226 and −225, into the TOPO TA pCR2.1 cloning vector. DNA fragments IDI1-$P_{GAL}$-tHMGR and $ADE1^{-825\ to\ 653}$ were generated by PCR amplification as outlined in Table 3. For the construction of pAM493, 400 ng of pAM473 and 100 ng of pAM468 were digested to completion using XmaI restriction enzyme, DNA fragments corresponding to the IDI1-$P_{GAL}$-tHMGR insert and the linearized pAM468 vector were gel purified, and 4 molar equivalents of the purified insert was ligated with 1 molar equivalent of the purified linearized vector, yielding vector pAM493. FIG. 7C shows a map of the IDI1-$P_{GAL}$-tHMGR insert, and SEQ ID NO: 11 shows the nucleotide sequence of the DNA fragment and the flanking ADE1 sequences.

TABLE 3

PCR amplifications performed to generate pAM493

| PCR Round | Template | Primer 1 | Primer 2 | PCR Product |
|---|---|---|---|---|
| 1 | 100 ng of Y007 genomic DNA | 61-67-CPK009-G (SEQ ID NO: 31) | 61-67-CPK010-G (SEQ ID NO: 32) | $ADE1^{-825\ to\ -226}$ |
| | | 61-67-CPK011-G (SEQ ID NO: 33) | 61-67-CPK012-G (SEQ ID NO: 34) | $ADE1^{-225\ to\ 653}$ |
| | 100 ng of Y002 genomic DNA | 61-67-CPK047-G (SEQ ID NO: 54) | 61-67-CPK064-G (SEQ ID NO: 69) | IDI1 |
| | | 61-67-CPK052-G (SEQ ID NO: 57) | 61-67-CPK065-G (SEQ ID NO: 70) | $P_{GAL}$ |
| | | 61-67-CPK031-G (SEQ ID NO: 48) | 61-67-CPK053-G (SEQ ID NO: 58) | tHMGR |

TABLE 3-continued

PCR amplifications performed to generate pAM493

| PCR Round | Template | Primer 1 | Primer 2 | PCR Product |
|---|---|---|---|---|
| 2 | 100 ng each of ADE1$^{-825\ to\ -226}$ and ADE1$^{-225\ to\ 653}$ purified PCR products | 61-67-CPK009-G (SEQ ID NO: 31) | 61-67-CPK012-G (SEQ ID NO: 34) | ADE1$^{-825\ to\ 653}$ |
| | 100 ng each of IDI1 and $P_{GAL}$ purified PCR products | 61-67-CPK047-G (SEQ ID NO: 54) | 61-67-CPK052-G (SEQ ID NO: 57) | IDI1-$P_{GAL}$ |
| 3 | 100 ng each of IDI1-$P_{GAL}$ and tHMGR purified PCR products | 61-67-CPK031-G (SEQ ID NO: 48) | 61-67-CPK047-G (SEQ ID NO: 54) | IDI1-$P_{GAL}$-tHMGR |

Plasmid pAM495 was generated by inserting the ERG10-$P_{GAL}$-ERG12 insert of pAM474 into vector pAM469. Vector pAM474 was generated by inserting DNA fragment ERG10-$P_{GAL}$-ERG12, which comprises the ORF of the ERG10 gene of *Saccharomyces cerevisiae* (ERG10 nucleotide position 1 to 1347) (ERG10), the genomic locus containing the divergent GAL1 and GAL10 promoter of *Saccharomyces cerevisiae* (GAL1 nucleotide position −1 to −668) ($P_{GAL}$), and the ORF of the ERG12 gene of *Saccharomyces cerevisiae* (ERG12 nucleotide position 1 to 1482) (ERG12), into the TOPO Zero Blunt II cloning vector. Vector pAM469 was generated by inserting DNA fragment HIS3$^{-32\ to\ -1000}$-HISMX-HIS3$^{504\ to\ -1103}$, which comprises two segments of the HIS locus of *Saccharomyces cerevisiae* that extend from nucleotide position −32 to position −1000 and from nucleotide position 504 to position 1103, a HISMX marker, and a non-native XmaI restriction site between the HIS3$^{504\ to\ -1103}$ sequence and the HISMX marker, into the TOPO TA pCR2.1 cloning vector. DNA fragments ERG10-$P_{GAL}$-ERG12 and HIS3$^{-32\ to\ -1000}$-HISMX-HIS3$^{504\ to\ -1103}$ were generated by PCR amplification as outlined in Table 4. For construction of pAM495, 400 ng of pAM474 and 100 ng of pAM469 were digested to completion using XmaI restriction enzyme, DNA fragments corresponding to the ERG10-$P_{GAL}$-ERG12 insert and the linearized pAM469 vector were gel purified, and 4 molar equivalents of the purified insert was ligated with 1 molar equivalent of the purified linearized vector, yielding vector pAM495. FIG. 7D shows a map of the ERG10-$P_{GAL}$-ERG12 insert, and SEQ ID NO: 12 shows the nucleotide sequence of the DNA fragment and the flanking HIS3 sequences.

TABLE 4

PCR reactions performed to generate pAM495

| PCR Round | Template | Primer 1 | Primer 2 | PCR Product |
|---|---|---|---|---|
| 1 | 100 ng of Y007 genomic DNA | 61-67-CPK013-G (SEQ ID NO: 35) | 61-67-CPK014alt-G (SEQ ID NO: 36) | HIS3$^{-32\ to\ -1000}$ |
| | | 61-67-CPK017-G (SEQ ID NO: 39) | 61-67-CPK018-G (SEQ ID NO: 40) | HIS3$^{504\ to\ -1103}$ |
| | | 61-67-CPK035-G (SEQ ID NO: 50) | 61-67-CPK056-G (SEQ ID NO: 61) | ERG10 |
| | | 61-67-CPK057-G (SEQ ID NO: 62) | 61-67-CPK058-G (SEQ ID NO: 63) | $P_{GAL}$ |
| | | 61-67-CPK040-G (SEQ ID NO: 51) | 61-67-CPK059-G (SEQ ID NO: 64) | ERG12 |
| | 10 ng of plasmid pAM330 DNA ** | 61-67-CPK015alt-G (SEQ ID NO: 37) | 61-67-CPK016-G (SEQ ID NO: 38) | HISMX |
| 2 | 100 ng each of HIS3$^{504\ to\ -1103}$ and HISMX PCR purified products | 61-67-CPK015alt-G (SEQ ID NO: 37) | 61-67-CPK018-G (SEQ ID NO: 40) | HISMX-HIS3$^{504\ to\ -1103}$ |
| | 100 ng each of ERG10 and $P_{GAL}$ purified PCR products | 61-67-CPK035-G (SEQ ID NO: 50) | 61-67-CPK058-G (SEQ ID NO: 63) | ERG10-$P_{GAL}$ |
| | 100 ng each of HIS3$^{-32\ to\ -1000}$ and HISMX-HIS3$^{504\ to\ -1103}$ purified PCR products | 61-67-CPK013-G (SEQ ID NO: 35) | 61-67-CPK018-G (SEQ ID NO: 40) | HIS3$^{-32\ to\ -1000}$-HISMX-HIS3$^{504\ to\ -1103}$ |
| 3 | 100 ng each of ERG10-$P_{GAL}$ and ERG12 purified PCR products | 61-67-CPK035-G (SEQ ID NO: 50) | 61-67-CPK040-G (SEQ ID NO: 51) | ERG10-$P_{GAL}$-ERG12 |

** The HISMX marker in pAM330 originated from pFA6a-HISMX6-PGAL1 as described by van Dijken et al. ((2000) *Enzyme Microb. Technol.* 26(9-10): 706-714).

Plasmid pAM497 was generated by inserting the ERG8-$P_{GAL}$-ERG19 insert of pAM475 into vector pAM470. Vector pAM475 was generated by inserting DNA fragment ERG8-$P_{GAL}$-ERG19, which comprises the ORF of the ERG8 gene of *Saccharomyces cerevisiae* (ERG8 nucleotide position 1 to 1512) (ERG8), the genomic locus containing the divergent GAL1 and GAL10 promoter of *Saccharomyces cerevisiae* (GAL1 nucleotide position −1 to −668) ($P_{GAL}$), and the ORF of the ERG19 gene of *Saccharomyces cerevisiae* (ERG19 nucleotide position 1 to 1341) (ERG19), into the TOPO Zero Blunt II cloning vector. Vector pAM470 was generated by inserting DNA fragment LEU2$^{-100\ to\ 450}$-HISMX-LEU2$^{1096\ to\ 1770}$, which comprises two segments of the LEU2 locus of *Saccharomyces cerevisiae* that extend from nucleotide position −100 to position 450 and from nucleotide position 1096 to position 1770, a HISMX marker, and a non-native XmaI restriction site between the $LEU2^{1096\ to\ 1770}$ sequence and the HISMX marker, into the TOPO TA pCR2.1 cloning vector. DNA fragments ERG8-$P_{GAL}$-ERG19 and $LEU2^{-100\ to\ 450}$-HISMX-$LEU2^{1096\ to\ 1770}$ were generated by PCR amplification as outlined in Table 5. For the construction of pAM497, 400 ng of pAM475 and 100 ng of pAM470 were digested to completion using XmaI restriction enzyme, DNA fragments corresponding to the ERG8-$P_{GAL}$-ERG19 insert and the linearized pAM470 vector were purified, and 4 molar equivalents of the purified insert was ligated with 1 molar equivalent of the purified linearized vector, yielding vector pAM497. FIG. 7E for a map of the ERG8-$P_{GAL}$-ERG19 insert, and SEQ ID NO: 13 shows the nucleotide sequence of the DNA fragment and the flanking LEU2 sequences.

TABLE 5

PCR reactions performed to generate pAM497

| PCR Round | Template | Primer 1 | Primer 2 | PCR Product |
|---|---|---|---|---|
| 1 | 100 ng of Y007 genomic DNA | 61-67-CPK019-G (SEQ ID NO: 41) | 61-67-CPK020-G (SEQ ID NO: 42) | $LEU2^{-100\ to\ 450}$ |
| | | 61-67-CPK023-G (SEQ ID NO: 45) | 61-67-CPK024-G (SEQ ID NO: 46) | $LEU2^{1096\ to\ 1770}$ |
| | 10 ng of plasmid pAM330 DNA ** | 61-67-CPK021-G (SEQ ID NO: 43) | 61-67-CPK022-G (SEQ ID NO: 44) | HISMX |
| | 100 ng of Y002 genomic DNA | 61-67-CPK041-G (SEQ ID NO: 52) | 61-67-CPK060-G (SEQ ID NO: 65) | ERG8 |
| | | 61-67-CPK061-G (SEQ ID NO: 66) | 61-67-CPK062-G (SEQ ID NO: 67) | $P_{GAL}$ |
| | | 61-67-CPK046-G (SEQ ID NO: 53) | 61-67-CPK063-G (SEQ ID NO: 68) | ERG19 |
| 2 | 100 ng each of $LEU2^{1096\ to\ 1770}$ and HISMX purified PCR products | 61-67-CPK021-G (SEQ ID NO: 43) | 61-67-CPK024-G (SEQ ID NO: 46) | HISMX-$LEU2^{1096\ to\ 1770}$ |
| | 100 ng each of ERG8 and $P_{GAL}$ purified PCR products | 61-67-CPK041-G (SEQ ID NO: 52) | 61-67-CPK062-G (SEQ ID NO: 67) | ERG8-$P_{GAL}$ |
| 3 | 100 ng of $LEU2^{-100\ to\ 450}$ and HISMX- $LEU2^{1096\ to\ 1770}$ purified PCR products | 61-67-CPK019-G (SEQ ID NO: 41) | 61-67-CPK024-G (SEQ ID NO: 46) | $LEU2^{-100\ to\ 450}$-HISMX-$LEU2^{1096\ to\ 1770}$ |
| | 100 ng each of ERG8-$P_{GAL}$ and ERG19 purified PCR products | 61-67-CPK041-G (SEQ ID NO: 52) | 61-67-CPK046-G (SEQ ID NO: 53) | ERG8-$P_{GAL}$-ERG19 |

** The HISMX marker in pAM330 originated from pFA6a-HISMX6-PGAL1 as described by van Dijken et al. ((2000) *Enzyme Microb. Technol.* 26(9-10): 706-714).

Plasmid pAM584 was generated by inserting DNA fragment $GAL7^{4\ to\ 1021}$-HPH-$GAL1^{1637\ to\ 2587}$ into the TOPO ZERO Blunt II cloning vector (Invitrogen, Carlsbad, Calif.). DNA fragment $GAL7^{4\ to\ 1021}$-HPH-$GAL1^{1637\ to\ 2587}$ comprises a segment of the ORF of the GAL7 gene of *Saccharomyces cerevisiae* (GAL7 nucleotide positions 4 to 1021) ($GAL7^{4\ to\ 1021}$), the hygromycin resistance cassette (HPH), and a segment of the 3' untranslated region (UTR) of the GAL1 gene of *Saccharomyces cerevisiae* (GAL1 nucleotide positions 1637 to 2587). The DNA fragment was generated by PCR amplification as outlined in Table 6. FIG. 7F shows a map and SEQ ID NO: 102 the nucleotide sequence of DNA fragment $GAL7^{4\ to\ 1021}$-HPH-$GAL1^{1637\ to\ 2587}$.

TABLE 6

PCR reactions performed to generate pAM584

| PCR Round | Template | Primer 1 | Primer 2 | PCR Product |
|---|---|---|---|---|
| 1 | 100 ng of Y002 genomic DNA | 91-014-CPK236-G (SEQ ID NO: 126) | 91-014-CPK237-G (SEQ ID NO: 127) | $GAL7^{4\ to\ 1021}$ |
| | | 91-014-CPK232-G (SEQ ID NO: 124) | 91-014-CPK233-G (SEQ ID NO: 125) | $GAL1^{1637\ to\ 2587}$ |
| | 10 ng of plasmid pAM547 DNA ** | 91-014-CPK231-G (SEQ ID NO: 123) | 91-014-CPK238-G (SEQ ID NO: 128) | HPH |
| 2 | 100 ng each of $GAL7^{4\ to\ 1021}$ and HPH purified PCR products | 91-014-CPK231-G (SEQ ID NO: 123) | 91-014-CPK236-G (SEQ ID NO: 126) | $GAL7^{4\ to\ 1021}$-HPH |

TABLE 6-continued

| PCR reactions performed to generate pAM584 | | | | |
|---|---|---|---|---|
| PCR Round | Template | Primer 1 | Primer 2 | PCR Product |
| 3 | 100 ng of each GAL1$^{1637\ to\ 2587}$ and GAL7$^{4\ to\ 1021}$-HPH purified PCR products | 91-014-CPK233-G (SEQ ID NO: 125) | 91-014-CPK236-G (SEQ ID NO: 126) | GAL7$^{4\ to\ 1021}$-HPH-GAL1$^{1637\ to\ 2587}$ |

** Plasmid pAM547 was generated synthetically, and comprises the HPH cassette, which consists of the coding sequence for the hygromycin B phosphotransferase of *Escherichia coli* flanked by the promoter and terminator of the Tef1 gene of *Kluyveromyces lactis*.

Integration cassette natA-$P_{CTR3}^{-1\ to\ 734}$ was generated by PCR amplifying the natA marker using primers PW287-002-CPK1217 (SEQ ID NO: 104) and DE_PW91-027-CPK262-G (SEQ ID NO: 99) and using plasmid DNA comprising the TEF1 promoter and terminator of *Kluyveromyces lactis* (GenBank accession CR382122 REGIONS: 788874 . . . 789380 and 787141 . . . 787496, respectively) and the nat resistance marker. In addition, the promoter of the CTR3 gene of *Saccharomyces cerevisiae* was PCR amplified from Y002 genomic DNA from positions −1 to −734 using primers PW287-002-CPK1232 (SEQ ID NO: 100) and DE_PW91-027-CPK263-G (SEQ ID NO: 101). The 2 PCR products were stitched together in a secondary PCR reaction using 25 ng of each of the gel purified PCR fragments and primers PW287-002-CPK1217 and PW287-002-CPK1232, yielding integration cassette natA-$P_{CTR3}^{-1\ to\ -734}$.

Additional recombinant integration cassettes were generated by stitching RABits. RABits were generated by inserting DNA fragments of interest (MULEs) into the pMULE Entry vector.

Figure 8:
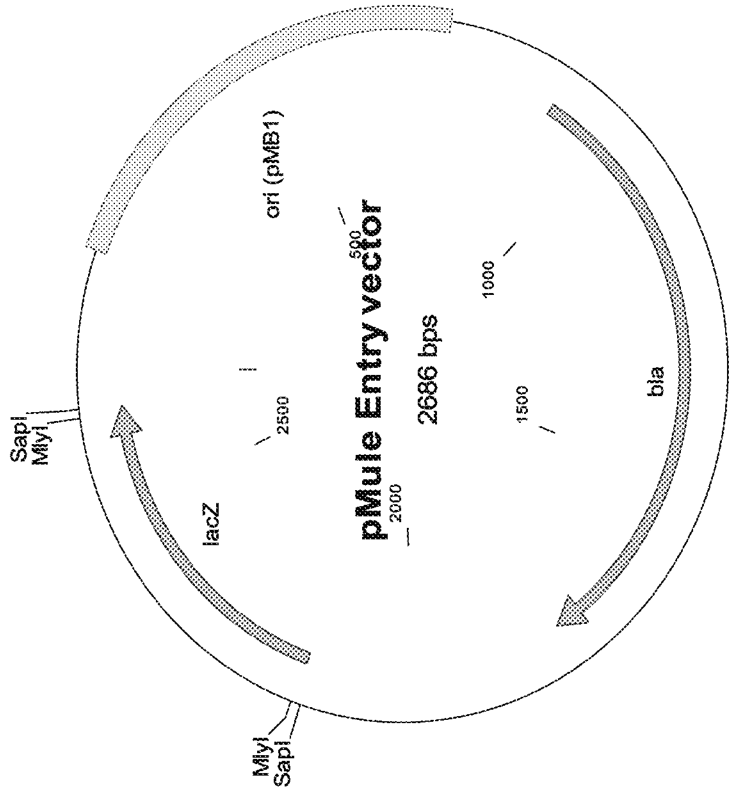
FIG. 8 shows a map of the pMULE Entry vector.

The pMULE Entry vector was PCR amplified using primers K162 (SEQ ID NO: 73) and K163 (SEQ ID NO: 74) and pRYSE Entry vector 8 (SEQ ID NO: 14) as template. The reaction mixture was resolved by gel electrophoresis, and the approximately 2.2 kb vector backbone was gel purified. A DNA fragment comprising the lacZ coding sequence was generated by digesting to completion pRYSE Entry vector 8 using SchI restriction enzyme, heat inactivating the enzyme (20 min at 65° C.), resolving the reaction mixture by gel electrophoresis, and gel purifying the approximately 0.5 kb DNA fragment. The purified DNA fragment comprising the lacZ coding sequence was ligated with the purified vector backbone, yielding the pMULE Entry vector (see FIG. 8 for a plasmid map).

MULEs were PCR amplified using templates and primers as outlined in Table 7. PCR amplifications were done using the Phusion DNA polymerase (New England Biolabs, Ipswich, Mass.) as per manufacturer's suggested protocol.

TABLE 7

| Amplified MULEs | | | |
|---|---|---|---|
| MULE | Primers | Template | Size (bp) |
| 5' ERG20-pGAL1/10 | YD-198-75A (SEQ ID NO: 94) YD-198-75B (SEQ ID NO: 95) | pAM489 | 1,012 |
| mIS2081 | YD-198-75F (SEQ ID NO: 96) YD-198-75H (SEQ ID NO: 98) | Genetrix2081 | 1,836 |
| mIS2081T | YD-198-75G (SEQ ID NO: 97) YD-198-75H (SEQ ID NO: 98) | Genetrix2081 | 1,668 |
| tTDH3 | RYSE 4 (SEQ ID NO: 77) RYSE 7 (SEQ ID NO: 78) | RABit63 * | 311 |

TABLE 7-continued

| Amplified MULEs | | | |
|---|---|---|---|
| MULE | Primers | Template | Size (bp) |
| Hyg | YD-198-75L (SEQ ID NO: 105) YD-198-75M (SEQ ID NO: 106) | RABit21 * | 1,962 |
| TRP1 | YD-198-75N (SEQ ID NO: 107) YD-198-75O (SEQ ID NO: 108) | pAM489 | 586 |

* RABit21 comprises SEQ ID NO: 15, and RABit63 comprises SEQ ID NO: 16.

RABits were generated by inserting the MULEs into the pMULE Entry vector. The PCR reactions were resolved by gel electrophoresis, the MULEs were gel purified, the purified MULEs were treated with T4 polynucleotide kinase (PNK) (New England Biolabs, Ipswich, Mass.) as per manufacturer's suggested protocol, and the PNK was heat inactivated at 65° C. for 20 minutes. The pMULE Entry vector was digested to completion using SchI restriction enzyme, the approximately 2.2 kb pMULE Entry vector backbones (lacking lacZ) was gel purified, the purified pMULE Entry vector backbone was treated with Antarctic Phosphatase (New England Biolabs, Ipswich, Mass.), and the phosphatase was heat inactivated at 65° C. for 20 minutes. The pMULE Entry vector backbone was ligated with each of the amplified MULEs, yielding RABits.

RABits to be stitched (Table 8) were placed together in one tube (333 fmole of each RABit) and digested to completion using LguI restriction enzyme (Fermentas, Glen Burnie, Md.). The restriction enzyme was heat inactivated for 20 minutes at 65° C. The RABit digestion reactions were split into three 30 uL reactions; water, buffer, dNTPs, and DNA polymerase were added to each reaction mixture, and a first round of PCR amplification was initiated. Samples were placed on ice, 0.5 uM of each terminal primer (Table 8) were added to the reaction mixtures, and a second round of PCR amplification was performed. The three PCR reaction mixtures were combined in one tube, the reaction mixtures were resolved by gel electrophoresis, and the PCR products were gel purified. FIG. 7G shows a map of the integration cassettes.

TABLE 8

| PCR Amplification of Integration Cassettes | | |
|---|---|---|
| Integration Cassette | RABits to be combined | Terminal Primers for 2$^{nd}$ Round PCR amplification |
| i00280 | 5' ERG20-pGAL1/10-mIS2081-tTDH3-Hyg-TRP1 | YD-198-75A (SEQ ID NO: 94) |

TABLE 8-continued

| PCR Amplification of Integration Cassettes | | |
|---|---|---|
| Integration Cassette | RABits to be combined | Terminal Primers for $2^{nd}$ Round PCR amplification |
| i00281 | 5' ERG20-pGAL1/10-mIS2081T-tTDH3-Hyg-TRP1 | YD-198-75O (SEQ ID NO: 108) |

The first round of PCR amplification was performed as follows: one cycle of denature at 98° C. for 2 minutes; 5 cycles of denature at 98° C. for 30 seconds and anneal/extend at 72° C. for 30 seconds per kilobase PCR product. The second round of PCR amplification was performed as follows: one cycle of denature at 98° C. for 2 minutes; 35 rounds of denature at 98° C. for 12 seconds and anneal/extend at 72° C. for 20 seconds per kilobase PCR product; one cycle of final extend at 72° C. for 7 minutes; and a final hold at 4° C.

Example 3

This example describes methods for generating *Saccharomyces cerevisiae* strains expressing heterologous isoprene synthases.

*Saccharomyces cerevisiae* strains CEN.PK2-1C (Y002) (MATA; ura3-52; trp1-289; leu2-3,112; his3Δ1; MAL2-8C; SUC2) and CEN.PK2-1D (Y003) (MATalpha; ura3-52; trp1-289; leu2-3,112; his3Δ1; MAL2-8C; SUC2) (van Dijken et al. (2000) Enzyme Microb. Technol. 26(9-10): 706-714) were prepared for introduction of inducible MEV pathway genes by replacing the ERG9 promoter with the *Saccharomyces cerevisiae* MET3 promoter, and the ADE1 ORF with the *Candida glabrata* LEU2 gene (CgLEU2). This was done by PCR amplifying the KanMX-$P_{MET3}$ region of vector pAM328 (SEQ ID NO: 17) using primers 50-56-pw100-G (SEQ ID NO: 19) and 50-56-pw101-G (SEQ ID NO: 20), which include 45 base pairs of homology to the native ERG9 promoter, transforming 10 μg of the resulting PCR product into exponentially growing Y002 and Y003 cells using 40% w/w Polyethelene Glycol 3350 (Sigma-Aldrich, St. Louis, Mo.), 100 mM Lithium Acetate (Sigma-Aldrich, St. Louis, Mo.), and 10 μg Salmon Sperm DNA (Invitrogen Corp., Carlsbad, Calif.), and incubating the cells at 30° C. for 30 minutes followed by heat shocking them at 42° C. for 30 minutes (Schiestl and Gietz. (1989) Curr. Genet. 16, 339-346). Positive recombinants were identified by their ability to grow on rich medium containing 0.5 μg/ml Geneticin (Invitrogen Corp., Carlsbad, Calif.), and selected colonies were confirmed by diagnostic PCR. The resultant clones were given the designation Y93 (MAT A) and Y94 (MAT alpha). The 3.5 kb CgLEU2 genomic locus was then amplified from *Candida glabrata* genomic DNA (ATCC, Manassas, Va.) using primers 61-67-CPK066-G (SEQ ID NO: 71) and 61-67-CPK067-G (SEQ ID NO: 72), which contain 50 base pairs of flanking homology to the ADE1 ORF, and 10 μg of the resulting PCR product were transformed into exponentially growing Y93 and Y94 cells, positive recombinants were selected for growth in the absence of leucine supplementation, and selected clones were confirmed by diagnostic PCR. The resultant clones were given the designation Y176 (MAT A) and Y177 (MAT alpha).

Strain Y188 was generated by digesting 2 μg of pAM491 and pAM495 plasmid DNA to completion using PmeI restriction endonucleose (New England Biolabs, Beverly, Mass.), and introducing the purified DNA inserts into exponentially growing Y176 cells. Positive recombinants were selected for by growth on medium lacking uracil and histidine, and integration into the correct genomic locus was confirmed by diagnostic PCR.

Strain Y189 was generated by digesting 2 μg of pAM489 and pAM497 plasmid DNA to completion using PmeI restriction endonuclease, and introducing the purified DNA inserts into exponentially growing Y177 cells. Positive recombinants were selected for by growth on medium lacking tryptophan and histidine, and integration into the correct genomic locus was confirmed by diagnostic PCR.

Strain Y238 was generated by mixing approximately $1\times10^7$ cells from strains Y188 and Y189 on a YPD medium plate for 6 hours at room temperature to allow for mating, plating the mixed cell culture to medium lacking histidine, uracil, and tryptophan to select for growth of diploid cells, digesting 2 μg of pAM493 plasmid DNA to completion using PmeI restriction endonuclease, and introducing the purified DNA insert into the exponentially growing diploid cells. Positive recombinants were selected for by growth on medium lacking adenine, and integration into the correct genomic locus was confirmed by diagnostic PCR.

Strains Y210 (Mat A) and Y211 (MAT alpha) were generated by sporulating strain Y238 in 2% Potassium Acetate and 0.02% Raffinose liquid medium, isolating approximately 200 genetic tetrads using a Singer Instruments MSM300 series micromanipulator (Singer Instrument LTD, Somerset, UK), identifying independent genetic isolates containing the appropriate complement of introduced genetic material by their ability to grow in the absence of adenine, histidine, uracil, and tryptophan, and confirming the integration of all introduced DNA by diagnostic PCR.

Strain Y258 was generated by transforming strain Y211 with pAM404 plasmid DNA. Host cell transformants were selected on synthetic defined media, containing 2% glucose and all amino acids except leucine (SM-glu). Single colonies were transferred to culture vials containing 5 mL of liquid SM-glu lacking leucine, and the cultures were incubated by shaking at 30° C. until growth reached stationary phase. The cells were stored at −80° C. in cryo-vials in 1 mL frozen aliquots made up of 400 uL 50% sterile glycerol and 600 uL liquid culture.

Strains Y225 (MAT A) and Y227 (MAT alpha) were generated by transforming exponentially growing Y210 and Y211 cells, respectively, with 2 μg of pAM426 (SEQ ID NO: 18), which comprises a GAL1 promoter operably linked to the coding sequence of an amorpha-4,11-diene synthase gene that is codon-optimized for expression in *Saccharomyces cerevisiae* (Merke et al. (2000) Ach. Biochem. Biophys. 381:173-180). Host cell transformants were selected on complete synthetic defined media lacking leucine.

Strain Y337 was generated from strain Y227 by rendering the strain unable to catabolize galactose. To this end, pAM584 plasmid DNA was digested to completion using PmeI restriction endonuclease, and the purified DNA insert $GAL7^{4\ to\ 1021}$-HPH-$GAL1^{1637\ to\ 2587}$ was introduced into exponentially growing Y227 cells. Positive recombinants were selected for by growth on solid medium lacking adenine, leucine, lysine, histidine, methionine, uracil, and tryptophan, and containing 900 μg/mL hygromycin B (Sigma, St. Louis, Mo.). Integration into the correct genomic locus was confirmed by diagnostic PCR and by testing the strain for inability to use galactose as a carbon source.

Strain Y615 was generated from strain Y337 by replacing the URA3 open reading frame with the hisG open reading frame from *Salmonella* sp . . . A DNA fragment comprising the hisG open reading frame was PCR amplified from pAM840 using primers 100-150-KB034-G (SEQ ID NO: 109) and 100-150-KB039-G (SEQ ID NO: 110), and the purified DNA fragment was introduced into exponentially growing Y337 cells. Positive transformants were selected for their ability to grow on medium containing 5-fluoroorotic acid and for their inability to grow on medium lacking uracil. Integration into the correct genomic locus was confirmed by diagnostic PCR.

Strain Y1775 was generated from strain Y615 by replacing the kanMX marker with the URA3 marker. A DNA fragment encoding the *S. cerevisiae* URA3 auxotrophic marker was PCR amplified from pAM64 (SEQ ID NO: 103) using primers PW-191-046-CPK1212-G (SEQ ID NO: 111) and PW-191-046-CPK1213-G (SEQ ID NO: 112), and the purified DNA fragment was introduced into exponentially growing Y615 cells. Positive recombinants were selected for by growth on medium lacking adenine, leucine, lysine, histidine, methionine, uracil, and tryptophan. Integration into the correct genomic locus was confirmed by diagnostic PCR.

Strain Y1791 was generated from strain Y1775 by restoring the ERG9 locus. A DNA fragment comprising the ERG9 open reading frame was PCR amplified from Y002 genomic DNA using primers PW-191-015-CPK947-G (SEQ ID NO: 113) and PW-191-015-CPK950-G (SEQ ID NO: 114), and the purified DNA fragment was introduced into exponentially growing Y1775 cells. Positive transformants we selected for their ability to grow on medium containing 5-fluoroorotic acid and for their inability to grow on medium lacking uracil. Integration into the correct genomic locus was confirmed by diagnostic PCR.

Strain Y1856 was generated from strain Y1791 by restoring the GAL1, GAL10, and GAL7 locus. A DNA fragment comprising the GAL1, GAL10, and GAL7 genomic region was PCR amplified from Y002 genomic DNA using primers PW-91-093-CPK453-G (SEQ ID NO: 115) and PW-091-144-CPK689-G (SEQ ID NO: 116), and the purified DNA fragment was introduced into exponentially growing Y1791 cells. Positive recombinants were selected for by growth on medium containing 20 g/L glacatose and their inability to grow on medium containing 900 μg/mL hygromycin B.

Strain Y1857 was generated from strain Y1856 by disrupting the $P_{GAL10}$-ERG20 locus. A DNA fragment encoding the *S. cerevisiae* URA3 auxotrophic marker was PCR amplified from pAM64 (SEQ ID NO: 130) using primers PW-287-002-CPK1215-G (SEQ ID NO: 117) and PW-287-002-CPK1216-G (SEQ ID NO: 118), and the purified DNA fragment was introduced into exponentially growing Y1856 cells. Positive recombinants were selected for by growth on medium lacking adenine, leucine, lysine, histidine, methionine, uracil, and tryptophan. Integration into the correct genomic locus was confirmed by diagnostic PCR.

Strain Y1895 was generated from strain Y1857 by curing the strain from pAM426. Strain Y1857 was propagated in rich Yeast Extract Peptone Dextrose (YPD) medium contain 0.5% leucine (w/v) for 5 days. Every 12 hours, fresh YPD 0.5% LEU was inoculated to an $OD_{600}$ of 0.05 using the previous 12 hour growth. After 5 days, the cells were plated on YPD 0.5% leucine agar medium and incubated at 30° C. for 2 days. Cured cells were identified by their ability to grow on minimal medium containing leucine and their inability to grow on medium lacking leucine.

Strain Y736 was generated from strain Y227 by replacing the URA3 marker with a hisG marker. To this end, the hisG marker was PCR amplified using primers KB34 (SEQ ID NO: 75) and KB39 (SEQ ID NO: 76) and plasmid pAM840 as template. Exponentially growing Y211 cells were transformed with the PCR mixture and were then plated on YPD overnight. Host cell transformants were selected by replica plating cells from the YPD plates onto Complete Synthetic Medium (CSM) solid media lacking methionine and leucine and containing 0.1% 5-FOA and 0.1 mg/ml uracil.

Strain Y737 was generated from strain Y736 by transforming exponentially growing cells with pAM940, and selecting host cell transformants on CSM solid media lacking leucine and uracil.

Strain Y846 was generated from strain Y737 by curing the strain of pAM426. To this end, strain Y737 was grown for 3 successive nights in rich media supplemented with 6× the usual concentration of leucine, being diluted each morning 100×. The cells were then plated out to well-separated single colonies on rich media and replica plated onto minimal media lacking leucine. Colonies that grew on rich media but did not grow in the absence of leucine were picked, grown, and tested by PCR to verify that the plasmid was no longer present. One such positive colony was stocked as Y846.

Strain Y1858 was generated from strain Y1895 by heterologous expression of an isoprene synthase. To this end, exponentially growing Y1895 cells were transformed with expression plasmid pAM1547. Host cell transformants were selected on CSM agar lacking methionine and leucine and containing 2% glucose.

Strain Y1859 was generated from strain Y1895 by heterologous expression of an isoprene synthase. To this end, exponentially growing Y1895 cells were transformed with expression plasmid pAM1548. Host cell transformants were selected on CSM agar lacking methionine and leucine and containing 2% glucose.

Strain Y1860 was generated from strain Y1895 by heterologous expression of an isoprene synthase. To this end, exponentially growing Y1895 cells were transformed with expression plasmid pAM1549. Host cell transformants were selected on CSM agar lacking methionine and leucine and containing 2% glucose.

Strain Y1861 was generated from strain Y1895 by heterologous expression of an isoprene synthase. To this end, exponentially growing Y1895 cells were transformed with expression plasmid pAM1550. Host cell transformants were selected on CSM agar lacking methionine and leucine and containing 2% glucose.

Strain Y1713 was generated from strain Y846 by replacing the ERG20 gene with the coding sequence for an isoprene synthase. To this end, exponentially growing Y846 cells were transformed with integration cassette i00280. Host cell transformants were selected on YPD agar containing 2% glucose and 300 μg/mL hygromycin B (A.G. Scientific, San Diego, Calif.).

Strain Y1714 was generated from strain Y846 by replacing the ERG20 gene with a coding sequence for a truncated isoprene synthase. To this end, exponentially growing Y846 cells were transformed with integration cassette i00281. Host cell transformants were selected on YPD agar containing 2% glucose and 300 μg/mL hygromycin B (A.G. Scientific, San Diego, Calif.).

Strain Y1732 was generated from strain Y846 by heterologous expression of an isoprene synthase. To this end, exponentially growing Y846 cells were transformed with expression plasmid pAM1549. Host cell transformants were selected on CSM agar lacking methionine and leucine and containing 2% glucose.

Strain Y1733 was generated from strain Y846 by heterologous expression of a truncated isoprene synthase. To this end, exponentially growing Y846 cells were transformed with expression plasmid pAM1550. Host cell transformants were selected on CSM agar lacking methionine and leucine and containing 2% glucose.

Strain Y1837 was generated by transforming exponentially growing Y1713 cells with expression plasmid pAM1549. Host cell transformants were selected on CSM agar lacking methionine and leucine and containing 2% glucose.

Strain Y1838 was generated by transforming exponentially growing Y1714 cells with expression plasmid pAM1550. Host cell transformants were selected on CSM agar lacking methionine and leucine and containing 2% glucose.

Strain 1907 was generated from strain Y1860 by replacing the ERG20 promoter with the nourseothricin resistance marker (natA) and the copper repressible promoter of the CTR3 gene of *Saccharomyces cerevisiae*. To this end, exponentially growing Y1860 cells were transformed with 200 μg of the integration cassette natA-$P_{CTR3}^{-1\ to\ -734}$. Host cell transformants were selected for by growth on rich YPD medium containing 300 μg/mL nourseothricin (Werner BioAgents, Jena, Germany).

Example 4

This example describes methods for producing isoprene in *Saccharomyces cerevisiae* host strains.

Single colonies of host cell transformants were transferred to culture vials containing 5 mL of Bird Seed Medium containing 0.25 uM $CuSO_4$. The following day, 20 mL of Bird Production Medium containing 1.8% galactose, 0.2% glucose, and 32 uM $CuSO_4$, with 4 mL isopropylmyristate, was inoculated with host cell transformant Y1858, Y1859, Y1860, or Y1861 to an $OD_{600}$ of 0.05. Similarly, 20 mL of Bird Production Medium containing 1.8% galactose and 0.2% glucose, with 4 mL isopropylmyristate, was inoculated with isolates #3, 6, or 9 of host cell transformant Y1907 to an $OD_{600}$ of 0.05. To the Y1907 culture, 0.25 uM $CuSO_4$, 50 uM $CuSO_4$, or 150 uM $CuSO_4$ was added. The shake flasks were sealed for anaerobic growth and incubated at 30° C. on a rotary shaker at 200 rpm.

After 72 hours of growth, the cultures were assayed for cell growth. At the same time, 200 uL of isopropylmyristate was removed from each flask and were injected directly on an Agilent 7980 gas chromatograph equipped with a flame ionization detector. To expedite run times, the temperature program and column matrix were modified to achieve optimal resolution and the shortest overall runtime (15.0 min). Each 2 μL sample was split 10:1 and was separated using a Varian fused silica CP-PoraBond U PLOT (25 m×0.32 mm×7 um; length×width×film thickness) column with hydrogen as the carrier gas. The temperature program for the analysis was as follows: the column was initially held at 100° C. for 1 minute, followed by a temperature gradient of 10° C./min to a temperature of 140° C., followed by a temperature gradient of 40° C./min to a temperature of 250° C., followed by holding the column at 250° C. for 6.5 min. Under these conditions, isoprene elutes at 5.8 minutes.

What is claimed:

1. A liquid isoprene composition comprising isoprene in an amount of at least about 99% by weight, wherein the liquid isoprene composition comprises 1 part per million or less of $C_2$-$C_5$ alkynes, cyclopentadiene, piperylene, and 1,4-pentadiene, wherein the liquid isoprene composition further comprises carbon dioxide in an amount greater than 0.01% by weight, nitrogen in an amount between about 0.001% and about 1% by weight, and ethanol in an amount greater than about 0.01% by weight.

2. The liquid isoprene composition of claim 1 comprising at least about 99.5% isoprene by weight.

3. The liquid isoprene composition of claim 1, wherein the liquid isoprene composition further comprises carbon dioxide in an amount between about 0.01% and about 1% by weight.

4. The liquid isoprene composition of claim 1, wherein the liquid isoprene composition further comprises carbon dioxide in an amount between about 0.05% and about 1% by weight.

5. The liquid isoprene composition of claim 1, wherein the liquid isoprene composition further comprises carbon dioxide in an amount between about 0.1% and about 1% by weight.

6. The liquid isoprene composition of claim 1, wherein the liquid isoprene composition further comprises carbon dioxide in an amount between about 0.2% and about 0.7% by weight.

7. The liquid isoprene composition of claim 1, wherein the liquid isoprene composition comprises less than about 1% by weight of water.

* * * * *